United States Patent
Miyamoto et al.

(10) Patent No.: US 10,976,306 B2
(45) Date of Patent: *Apr. 13, 2021

(54) PROTEIN DEGRADATION INDUCING TAG AND USAGE THEREOF

(71) Applicant: Tokyo University of Science Foundation, Tokyo (JP)

(72) Inventors: Etsuko Miyamoto, Tokyo (JP); Masaaki Ozawa, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 300 days.

This patent is subject to a terminal disclaimer.

(21) Appl. No.: 15/736,089

(22) PCT Filed: Jun. 15, 2016

(86) PCT No.: PCT/JP2016/067852
§ 371 (c)(1),
(2) Date: Dec. 13, 2017

(87) PCT Pub. No.: WO2016/204197
PCT Pub. Date: Dec. 22, 2016

(65) Prior Publication Data
US 2018/0164289 A1 Jun. 14, 2018

(30) Foreign Application Priority Data

Jun. 19, 2015 (JP) .............................. JP2015-123740
Apr. 8, 2016 (JP) .............................. JP2016-078324

(51) Int. Cl.
| | |
|---|---|
| *G01N 33/50* | (2006.01) |
| *C07D 239/49* | (2006.01) |
| *C07K 5/00* | (2006.01) |
| *C12Q 1/02* | (2006.01) |
| *A61K 38/00* | (2006.01) |
| *C12N 9/00* | (2006.01) |
| *C07K 14/47* | (2006.01) |
| *C12N 9/76* | (2006.01) |
| *C12P 21/06* | (2006.01) |

(52) U.S. Cl.
CPC ......... *G01N 33/5008* (2013.01); *A61K 38/00* (2013.01); *C07D 239/49* (2013.01); *C07K 5/00* (2013.01); *C07K 14/4703* (2013.01); *C12N 9/00* (2013.01); *C12N 9/6427* (2013.01); *C12P 21/06* (2013.01); *C12Q 1/02* (2013.01); *C07K 2319/70* (2013.01); *C07K 2319/95* (2013.01); *G01N 2500/02* (2013.01); *G01N 2500/10* (2013.01)

(58) Field of Classification Search
CPC .. A61K 38/00; C07D 239/49; C07K 14/4703; C07K 5/00; C12N 9/00; C12N 9/6427; C12P 21/06; C12Q 1/02; G01N 2500/02; G01N 2500/10; G01N 33/5008; A61P 43/00

See application file for complete search history.

(56) References Cited

U.S. PATENT DOCUMENTS

| | | | |
|---|---|---|---|
| 5,882,941 A | 3/1999 | Essigmann et al. | |
| 7,208,157 B2 | 4/2007 | Dashaies et al. | |
| 2009/0270439 A1 | 10/2009 | Ohyagi | |
| 2010/0074908 A1 | 3/2010 | Solomon et al. | |
| 2012/0115232 A1 | 5/2012 | Kanemaki et al. | |
| 2013/0190340 A1* | 7/2013 | Hedstrom ............. | C07C 211/12 514/275 |
| 2016/0264627 A1 | 9/2016 | Henning et al. | |
| 2018/0164289 A1 | 6/2018 | Miyamoto et al. | |

FOREIGN PATENT DOCUMENTS

| | | |
|---|---|---|
| CN | 2013/0190340 A1 | 6/2013 |
| EP | 3542821 A1 | 11/2017 |
| EP | 3543349 A1 | 9/2019 |
| JP | 2008-081508 A | 4/2008 |
| JP | 2008-533986 A | 8/2008 |
| JP | 2009-149524 A | 7/2009 |
| JP | 2013-056837 | 3/2013 |
| JP | 2013-177444 | 9/2013 |
| WO | WO2000/045165 A1 | 8/2000 |
| WO | WO2008/147536 A1 | 12/2008 |
| WO | WO 2012/003281 | 1/2012 |
| WO | WO 2013/106643 | 7/2013 |
| WO | WO2016/204197 A1 | 12/2016 |

OTHER PUBLICATIONS

Cabrol at al. PLoS One (2009) 4(4): e5724, pp. 1-8 (Year: 2009).*
Lee et al. Nature (2010) 467: 179-188 (Year: 2010).*
Shi et al. abstract from Federation Am. Soc. Exp. Biology Journal (FASEB Journal) (Apr. 1, 2015) vol. 29(1, supplement) (Year: 2015).*
Pullarkat et al. Hemoglobin (2014) 38(3): 188-195 (Year: 2014).*
I.N. Lavrik et al: "Caspases: pharmacological manipulation of cell death", Journal of Clinical Investigation, vol. 115, No. 10, Oct. 1, 2005 (Oct. 1, 2005), pp. 2665-2672, XP055522159.
J.T. Nguyen: "Direct activation of the apoptosis machinery as a mechanism to target cancer cells", Proceedings of the National Academy of Sciences, vol. 100, No. 13, Jun. 16, 2003 (Jun. 16, 2003), pp. 7533-7538, XP055072593.
Niki Chondrogianni et al: "Proteasome activation delays aging in vitro and in vivo", Free Radical Biology and Medicine, vol. 71, Jun. 1, 2014 (Jun. 1, 2014), pp. 303-320, XP055361652.
Florian Lienert et al: "Synthetic biology in mammalian cells: next generation research tools and therapeutics", Nature Reviews Molecular Cell Biology, vol. 15, No. 2, Jan. 17, 2014 (Jan. 17, 2014), pp. 95-107, XP055206837.
"Invitation pursuant to Rule 62a(1) EPC and Rule 63(1) EPC" issued in the EP Patent Application No. EP16811671.3, dated Nov. 20, 2018.

(Continued)

*Primary Examiner* — Susan M Hanley
(74) *Attorney, Agent, or Firm* — Pearl Cohen Zedek Latzer Baratz LLP

(57) ABSTRACT

Provided are: a protein degradation inducing tag which is a molecule that has affinity with proteases and does not inhibit degradation of a protein by proteases; a protein degradation inducing molecule that is a conjugate of at least one protein degradation inducing tag and at least one protein binding molecule that binds to a protein; and a usage of those.

11 Claims, 15 Drawing Sheets

(56) References Cited

OTHER PUBLICATIONS

Inobe, "Proteasome ni yoru Tanpakushitsu Bunkai no Bunshi Kiko", Astellas Foundation for Research on Metabolic Disorders, 2012, Heisei 24 Nendo Dai 44 Kai Josei Kenkyu Hokokushu, Adaptor Tanpakushitsu ni yoru Bunkai Yudo.

Itoh, et al., "Development of target protein-selective degradation inducer for protein knockdown", Bioorg. Med. Chem., 2011, 19, 3229-3241.

Demizu, et al., "Design and synthesis of estrogen receptor degradation inducer based on a protein knockdown strategy", Bioorg. Med. Chem. Lett., 2012, 15, 1793-1796.

Hines, et al., "Posttranslational protein knockdown coupled to receptor tyrosine kinase activation with phosphoPROTACs", Proc. Natl. Acad. Sci. U.S.A., 2013, 110(22), 8942-8947.

Long, et al., "Inhibitor Mediated Protein Degradation", Chem. Biol., 2012, 19(5), 629-637.

Neklesa, et al., "Greasy tags for protein removal", Nature, 2012, 487, 308-309.

International Search Report for PCT International Application No. PCT/JP2016/067852 dated Sep. 20, 2016.

Shi, Y. et al., Boc3Arg-Linked Ligands Induce Degradation by Localizing Target Proteins to the 20S Proteasome, ACS Chem Biol, Oct. 5, 2016, vol. 11, p. 3328-3337, ISSN 1554-8937.

Gurung A. B. et al., Significance of Ras Signaling in Cancer and Strategies for its Control, Oncology & Hematology Review, Nov. 23, 2015, vol. 11, No. 2, pp. 147-152.

Sun Q. et al., Discovery of Small Molecules that Bind to K-Ras and Inhibit Sos-Mediated Activation, Angew Chem Int Ed Engl, May 8, 2012, vol. 51, No. 25, pp. 6140-6143.

Office Action issued in the related SG Patent Application No. SG11201904296R, dated Oct. 1, 2020.

Zhi Tan et al., Past, Present, and Future of Targeting Ras for Cancer Therapies, Mini Reviews in Medicinal Chemistry, vol. 16, No. 5, Feb. 1, 2016 (Feb. 1, 2016), pp. 345-357, XP55731807.

Extended European Search Report issued in the related EP Patent Application No. EP17870778.2, dated Oct. 5, 2020.

Shkedy et al., FEBS Lett. (1994) 348: 126-130 (Year: 1994).

Office Action issued in the related U.S. Appl. No. 16/349,708, dated Oct. 1, 2020.

Office Action issued in the CN Patent Application No. CN201680048166.8, dated Jul. 22, 2020.

Kovrigina, E. A. et al., The Ras G Domain Lacks the Intrinsic Propensity to Form Dimers, Biophys J, 2015, vol. 109, pp. 1000-8, ISSN 0006-3495.

Bell, S. et al., p. 53 Contains Large Unstructured Regions in its Native State, J Mol Biol, 2002, vol. 322, pp. 917-27, ISSN 0022-2836.

Weisi Wang et al.: "Small molecule agents targeting the p53-MDM2 pathway for cancer therapy", Medicinal Research Reviews, vol. 32, No. 6, Nov. 16, 2012 (Nov. 16, 2012), pp. 1159-1196, XP055115939, ISSN; 0198-6325, DOI: 10. 1002/med.20236.

Yoshikazu Johmura et al.: "SCFFbxo22-KDM4A targets methylated p53 for degradation and regulates senescence", Nature Communications, vol. 7, No. 1, Feb. 12, 2016 (Feb. 12, 2016), XP055686014, DOI: 10.1038/ncomms10574.

Extended European Search Report issued in the EP Patent Application No. 17871163.6, dated Apr. 24, 2020.

* cited by examiner

PROTEIN DEGRADATION INDUCING TAG AND USAGE THEREOF

CROSS-REFERENCE TO RELATED APPLICATIONS

This application is a National Phase Application of PCT International Application No. PCT/JP2016/067852, entitled "PROTEIN DEGRADATION INDUCING TAG AND USAGE THEREOF", International Filing Date Jun. 15, 2016, published on Dec. 22, 2016 as International Publication No. WO 2016/204197, which in turn claims priority from Japanese Application No. 2015-123740, filed Jun. 19, 2015 and Japanese Application No. 2016-078324, filed Apr. 8, 2016, all of which are incorporated herein by reference in their entirety.

TECHNICAL FIELD

The present disclosure relates to a protein-degradation inducing tag and use thereof.

BACKGROUND ART

Controlling the amount (expression) of a target protein in a cell, a living body, and the like is very useful for analyzing the functions of the target protein and life phenomena in which the target protein is involved. When a target protein is responsible for a disease, the disease can be prevented or treated by decreasing the amount of the target protein.

As a conventional technique for controlling the amount of a target protein at the DNA level, known is the gene knockout technique in which a gene coding the target protein is made defective. As another technique for controlling the amount of a target protein at the RNA level, known is the RNAi (RNA interference) technique in which mRNA of the target protein is degraded with siRNA (small interfering RNA). However, the gene knockout technique is time consuming and expensive, and in addition, may involve bioethical issues. Further, the gene knockout technique cannot be applied to medicine because the gene of a target protein itself is made defective in the technique. Meanwhile, the RNAi technique suffers from off-target effects, and thus the amount of a target protein is difficult to be controlled in a specific manner. Further, the RNAi technique has been challenged in terms of the delivery of siRNA, and many problems need to be solved for applying to medicine.

In view of the above circumstances, a technique has recently gathered much attention in which a target protein is degraded in a cell to control the amount of the target protein at the protein level. This technique is roughly categorized into an ubiquitin dependent technique in which ubiquitination of a target protein is used and an ubiquitin independent technique in which ubiquitination of a target protein is not used.

As the ubiquitin dependent technique, known is a technique in which a complex is used, the complex having a structure where a molecule capable of binding to a target protein is linked to a molecule capable of binding ubiquitin ligase (E3) (For example, see Japanese Unexamined Patent Application Publication No. 2013-056837 U.S. Pat. No. 7,208,157, a report by Itoh, Y. et al., (Itoh, Y. et al., "Development of target protein-selective degradation inducer for protein knockdown.", Bioorg. Med. Chem., 2011, 19, 3229-3241), a report by Demizu et al., (Demizu, Y. et al., "Design and synthesis of estrogen receptor degradation inducer based on a protein knockdown strategy.", Bioorg. Med. Chem. Lett., 2012, 15, 1793-1796), and a report by Hines et al. (Hines, J. et al., "Posttranslational protein knockdown coupled to receptor tyrosine kinase activation with phosphoPROTACs.", Proc. Natl. Acad. Sci. U.S.A., 2013, 110(22), 8942-8947)) This technique involves allowing a target protein to be connected with ubiquitin ligase through the aforementioned complex to specifically ubiquitinate the target protein. This can lead the target protein to degradation by a proteasome. It is noted that the aforementioned complex may also be referred to as SNIPER (Specific and Nongenetic IAP-dependent Protein ERaser), PROTAC (PROteolysis TArgeting Chimera), and the like.

As the ubiquitin independent technique, known is a technique in which a complex is used, the complex having a structure where a molecule capable of binding to a target protein is linked to a hydrophobic tag (for example, see WO2012/003281, a report by Long et al. (Long, M. J. et al., "Inhibitor mediated protein degradation.", Chem. Biol., 2012, 19(5), 629-637), and a report by Neklesa et al. (Neklesa, T. K. et al., "Greasy tags for protein removal.", Nature, 2012, 487, 308-309)). This technique involves allowing the aforementioned complex to bind with a target protein to mimic a partially unfolded state of the target protein. This appears to lead the target protein to degradation by a proteasome.

DISCLOSURE OF THE INVENTION

Problems to be Solved by the Invention

However, the aforementioned ubiquitin dependent technique involving use of a complex having a structure where a molecule capable of binding to a target protein is linked to a molecule capable of binding ubiquitin ligase suffers from low versatility. That is, there are 1000 or more types of ubiquitin ligases in mammal, and ubiquitin ligase plays an important role in recognition of a target protein. Therefore, the complex needs to be individually designed per target protein. Further, the requirement of preparing an individually designed complex per target protein means that the target protein has to be known. Therefore, the technique is difficult to apply, for example, as a tool for identifying a target protein among degraded proteins.

On the other hand, the aforementioned ubiquitin independent technique involving use of a complex having a structure where a molecule capable of binding to a target protein is linked to a hydrophobic tag suffers from low cell membrane permeability and high cytotoxicity due to the hydrophobic tag.

In view of the above circumstances, an object of the present disclosure is to provide a novel protein-degradation inducing tag configured to induce degradation of a target protein, and use thereof.

Means for Solving the Problems

Specific means for achieving the above object include the following embodiments.

(1) A protein-degradation inducing tag, which is a molecule having an affinity with a protease without inhibiting degradation of a protein by the protease.

(2) The protein-degradation inducing tag according to (1), in which the protein-degradation inducing tag has a structure where a proteasome inhibitory activity of a protease inhibitor is inactivated.

(3) The protein-degradation inducing tag according to (1), in which the protease is a proteasome.

(4) The protein-degradation inducing tag according to (3), in which the protein-degradation inducing tag has a structure where a proteasome inhibitory activity of a proteasome inhibitor is inactivated.

(5) The protein-degradation inducing tag according to (4), in which the proteasome inhibiting activity is an inhibitory activity against at least one selected from a caspase-like activity, a trypsin-like activity, and a chymotrypsin-like activity.

(6) A method of screening for a protein-degradation inducing tag, the method including a step of selecting a molecule having an affinity with a protease without inhibiting degradation of a protein by the protease from candidate molecules.

(7) The method of screening for a protein-degradation inducing tag according to (6), in which the protease is a proteasome.

(8) A method of manufacturing a protein-degradation inducing tag, the method including a step of a modifying a structure of an active site of a protease inhibitor to inactivate a protease inhibitory activity.

(9) The method of manufacturing a protein-degradation inducing tag according to (8), the method further including a step of selecting, as the protease inhibitor, a molecule having an affinity with a protease and inhibiting degradation of a protein by the protease from candidate molecules.

(10) A library of protein-degradation inducing tags, including two or more types of protein-degradation inducing tags, each of the two or more types of protein-degradation inducing tags being the protein-degradation inducing tag according to any one of (1) to (5).

(11) A protein-degradation inducing molecule, which is a conjugate of at least one protein-degradation inducing tag and at least one protein binding molecule capable of binding to a protein, the at least one protein-degradation inducing tag being the protein-degradation inducing tag according to any one of (1) to (5).

(12) A library of protein-degradation inducing molecules, including two or more types of protein-degradation inducing molecules, each of the two or more types of protein-degradation inducing molecules being the protein-degradation inducing molecule according to (11).

(13) A pharmaceutical composition including the protein-degradation inducing tag according to any one of (1) to (5) or the protein-degradation inducing molecule according to (11).

(14) A method of degrading a target protein, the method including a step of inducing degradation of the target protein using the protein-degradation inducing tag according to any one of (1) to (5) or the protein-degradation inducing molecule according to (11).

(15) A method of performing functional analysis on a target protein, the method including a step of inducing degradation of the target protein using the protein-degradation inducing tag according to any one of (1) to (5) or the protein-degradation inducing molecule according to (11).

(16) A method of identifying a target protein, the method including a step of inducing degradation of the target protein using the protein-degradation inducing tag according to any one of (1) to (5) or the protein-degradation inducing molecule according to (11), and a step of identifying a protein subjected to degradation induced by the protein-degradation inducing tag or the protein-degradation inducing molecule.

(17) A method of identifying a pathway molecule through a target protein, the method including a step of inducing degradation of the target protein using the protein-degradation inducing tag according to any one of (1) to (5) or the protein-degradation inducing molecule according to (11), and a step of identifying a protein showing an altered activity or expression, the protein being different from the target protein.

(18) A method of screening for a protein-degradation inducing tag or a protein-degradation inducing molecule, the method including a step of introducing the protein-degradation inducing tag according to any one of (1) to (5), the library of protein-degradation inducing tags according to (10), the protein-degradation inducing molecule according to (11), or the library of protein-degradation inducing molecules according to (12) into a system including a target protein, and selecting a protein-degradation inducing tag or protein-degradation inducing molecule which has induced degradation of the target protein.

(19) The method of screening for a protein-degradation inducing tag or a protein-degradation inducing molecule according to (18), wherein the target protein is a disease causative agent, and the protein-degradation inducing tag or the protein-degradation inducing molecule which has induced degradation of the target protein is selected as a candidate ingredient for preventing or treating a disease.

(20) A method of screening for a candidate ingredient for preventing or treating a disease, the method including a step of supplying the protein-degradation inducing tag according to any one of (1) to (5), the library of protein-degradation inducing tags according to (10), the protein-degradation inducing molecule according to (11), or the library of protein-degradation inducing molecules according to (12) into a disease model system, and selecting a protein-degradation inducing tag or a protein-degradation inducing molecule which has improved a condition of the disease.

(21) A method of screening for a candidate ingredient for preventing or treating a disease, the method including a step of introducing the protein-degradation inducing tag according to any one of (1) to (5), the library of protein-degradation inducing tags according to (10), the protein-degradation inducing molecule according to (11), or the library of protein-degradation inducing molecules according to (12) into a disease model system, and extracting a protein-degradation inducing tag or a protein-degradation inducing molecule which has aggravated a condition of the disease, and selecting a protein subjected to degradation induced by the extracted protein-degradation inducing tag or the extracted protein-degradation inducing molecule.

(22) A method of specifying a disease-related protein, the method including a step of introducing the protein-degradation inducing tag according to any one of (1) to (5), the library of protein-degradation inducing tags according to (10), the protein-degradation inducing molecule according to (11), or the library of protein-degradation inducing molecules according to (12) into a disease model system, and extracting a protein-degradation inducing tag or a protein-degradation inducing molecule which has altered a condition of a disease, and selecting a protein subjected to degradation induced by the extracted protein-degradation inducing tag or the extracted protein-degradation inducing molecule.

Effects of the Invention

According to the present disclosure, a novel protein-degradation inducing tag configured to induce degradation of a protein, and use thereof can be provided.

PREFERRED MODE FOR CARRYING OUT THE INVENTION

Figure 1:
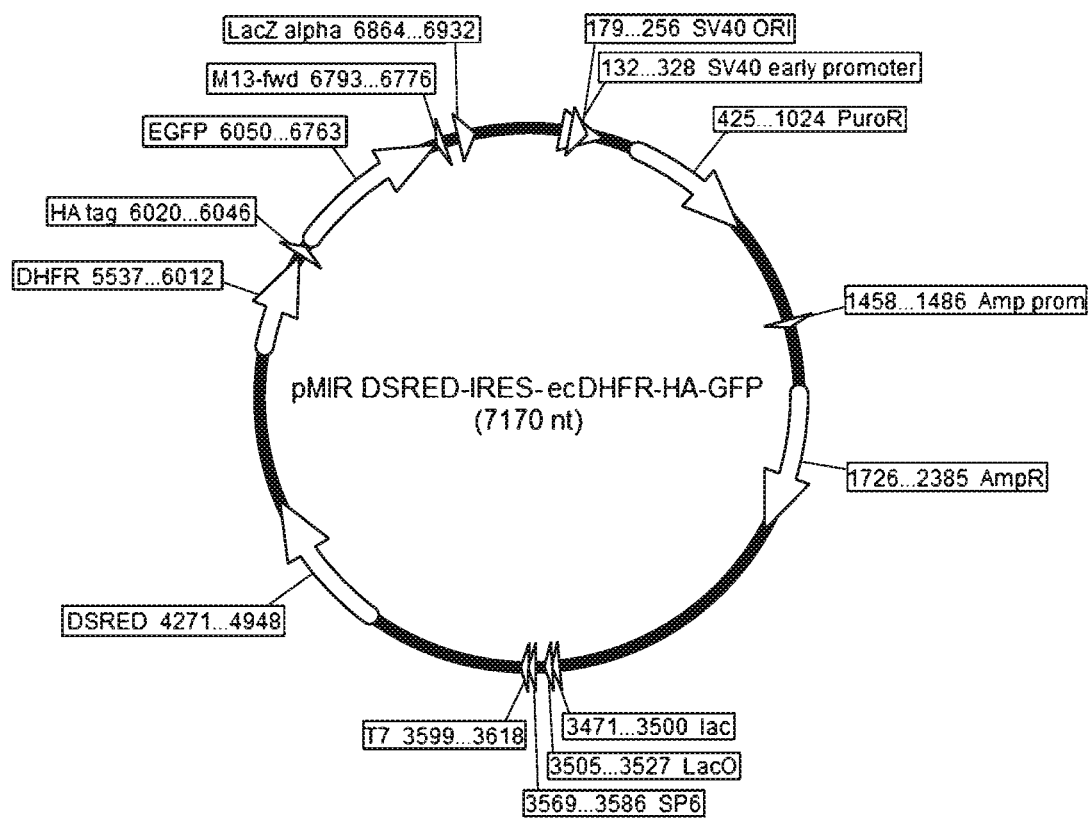
FIG. 1 shows the plasmid map of a plasmid (pMIR DsRed-IRES-ecDHFR-HA-GFP) used in Example.

Below, the embodiments of the present invention will be described in detail. However, the present invention shall not be limited to the following embodiments.

The term "protein" as used herein refers to any having two or more amino acid residues, and encompasses a so-called "peptide." A range of numerical values specified using "—" as used herein refers to a range including values indicated before and after "—" as the minimum value and the maximum value, respectively. The term "step" as used herein encompasses a step independent from the other steps as well as a step which can not be clearly separated from the other steps as long as the purpose of that step can be achieved.

Protein-Degradation Inducing Tag

The protein-degradation inducing tag according to the present disclosure is a molecule having an affinity with a protease without inhibiting degradation of a protein by the protease. The protein-degradation inducing tag is used to lead a protein directly bound or indirectly bound through a protein binding molecule to degradation (knockdown) by a protease. The protein-degradation inducing tag can lead a target protein to degradation (knockdown) by a protease without ubiquitination of the target protein (i.e., in a ubiquitin independent manner), the protein-degradation inducing tag being used alone when the protein-degradation inducing tag is capable of binding to the target protein, or conjugated (the protein-degradation inducing molecule described below) to a protein binding molecule capable of binding to the target protein when the protein-degradation inducing tag is incapable of binding to the target protein. It is noted that the phrase "the protein-degradation inducing tag is capable of binding to a target protein" means that the protein-degradation inducing tag is capable of binding to the target protein via a covalent bond, a hydrogen bond, a hydrophobic bond, Van der Waals force, and the like. There is no particular limitation for the binding mode thereof.

Below, the above protein-degradation inducing tag may also be referred to a CiKD (Chemical interaction and KnockDown) tag.

There is no particular limitation for the protease, and any molecule having a protease activity can be used. For example, it may be a protease complex such as a proteasome, or may be a protease other than the proteasome. Alternatively, it may be a portion of a proteasome as long as the portion has a protease activity.

Examples of the proteasome include 26S proteasome, an immunoproteasome, and a thymus proteasome. 26S proteasome is composed of 20S proteasome and two units of 19S proteasome, the two units of 19S proteasome being attached to the 20S proteasome. 20S proteasome has a cylindrical structure in which an α-ring consisting of 7 subunits of α1 to α7 and a β-ring consisting of 7 subunits of β1 to β7 are stacked in order of αββα, and β1, β2, and β5 show catalytic activities of a caspase-like activity, a trypsin-like activity, and a chymotrypsin-like activity, respectively. In the immunoproteasome, the catalytic subunits β1, β2, and β5 are replaced with β1i, β2i, and β5i, respectively (Science, 1994, 265, 1234-1237). In the thymus proteasome, β5t which is expressed specifically in cortical thymic epithelial cells (cTEC) is incorporated along with β1i and β2i (Science, 2007, 316, 1349-1353).

Examples of a protease other than the proteasome include β-secretase, γ-secretase, aminopeptidase, angiotensin-converting enzyme, bromelain, calpine I, calpine II, carboxypeptidase A, carboxypeptidase B, carboxypeptidase P, carboxypeptidase Y, caspase 1, caspase 2, caspase 3, caspase 5, caspase 6, caspase 7, caspase 8, caspase 9, caspase 13, cathepsin B, cathepsin C, cathepsin D, cathepsin G, cathepsin L, chymotrypsin, clostripain, collagenase, complement C1r, complement C1s, complement factor B, complement factor D, dipeptidyl peptidase I, dipeptidyl peptidase II, dipeptidyl peptidase IV, dispase, elastase, endoproteinase Arg-C, endoproteinase Glu-C, endoproteinase Lys-C, ficin, granzyme B, kallikrein, leucine aminopeptidase, matrix metalloprotease, metalloprotease, papain, pepsin, plasmin, pro-caspase 3, pronase E, proteinase K, renin, thermolysin, thrombin, trypsin, cytosol alanyl aminopeptidase, enkephalinase, neprilysin, and the like.

As used herein, the phrase "having an affinity with a protease" means the capability of binding to a protease, for example, via a covalent bond, a hydrogen bond, a hydrophobic bond, Van der Waals force, and the like. When the thermal stability of a protease changes in the presence of a protein-degradation inducing tag, the protein-degradation inducing tag can be considered as capable of interacting with that protease.

As used herein, the phrase "without inhibiting degradation of a protein by a protease" means that, for example, the protein-degradation inducing tag does not bind to the degradation active site of the protease via a covalent bonding. When a protein is degraded by a protease in the presence of a protein-degradation inducing tag, and the degradation of the protein is inhibited in the presence of a protease inhibitor, the protein-degradation inducing tag can be considered not to inhibit the degradation of the protein by the protease.

Examples of the protein-degradation inducing tag include low molecular weight compounds, natural products, peptides, and the like. The protein-degradation inducing tag has a molecular weight within the range of, for example, 50 to 5000.

There is no particular limitation for the structure of the protein-degradation inducing tag as long as the protein-degradation inducing tag has an affinity with a protease without inhibiting degradation of a protein by the protease. The protein-degradation inducing tag can be obtained from candidate molecules by the screening method as described below, and can also be manufactured according to the method of manufacture as described below.

In a certain embodiment, for example, the protein-degradation inducing tag may have a structure represented by following formula (I):

In the formula (I), $R^1$ and $R^2$ each independently represent a hydrocarbon group having 1 to 20 carbon atoms, an alkoxy group having 1 to 20 carbon atoms, an aryloxy group having 6 to 20 carbon atoms, a hydroxy group, a carboxy group, an amino group, or a halogeno group.

Examples of the hydrocarbon group include an alkyl group, an alkenyl group, an aryl group, combinations thereof, and the like. Specifically, the followings can be mentioned: an alkyl group having 1 to 20 carbon atoms such as a methyl group and an ethyl group; an alkenyl group having 2 to 20 carbon atoms such as a vinyl group and an allyl group; an aryl group having 6 to 20 carbon atoms such as a phenyl group and a naphthyl group; an arylalkyl group having 7 to 20 carbon atoms such as a benzyl group and a phenethyl group; an alkylaryl group having 7 to 20 carbon atoms such as a tolyl group and a xylyl group; and the like. Examples of the halogeno group include a fluoro group, a chloro group, a bromo group, and the like.

In another embodiment, the protein-degradation inducing tag may have a structure in which the proteasome inhibitory activity of a proteasome inhibitor is inactivated. More specifically, at least one inhibitory activity selected from a caspase-like activity, a trypsin-like activity, and a chymotrypsin-like activity can be mentioned as the proteasome inhibitory activity.

The term "structure in which a proteasome inhibitory activity is inactivated" as used herein encompasses a structure in which a proteasome inhibitory activity is attenuated in addition to a structure in which a proteasome inhibitory activity is completely eliminated. In a certain embodiment, the protein-degradation inducing tag has a 50% inhibition concentration ($IC_{50}$) against at least one selected from a caspase-like activity, a trypsin-like activity, and a chymotrypsin-like activity which is 2 times or more of the 50% inhibition concentration ($IC_{50}$) of the original proteasome inhibitor.

As the proteasome inhibitor, any compound having a proteasome inhibitory activity can be used. A proteasome inhibitor is a compound which has an affinity with a proteasome (a protease complex), and inhibits degradation of a protein by a proteasome. Therefore, a protein-degradation inducing tag may be obtained by replacing the active site of a proteasome inhibitor with another structural moiety to inactivate the proteasome inhibitory activity. Proteasome inhibitors have been progressively explored as anticancer agent and the like. Many compounds have been approved as pharmaceutical products, or are under clinical trials. Moreover, many of proteasome inhibitors have relatively small molecular weights and low hydrophobicity, and are less problematic in terms of cell membrane permeability, cytotoxicity, and the like. For these reasons, synthesizing a protein-degradation inducing tag based on a proteasome inhibitor is quite reasonable and efficient.

Examples of the proteasome inhibitor are shown in the following Tables 1 and 2. The proteasome inhibitors shown in Tables 1 and 2 are each a 20S proteasome inhibitor having an affinity with 20S proteasome. However, a proteasome inhibitor which can be used in the present embodiment shall not be limited to these examples.

TABLE 1

| No. | Generic name/ Product name | Structural formula (Circles indicate active sites) | Molecular weight |
|---|---|---|---|
| 1 | Bortezomib | | 384.24 |
| 2 | ALLN (MG-101, Calpain inhibitor I) | | 383.53 |
| 3 | MLN9708 (Ixazomib) | | 517.12 |
| 4 | MLN2238 | | 361.03 |
| 5 | CEP-18770 | | 413.28 |

TABLE 1-continued

| No. | Generic name/Product name | Structural formula (Circles indicate active sites) | Molecular weight |
|---|---|---|---|
| 6 | ONO-7058 (Oprozomib) | | 532.61 |
| 7 | MG-132 | | 475.63 |

TABLE 2

| No. | Generic name/Product name | Structural formula (Circles indicate active sites) | Molecular weight |
|---|---|---|---|
| 8 | Carfilzomib | | 719.92 |
| 9 | BSc-2118 | | 533.66 |
| 10 | PSI | | 604.75 |

TABLE 2-continued

| No. | Generic name/ Product name | Structural formula (Circles indicate active sites) | Molecular weight |
|---|---|---|---|
| 11 | Epoxomicin | | 554.73 |
| 12 | ONX-0914 | | 580.68 |
| 13 | ¹²⁵I-NIP-L₃VS | | 720.64 |
| 14 | NPI-0052 (Marizomib) | | 313.78 |

For example, bortezomib as a boronic acid-based proteasome inhibitor is known to inhibit a proteasome activity when the boronyl group as an active site covalently binds to the degradation active site of 20S proteasome as shown in the following scheme (Kisselev, A. F. et al., Chemistry & Biology, 2012, 19, 99-115)

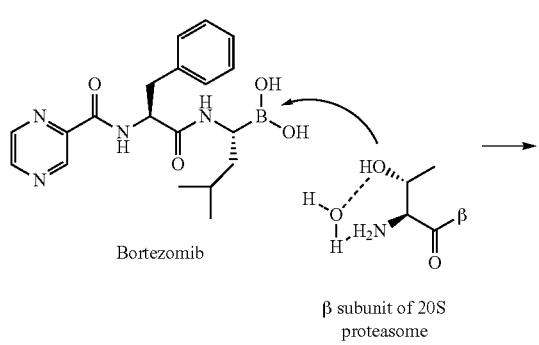

β subunit of 20S proteasome

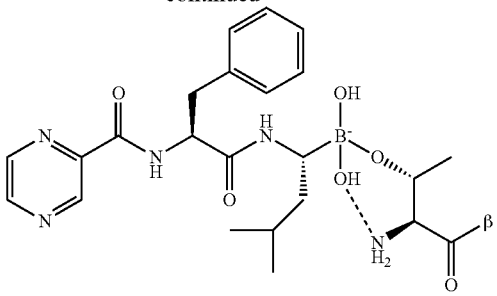

Further, MLN9708 and MLN2238, which are boronic acid-based proteasome inhibitors, are known to inhibit a proteasome activity when the boronic acid ester moiety or the boronyl group as an active site covalently binds to the degradation active site of 20S proteasome as shown in the following scheme (Kisselev, A. F. et al., Chemistry & Biology, 2012, 19, 99-115).

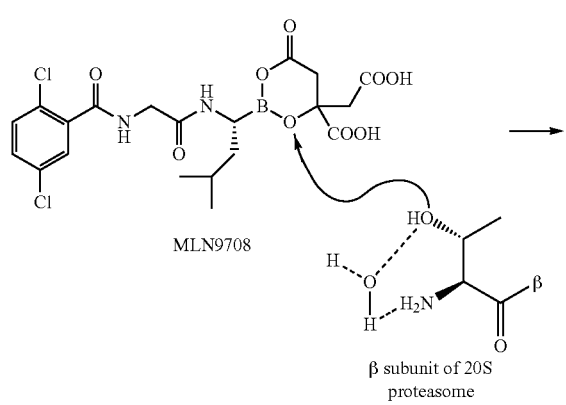

MLN9708

β subunit of 20S proteasome

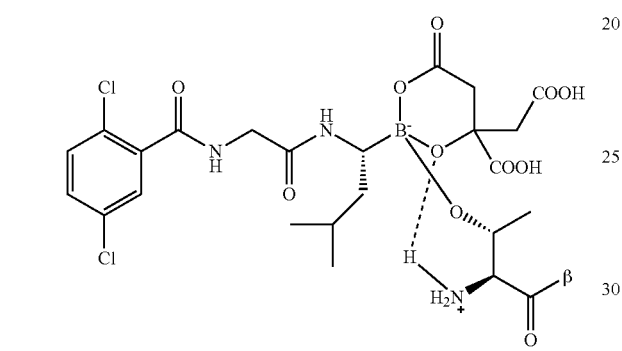

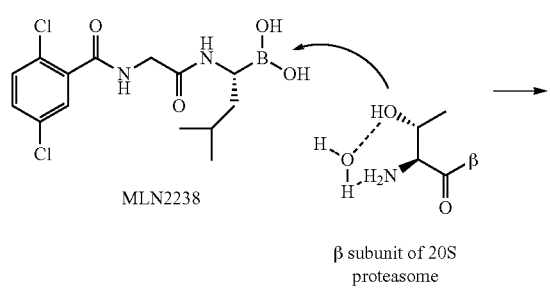

MLN2238

β subunit of 20S proteasome

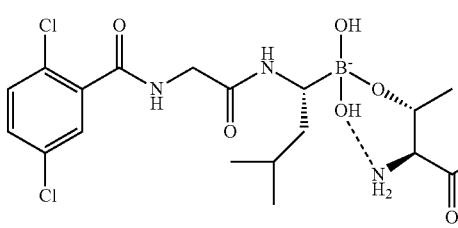

Therefore, a protein-degradation inducing tag may be obtained by replacing the boronyl group or the boronic acid ester moiety as the active sites of bortezomib, MLN9708, and MLN2238 with another structural moiety (a carboxy group, an alkyl group, an aryl group, an amino group, a hydroxy group, and the like) to inactive the proteasome inhibitory activity.

It is noted that even for other boronic acid-based proteasome inhibitors such as CEP-18770, a protein-degradation inducing tag can be obtained by replacing the active site with another structural moiety (a carboxy group, an alkyl group, an aryl group, an amino group, a hydroxy group, and the like).

Further, ALLN, which is an aldehyde proteasome inhibitor, is known to inhibit a proteasome activity when the formyl group as an active site covalently binds to the degradation activity site of 20S proteasome as shown in the following scheme (Kisselev, A. F. et al., Chemistry & Biology, 2012, 19, 99-115).

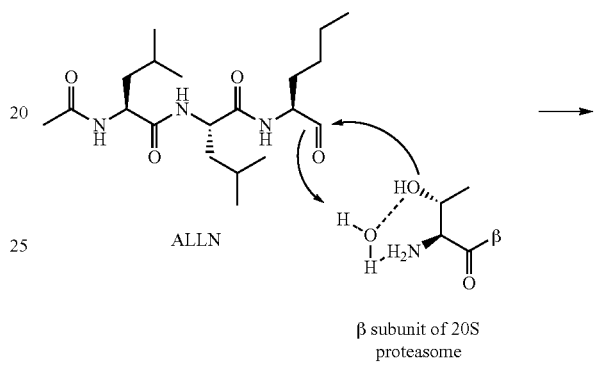

ALLN

β subunit of 20S proteasome

Therefore, a protein-degradation inducing tag can be obtained by replacing the formyl group as the active site of ALLN with another structural moiety (a carboxy group, an alkyl group, an aryl group, an amino group, a hydroxy group, and the like) to inactivate the proteasome inhibitory activity.

It is noted that even for other aldehyde proteasome inhibitors such as MG-132, BSc-2118, and PSI, a protein-degradation inducing tag can be obtained by replacing the formyl group as an active site with another structural moiety (a carboxy group, an alkyl group, an aryl group, an amino group, a hydroxy group, and the like).

Examples of the protein-degradation inducing tag having a structure in which the proteasome inhibitory activity of a proteasome inhibitor is inactivated are shown in the following Tables 3 and 4. Examples of the monovalent group represented by R in the tables include a carboxy group, an alkyl group having 1 to 20 carbon atoms, an aryl group having 6 to 20 atoms, an amino group, a hydroxy group, and the like.

TABLE 3
| No. | Structural formula |
|---|---|
| 1 | 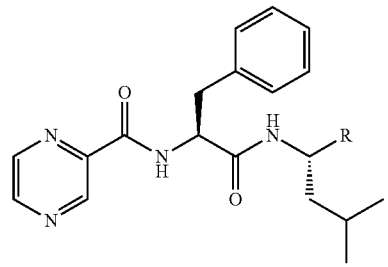 (In the formula, R represents a monovalent group except for 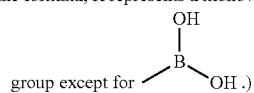.) |
| 2 | 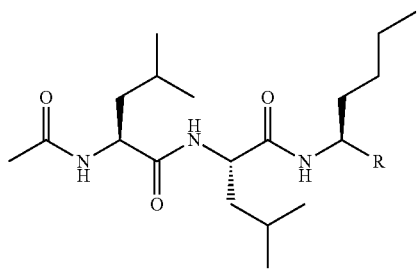 (In the formula, R represents a monovalent group except for —CHO.) |
| 3 | 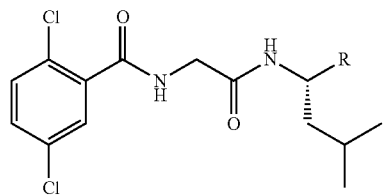 (In the formula, R represents a monovalent group except for 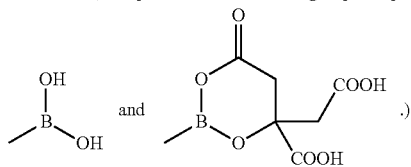.) |
| 4 | 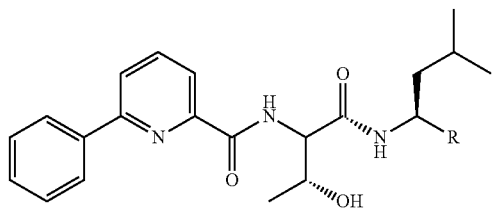 (In the formula, R represents a monovalent group except for 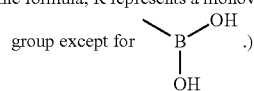.) |

TABLE 3-continued
| No. | Structural formula |
|---|---|
| 5 | 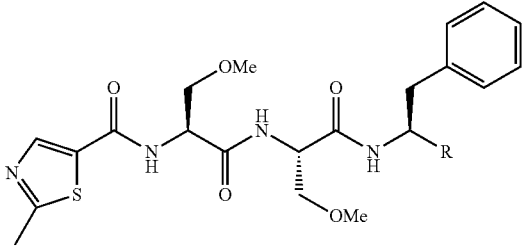 (In the formula, R represents a monovalent group except for 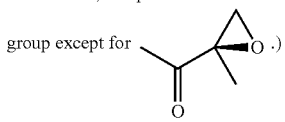.) |
| 6 | 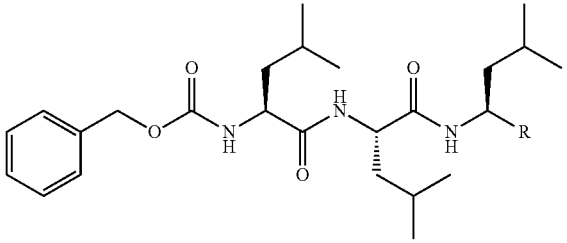 (In the formula, R represents a monovalent group except for —CHO.) |
| 7 | 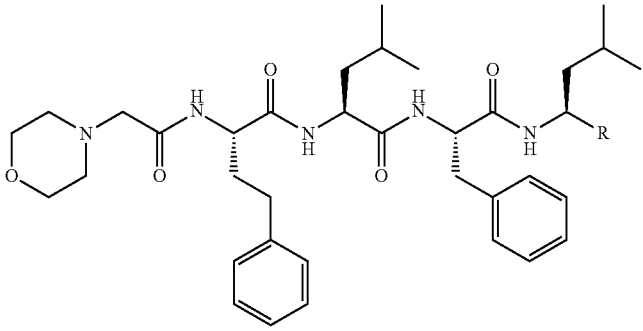 (In the formula, R represents a monovalent group except for 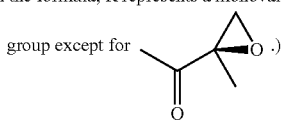.) |

TABLE 4
| No. | Structural formula |
|---|---|
| 8 | 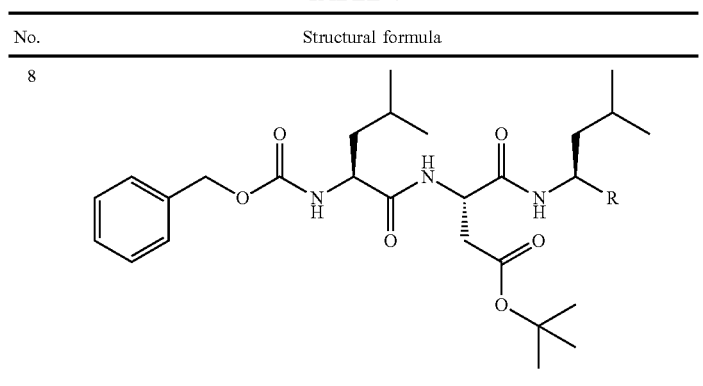 (In the formula, R represents a monovalent group except for —CHO.) |
| 9 | 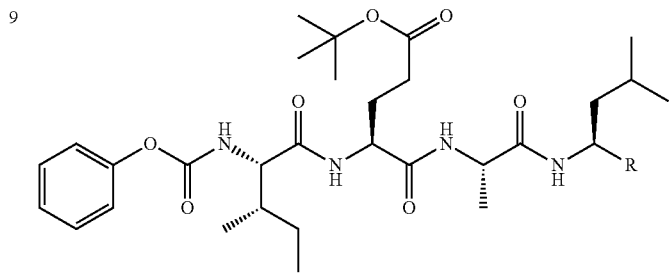 (In the formula, R represents a monovalent group except for —CHO.) |
| 10 | 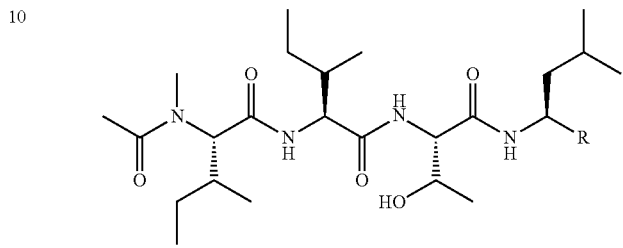 (In the formula, R represents a monovalent group except for 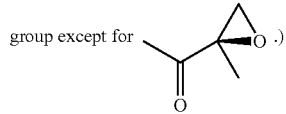.) |
| 11 | 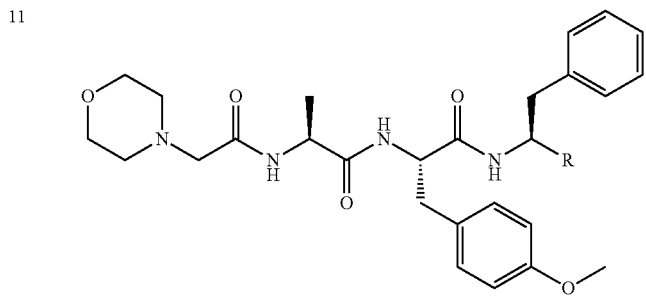 (In the formula, R represents a monovalent group except for 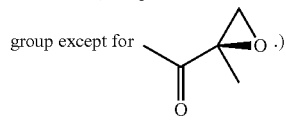.) |

TABLE 4-continued

| No. | Structural formula |
|---|---|
| 12 | [Structure: HO, 125I, O2N substituted phenyl-CH2-C(O)-NH-CH(CH2CH(CH3)2)-C(O)-NH-CH(CH2CH(CH3)2)-C(O)-NH-CH(R)(CH2CH(CH3)2)]<br><br>(In the formula, R represents a monovalent group except for -CH=CH-S(O)2-.) |
| 13 | [Structure: pyrrolidinone with HO, R, OH substituents, cyclohexenyl group, and CH2CH2Cl chain]<br><br>(In the formula, R represents a monovalent group.) |
| 14 | [Structure: bicyclic furo-pyrrolidinone with HO, R substituents and cyclohexenyl group]<br><br>(In the formula, R represents a monovalent group.) |

Other examples of the proteasome inhibitor are shown in the following Tables 5 to 10. Even for these proteasome inhibitor, a protein-degradation inducing tag can be obtained by inactivating the proteasome inhibitory activity in a similar way as described above.

TABLE 5

| | 20S proteasome inhibitor | | |
|---|---|---|---|
| No. | Generic name/Product name | Structural formula | Molecular weight |
| 15 | Aspirin | [Structure of aspirin: benzene ring with COOH and O-C(O)-CH3] | 180.15 |
| 16 | Hydroxyurea inhibitor | [Structure: adamantyl-O-phenyl-C≡C-CH(CH3)-N(OH)-C(O)-NH2] | 354.54 |

TABLE 5-continued

20S proteasome inhibitor

| No. | Generic name/ Product name | Structural formula | Molecular weight |
|---|---|---|---|
| 17 | PI-1840 | | 394.47 |
| 18 | PI-083 | | 439.87 |
| 19 | Cerastol | | 450.61 |

TABLE 6

20S proteasome inhibitor (Continued)

| No. | Generic name/ Product name | Structural formula | Molecular weight |
|---|---|---|---|
| 20 | CVT-659 | | 571.66 |

TABLE 6-continued
| | | 20S proteasome inhibitor (Continued) | |
|---|---|---|---|
| No. | Generic name/ Product name | Structural formula | Molecular weight |
| 21 | Capped dipeptide 2 | 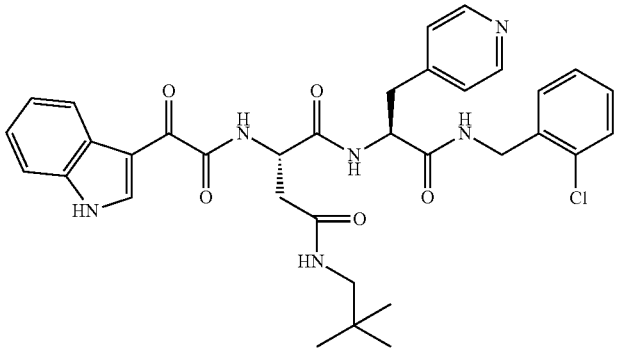 [SMILES: CC(C)(C)CNC(=O)C[C@H](NC(=O)C(=O)c1c[nH]c2ccccc12)C(=O)N[C@@H](Cc1ccncc1)C(=O)NCc1ccccc1Cl] | 645.15 |
| 22 | TMC95A | 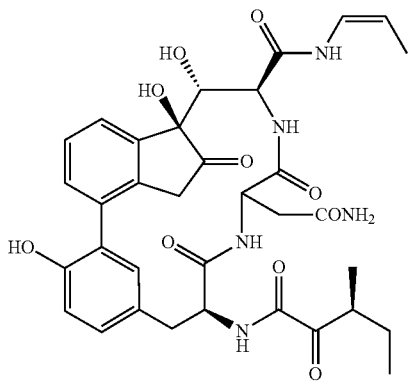 [SMILES: C/C=C\NC(=O)[C@H]1NC(=O)C(CC(N)=O)NC(=O)[C@@H](NC(=O)C(=O)[C@@H](C)CC)Cc2ccc(O)c(c2)-c2cccc3c2CC(=O)[C@@]3(O)[C@@H]1O] | 677.71 |
| 23 | Capped dipeptide 1 | 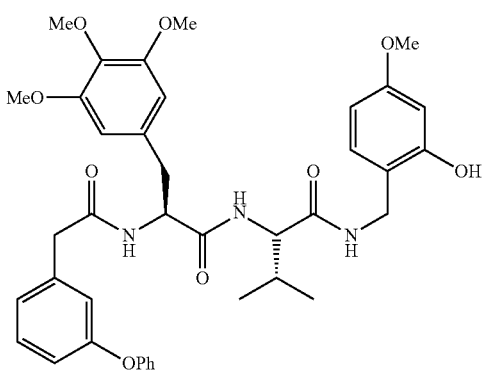 | 699.80 |

TABLE 7

| | | 20S proteasome inhibitor (Continued) | |
|---|---|---|---|
| No. | Generic name/ Product name | Structural formula | Molecular weight |
| 24 | Ritonavir | | 720.94 |
| 25 | Scytonemide A | | 744.89 |
| 26 | Argyrin A | | 824.91 |

TABLE 7-continued 20S proteasome inhibitor (Continued)

| No. | Generic name/ Product name | Structural formula | Molecular weight |
|---|---|---|---|
| 27 | Benzylstatine peptide 1 | | 826.00 |

TABLE 8

19S proteasome inhibitor

| No. | Generic name/ Product name | Structural formula | Molecular weight |
|---|---|---|---|
| 1 | RIP-1 (Rpt 4 inhibitor) | | 1348.76 |

TABLE 9

Inhibitor for a constituent factor other than 20S/19S

| No. | Generic name/ Product name | Structural formula | Molecular weight | Others |
|---|---|---|---|---|
| 1 | JBIR-22 | | 419.52 | PAC-3 (molecule assembly factor inhibition) |

TABLE 10

| | | 20S immunoproteasome inhibitor | | |
|---|---|---|---|---|
| No. | Generic name/ Product name | Structural formula | Molecular weight | Others |
| 1 | PR-957 | | 580.68 | β5i is inhibited |
| 2 | IPSI-001 | | 362.47 | β2i is inhibited |
| 3 | LMP2-sp-ek | | 484.75 | β2i is inhibited |

In another embodiment, the protein-degradation inducing tag may have a structure in which the protease inhibitory activity of a protease inhibitor (except for the proteasome inhibitors described above) is inactivated.

The term "structure in which a protease inhibitory activity is inactivated" as used herein encompasses a structure in which the protease inhibitory activity is attenuated in addition to a structure in which the protease inhibitory activity is completely eliminated. In a certain embodiment, the protein-degradation inducing tag has a 50% inhibition concentration ($IC_{50}$) against a protease as an inhibition target of a protease inhibitor which is 2 times or more of the 50% inhibition concentration ($IC_{50}$) of the original protease inhibitor.

As a protease inhibitor, any compound having a protease inhibitory activity can be used. The protease inhibitor is a compound having an affinity with a protease and inhibiting degradation of a protein by the protease. Therefore, a protein-degradation inducing tag can be obtained by replacing the active site of a protease inhibitor with another structural moiety to inactivate the protease inhibitory activity.

Examples of the protease inhibitor are shown in the following Tables 11 to 78. Protein-degradation inducing tags can be obtained by replacing the active sites of these protease inhibitor with another structural moieties to inactivate the protease inhibitory activities. However, a protease inhibitor which can be used in the present embodiment shall not be limited to these examples. Existing data bases (for example, "MEROPS—the peptidase database" (http://merops.sanger.ac.uk/index.shtml)) can be consulted for information about proteases and protease inhibitors if needed.

TABLE 11

β-secretase inhibitor

| No. | Name | Structural formula | Molecular weight | Protease to be inhibited |
|---|---|---|---|---|
| 1 | OM99-2 | (structure) | 892.99 | |

TABLE 12

γ-secretase inhibitor

| No. | Name | Structural formula | Molecular weight | Protease to be inhibited |
|---|---|---|---|---|
| 1 | γ-Secretase inhibitor | (structure) | 705.83 | |
| 2 | L-685, 458 | (structure) | 672.85 | |

TABLE 13

Aminopeptidase inhibitor

| No. | Name | Structural formula | Molecular weight | Protease to be inhibited |
|---|---|---|---|---|
| 1 | Cysteamine | HS-CH$_2$-CH$_2$-NH$_2$ · HCl | 113.61 | |
| 2 | Bestatin | (structure) · HCl | 344.83 | Aminopeptidase B Leucine aminopeptidase |

TABLE 14

Angiotensin converting enzyme inhibitor

| No. | Name | Structural formula | Molecular weight | Protease to be inhibited |
|---|---|---|---|---|
| 1 | Captopril | | 217.29 | Formation of angiotensin II is inhibited |
| 2 | Fenoldopam monohydrobromide | | 386.67 | |
| 3 | Angiotensin Converting Enzyme Inhibitor | pGlu-Trp-Pro-Arg-Pro-Gln-Ile-Pro-Pro-OH | 1101.26 | |

TABLE 15

Bromelain inhibitor

| No. | Name | Structural formula | Molecular weight | Protease to be inhibited |
|---|---|---|---|---|
| 1 | E-64 | | 357.41 | Cathepsin B<br>Ficin<br>Papain<br>Bromelain |
| 2 | N-Ethylmaleimide | | 125.13 | Calpine<br>Ficin |
| 3 | N-p-Tosyl-L-phenilalanine chloromethyl ketone | | 351.85 | Papain<br>Chymotrypsin<br>Ficin<br>Bromelain |

TABLE 15-continued
Bromelain inhibitor
| No. | Name | Structural formula | Molecular weight | Protease to be inhibited |
|---|---|---|---|---|
| 4 | Sodium iodoacetate | 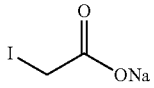 | 207.93 | Carboxypeptidase P<br>Bromelain<br>Ficin<br>Cathepsin |
TABLE 16
Calpain inhibitor
| No. | Name | Structural formula | Molecular weight | Protease to be inhibited |
|---|---|---|---|---|
| 1 | E-64c | 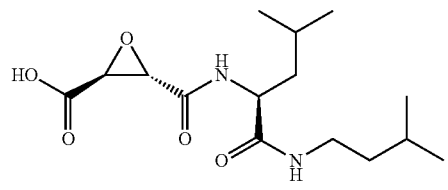 [SMILES: CC(C)CCNC(=O)[C@H](CC(C)C)NC(=O)[C@H]1O[C@@H]1C(=O)O] | 314.38 | |
| 2 | E-64d | 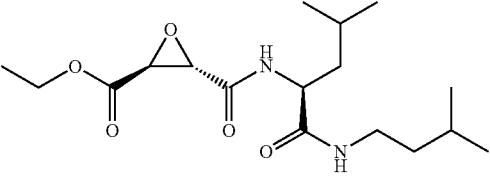 [SMILES: CCOC(=O)[C@H]1O[C@@H]1C(=O)N[C@@H](CC(C)C)C(=O)NCCC(C)C] | 342.43 | |
| 3 | Z-Leu-Leu-Leu-fluoromethyl ketone | 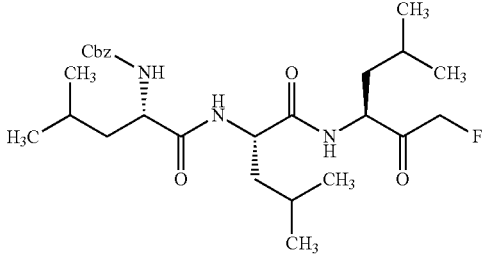 [SMILES: CC(C)C[C@H](NC(=O)[C@H](CC(C)C)NC(=O)[C@H](CC(C)C)NC(=O)OCc1ccccc1)C(=O)CF] | 507.64 | |
| 4 | N-Ethylmaleimide | 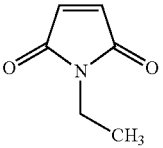 | 125.13 | Ficin<br>Calpine |

TABLE 16-continued

| | | Calpain inhibitor | | |
|---|---|---|---|---|
| No. | Name | Structural formula | Molecular weight | Protease to be inhibited |
| 5 | Antipain dihydro- chloride from microbial source | 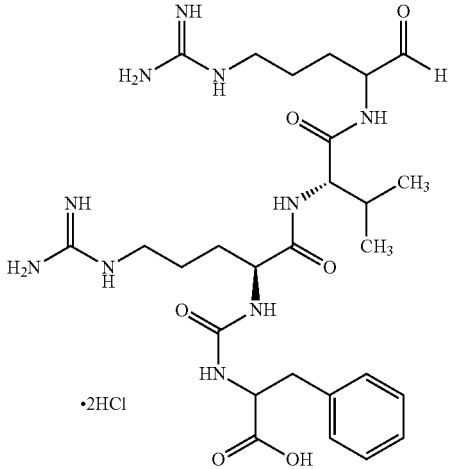 [SMILES: CC(C)[C@H](NC(=O)[C@H](CCCNC(=N)N)NC(=O)NC(Cc1ccccc1)C(=O)O)C(=O)NC(C=O)CCCNC(=N)N] ·2HCl | 677.62 | Calpine Papain Trypsin Cathepsin A Cathepsin B Cathepsin D Plasmin Chymotrypsin Pepsin Granzyme B Thrombin |
| 6 | 4-Chloro- mercuri- benzoic acid | 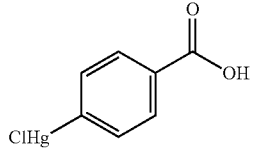 | 357.16 | Calpine Carboxypeptidase Clostripain |
| 7 | Leupeptin | 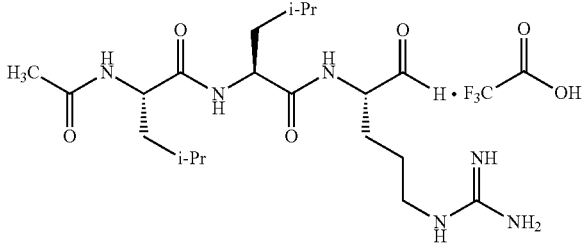 | 426.55 | Plasmin Trypsin Papain Calpine Cathepsin B Thrombin Kallikrein Endoproteinase Chymotrypsin Proteasome (β2) |

TABLE 17

| | | Calpain I inhibitor | | |
|---|---|---|---|---|
| No. | Name | Structural formula | Molecular weight | Protease to be inhibited |
| 1 | Calpain Inhibitor I (ALLN, Ac-LLnL-CHO, MG-101) | 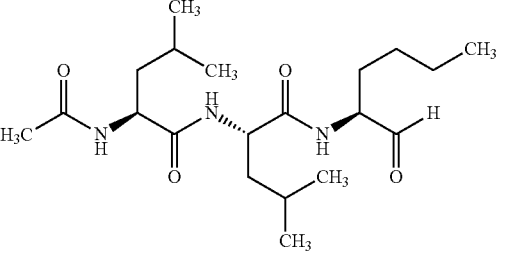 [SMILES: CCCC[C@@H](C=O)NC(=O)[C@H](CC(C)C)NC(=O)[C@H](CC(C)C)NC(C)=O] | 383.53 | Cathepsin B Cathepsin L Calpine Proteasome |

TABLE 17-continued

| | | Calpain I inhibitor | | |
|---|---|---|---|---|
| No. | Name | Structural formula | Molecular weight | Protease to be inhibited |
| 2 | Calpain Inhibitor II | | 401.56 | Cathepsin B Calpine Proteasome |

TABLE 18

| | | Calpain II inhibitor | | |
|---|---|---|---|---|
| No. | Name | Structural formula | Molecular weight | Protease to be inhibited |
| 1 | E-64c | | 314.38 | |
| 2 | Calpain Inhibitor I (ALLN, Ac-LLnL, Ac-LLnL-CHO, MG-101) | | 383.53 | Cathepsin B Cathepsin L Calpine Proteasome |
| 3 | Calpain Inhibitor II | | 401.56 | Cathepsin B Calpine Proteasome |
| 4 | N-Ethyl-maleimide | | 125.13 | Ficin Calpine |

TABLE 18-continued

Calpain II inhibitor

| No. | Name | Structural formula | Molecular weight | Protease to be inhibited |
|---|---|---|---|---|
| 5 | Antipain dihydrochloride from microbial source | 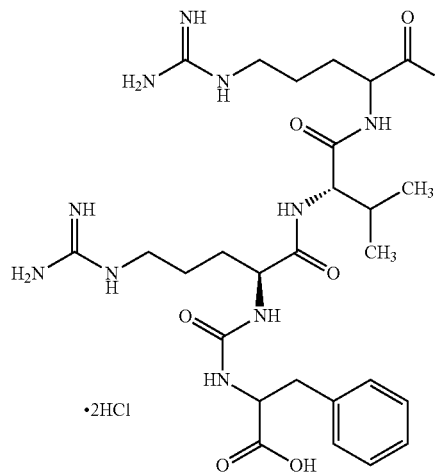 | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 6 | 4-Chloro-mercuribenzoic acid | 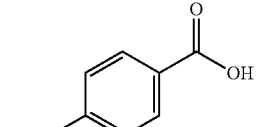 | 357.16 | Calpine<br>Carboxypeptidase<br>Clostripain |
| 7 | Leupeptin | 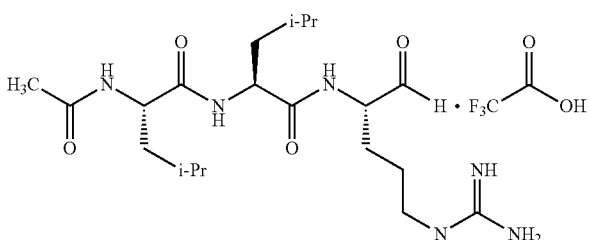 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 19

Carboxypeptidase A/B inhibitor

| No. | Name | Structural formula | Molecular weight | Protease to be inhibited |
|---|---|---|---|---|
| 1 | Ethylene glycol-bis(2-aminoethyl ether)-N,N,N',N'-tetraacetic acid | 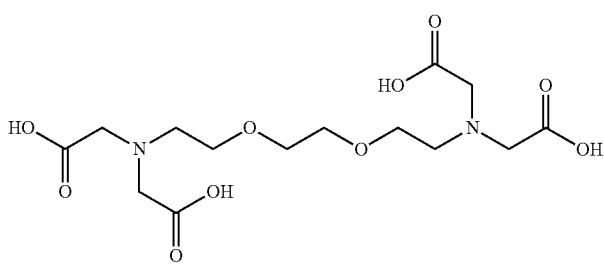 [SMILES: O=C(O)CN(CCOCCOCCN(CC(=O)O)CC(=O)O)CC(=O)O] | 380.35 | Carboxypeptidase A<br>Carboxypeptidase B |

TABLE 19-continued

Carboxypeptidase A/B inhibitor

| No. | Name | Structural formula | Molecular weight | Protease to be inhibited |
|---|---|---|---|---|
| 2 | EDTA disodium salt | 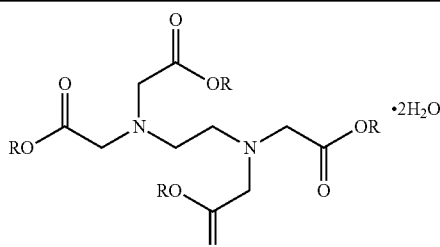<br>R = H or Na (2:2) | 372.24 | Carboxypeptidase A<br>Carboxypeptidase B<br>Dispase<br>Collagenase |
| 3 | Pentetic acid (DETAPAC, DTPA) | 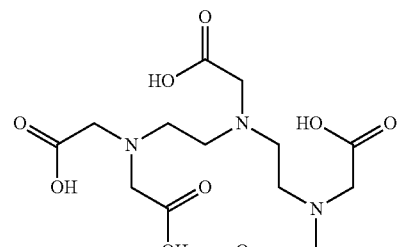 | 393.35 | Carboxypeptidase A<br>Carboxypeptidase B |
| 4 | 1,10-Phenanhtroline monohydrate | 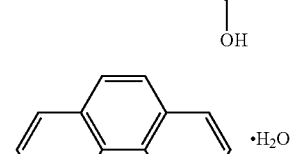 | 198.22 | Carboxypeptidase A<br>Carboxypeptidase B<br>Dispase<br>Leucine aminopeptidase<br>Thermolysin |

TABLE 20

Carboxypeptidase P inhibitor

| No. | Name | Structural formula | Molecular weight | Protease to be inhibited |
|---|---|---|---|---|
| 1 | Diisopropyl-fluorophosphate | $CH_3-CH(CH_3)-O-P(=O)(F)-O-CH(CH_3)-CH_3$ | 184.15 | Carboxypeptidase<br>Chymotrypsin<br>Complement<br>Elastase<br>Kallikrein<br>Plasmin<br>Thrombin<br>Pronase<br>Proteinase |
| 2 | 4-Chloro-mercuribenzoic acid | ClHg–C$_6$H$_4$–COOH | 357.16 | Calpine<br>Carboxypeptidase<br>Clostripain |
| 3 | Diethyl pyrocarbonate (DEP) | $H_3C-CH_2-O-C(=O)-O-C(=O)-O-CH_2-CH_3$ | 162.14 | |
| 4 | Sodium iodoacetate | I–CH$_2$–C(=O)–ONa | 207.93 | Carboxypeptidase P<br>Bromelain<br>Ficin<br>Cathepsin |

TABLE 21

| | | Carboxypeptidase Y inhibitor | | |
|---|---|---|---|---|
| No. | Name | Structural formula | Molecular weight | Protease to be inhibited |
| 1 | Diisopropyl-fluoro-phosphate | $CH_3-CH(CH_3)-O-P(=O)(F)-O-CH(CH_3)-CH_3$ | 184.15 | Carboxypeptidase Chymotrypsin Complement Elastase Endoproteinase Kallikrein Plasmin Thrombin Pronase Proteinase |
| 2 | Phenyl-methane-sulfonyl fluoride | (benzyl-SO₂-F structure) | 174.19 | Thrombin Elastase Plasmin Proteinase |

TABLE 22

| | | Cathepsin B inhibitor | | |
|---|---|---|---|---|
| No. | Name | Structural formula | Molecular weight | Protease to be inhibited |
| 1 | CA-074 | (structure) | 383.44 | |
| 2 | CA-074 methyl ester | (structure) | 397.47 | |
| 3 | E-64 | (structure) | 357.41 | Cathepsin B Ficin Papain Bromelain |
| 4 | Z-Phe-Phe-fluoromethyl ketone (Z-FF-FMK) | (structure) | 462.51 | |

TABLE 22-continued

Cathepsin B inhibitor

| No. | Name | Structural formula | Molecular weight | Protease to be inhibited |
|---|---|---|---|---|
| 5 | Antipain dihydrochloride from microbial source | 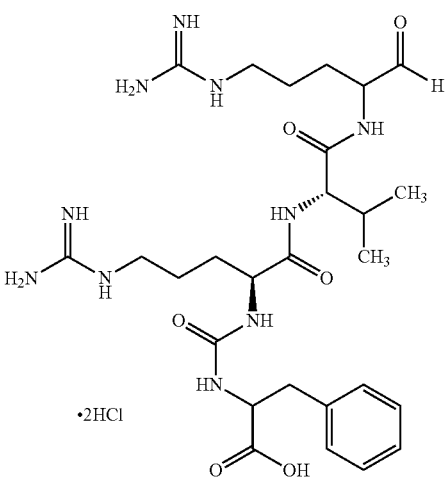 [SMILES: CC(C)[C@H](NC(=O)[C@H](CCCNC(=N)N)NC(=O)NC(Cc1ccccc1)C(=O)O)C(=O)NC(C=O)CCCNC(=N)N] •2HCl | 677.62 | Calpine<br>Papain<br>Trypsin<br>Cathepsin A<br>Cathepsin B<br>Cathepsin D<br>Plasmin<br>Chymotrypsin<br>Pepsin |

TABLE 23

Cathepsin B inhibitor

| No. | Name | Structural formula | Molecular weight | Protease to be inhibited |
|---|---|---|---|---|
| 6 | Calpain Inhibitor I (ALLN, Ac-LLnL-CHO, MG-101) | 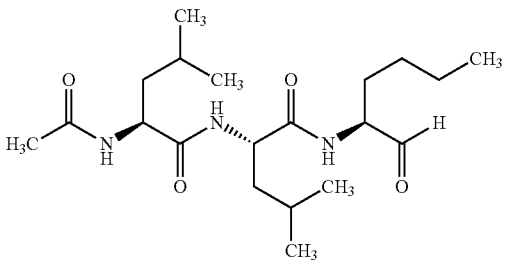 [SMILES: CCCC[C@@H](C=O)NC(=O)[C@H](CC(C)C)NC(=O)[C@H](CC(C)C)NC(C)=O] | 383.53 | Cathepsin B<br>Cathepsin L<br>Calpine<br>Proteasome |
| 7 | Calpain Inhibitor II | 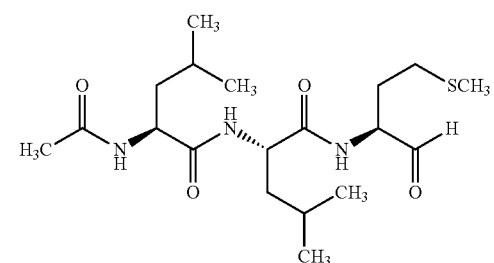 | 401.56 | Cathepsin B<br>Calpine<br>Proteasome |
| 8 | Chymostatin | 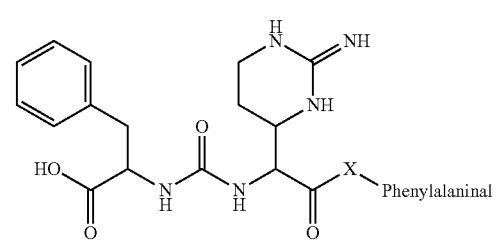<br>Chymostatin A  X = Leu<br>Chymostatin B  X = Val<br>Chymostatin C  X = Ile | A: MW = 607.7<br>B: MW = 593.7<br>C: MW = 607.7 | Chymotrypsin<br>Papain<br>Chymotrypsin-like serine proteinase<br>Cathepsin A, B, C, B, H, L |

TABLE 23-continued

| | | Cathepsin B inhibitor | | |
|---|---|---|---|---|
| No. | Name | Structural formula | Molecular weight | Protease to be inhibited |
| 9 | Leupeptin | [structure of leupeptin with i-Pr groups, acetyl, and guanidino side chain] · F₃C-COOH | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 24

| | | Cathepsin C inhibitor | | |
|---|---|---|---|---|
| No. | Name | Structural formula | Molecular weight | Protease to be inhibited |
| 1 | Sodium iodoacetate | I-CH₂-C(=O)-ONa | 207.93 | Carboxypeptidase P<br>Bromelain<br>Ficin<br>Cathepsin |

TABLE 25

| | | Cathepsin D inhibitor | | |
|---|---|---|---|---|
| No. | Name | Structural formula | Molecular weight | Protease to be inhibited |
| 1 | Antipain dihydrochloride from microbial source | [structure of antipain dihydrochloride] ·2HCl | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 2 | Chymostatin | [structure of chymostatin]<br>Chymostatin A  X = Leu<br>Chymostatin B  X = Val<br>Chymostatin C  X = Ile | A: MW = 607.7<br>B: MW = 593.7<br>C: MW = 607.7 | Chymotrypsin<br>Papain<br>Chymotrypsin-like serine proteinase<br>Cathepsin A, B, C, B, H, L<br>Proteasome (β5) |

TABLE 25-continued

Cathepsin D inhibitor

| No. | Name | Structural formula | Molecular weight | Protease to be inhibited |
|---|---|---|---|---|
| 3 | Pepstatin A | | 685.89 | Pepsin Cathepsin |

TABLE 26

Cathepsin L inhibitor

| No. | Name | Structural formula | Molecular weight | Protease to be inhibited |
|---|---|---|---|---|
| 1 | Z-Phe-Phe-fluoromethyl ketone (2-FF-FMK) | | 462.51 | |
| 2 | Calpain Inhibitor I (ALLN, Ac-LLnL-CHO, MG-101) | | 383.53 | Cathepsin B Cathepsin L Calpine Proteasome |

TABLE 27

Chymotrypsin inhibitor

| No. | Name | Structural formula | Molecular weight | Protease to be inhibited |
|---|---|---|---|---|
| 1 | Diisopropyl-fluoro-phosphate | | 184.15 | Carboxypeptidase Chymotrypsin Complement Elastase Endoproteinase Kallikrein Plasmin Thrombin Pronase Proteinase |

TABLE 27-continued

Chymotrypsin inhibitor

| No. | Name | Structural formula | Molecular weight | Protease to be inhibited |
|---|---|---|---|---|
| 2 | 4-(2-Aminoethyl) benzene-sulfonyl fluoride hydrochloride (AEBSF) | | 239.69 | Plasmin<br>Trypsin<br>Chymotrypsin |
| 3 | 6-Amino-caproic acid | | 131.17 | |
| 4 | Chymostatin | Chymostatin A X = Leu<br>Chymostatin B X = Val<br>Chymostatin C X = Ile | A: MW = 607.7<br>B: MW = 593.7<br>C: MW = 607.7 | Chymotrypsin<br>Papain<br>Chymotrypsin-like serine proteinase<br>Cathepsin A, B, C, B, H, L<br>Proteasome (β5) |

TABLE 28

Chymotrypsin inhibitor

| No. | Name | Structural formula | Molecular weight | Protease to be inhibited |
|---|---|---|---|---|
| 1 | N-p-Tosyl-L-phenyl-alanine chloromethyl ketone | | 351.85 | Papain<br>Chymotrypsin<br>Ficin<br>Bromelain |
| 2 | Bromoenol lactone | | 317.18 | |

TABLE 28-continued

| | | Chymotrypsin inhibitor | | |
|---|---|---|---|---|
| No. | Name | Structural formula | Molecular weight | Protease to be inhibited |
| 3 | Gabexate mesylate | 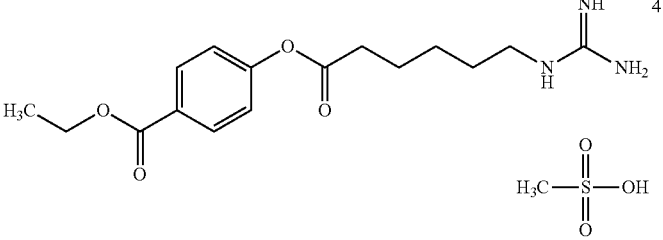 | 417.48 | |
| 4 | Leupeptin | 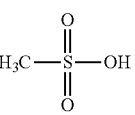 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 29

| | | Clostripain inhibitor | | |
|---|---|---|---|---|
| No. | Name | Structural formula | Molecular weight | Protease to be inhibited |
| 1 | 4-Chloromercuri-benzoic acid | 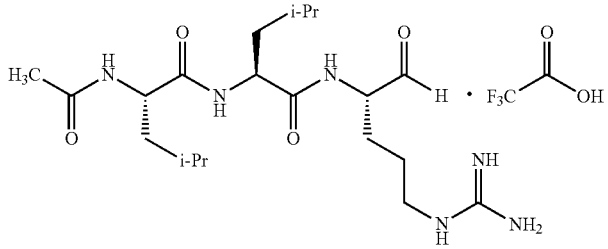 | 357.16 | Calpine<br>Carboxypeptidase<br>Clostripain |
| 2 | Nα-Tosyl-L-lysine chloromethyl ketone hydrochloride | 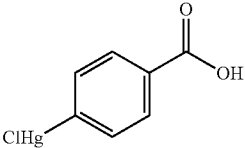 | 369.31 | |

TABLE 30

| | | Collagenase inhibitor | | |
|---|---|---|---|---|
| No. | Name | Structural formula | Molecular weight | Protease to be inhibited |
| 1 | EDTA disodium salt | 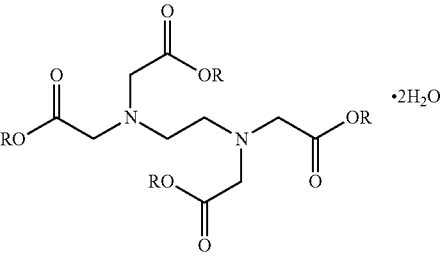 R = H or Na (2:2) | 372.24 | Carboxypeptidase A<br>Carboxypeptidase B<br>Dispase<br>Collagenase |
| 2 | Dichloro-methylene diphosphonic acid disodium salt (DMDP) | 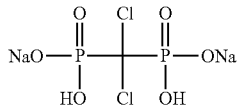 | 288.86 | |

TABLE 31

| | | Complement C1r/C1s inhibitor | | |
|---|---|---|---|---|
| No. | Name | Structural formula | Molecular weight | Protease to be inhibited |
| 1 | Diisopropyl-fluorophosphate | 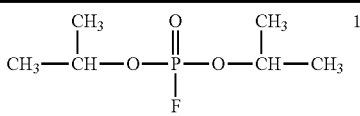 | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 32

| | | Complement factor D/B inhibitor | | |
|---|---|---|---|---|
| No. | Name | Structural formula | Molecular weight | Protease to be inhibited |
| 1 | Diisopropyl-fluorophosphate | 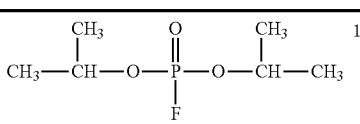 | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 33

Dipeptidyl peptidase II inhibitor

| No. | Name | Structural formula | Molecular weight | Protease to be inhibited |
|---|---|---|---|---|
| 1 | Puromycin | [structure] | 471.51 | Dipeptidyl peptidase II Cytosol alanyl aminopeptidase |

TABLE 34

Dipeptidyl peptidase III inhibitor

| No. | Name | Structural formula | Molecular weight | Protease to be inhibited |
|---|---|---|---|---|
| 1 | Opiorphin | [structure] | 692.77 | Enkephalinase Neprilysin Dipeptidyl peptidase III Cytosol alanyl aminopeptidase |

TABLE 35

Dipeptidyl peptidase IV inhibitor

| No. | Name | Structural formula | Molecular weight | Protease to be inhibited |
|---|---|---|---|---|
| 1 | Ile-Pro-Ile | [structure] | 341.45 | Dipeptidyl peptidase IV |

TABLE 36

Dispase inhibitor

| No. | Name | Structural formula | Molecular weight | Protease to be inhibited |
|---|---|---|---|---|
| 1 | EDTA disodium salt | (EDTA structure) R = H or Na (2:2) ·2H$_2$O | 372.24 | Carboxypeptidase A<br>Carboxypeptidase B<br>Dispase<br>Collagenase |
| 2 | 1,10-Phenanthroline monohydrate | (1,10-phenanthroline structure) ·H$_2$O | 198.22 | Carboxypeptidase A<br>Carboxypeptidase B<br>Dispase<br>Leucine aminopeptidase<br>Thermolysin |

TABLE 37

Elastase (granulocyte) inhibitor

| No. | Name | Structural formula | Molecular weight | Protease to be inhibited |
|---|---|---|---|---|
| 1 | N-(Methoxy-succinyl)-Ala-Ala-Pro-Val-chloromethyl ketone | H$_3$CO–(C=O)–CH$_2$CH$_2$–(C=O)–Ala-Ala-Pro-Val–CH$_2$Cl | 502.99 | |

TABLE 38

Elastase (leukocyte) inhibitor

| No. | Name | Structural formula | Molecular weight | Protease to be inhibited |
|---|---|---|---|---|
| 1 | Diisopropyl-fluoro-phosphate | CH$_3$–CH(CH$_3$)–O–P(=O)(F)–O–CH(CH$_3$)–CH$_3$ | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 3,4-Dichloro-isocoumarin | (3,4-dichloroisocoumarin structure) | 215.03 | Thrombin<br>Papain<br>Plasmin |

TABLE 38-continued

| | | Elastase (leukocyte) inhibitor | | |
|---|---|---|---|---|
| No. | Name | Structural formula | Molecular weight | Protease to be inhibited |
| 3 | Phenyl-methane-sulfonyl fluoride | [structure: benzyl-SO₂-F] | 174.19 | Thrombin Elastase Plasmin Proteinase |

TABLE 39

| | | Elastase (pancreas) inhibitor | | |
|---|---|---|---|---|
| No. | Name | Structural formula | Molecular weight | Protease to be inhibited |
| 1 | Diisopropyl-fluoro-phosphate | CH₃—CH(CH₃)—O—P(=O)(F)—O—CH(CH₃)—CH₃ | 184.15 | Carboxypeptidase Chymotrypsin Complement Elastase Endoproteinase Kallikrein Plasmin Thrombin Pronase Proteinase |
| 2 | 3,4-Dichloro-isocoumarin | [structure: 3,4-dichloroisocoumarin] | 215.03 | Thrombin Papain Plasmin |

TABLE 40

| | | Endoproteinase Arg-C inhibitor | | |
|---|---|---|---|---|
| No. | Name | Structural formula | Molecular weight | Protease to be inhibited |
| 1 | Diisopropyl-fluorophosphate | CH₃—CH(CH₃)—O—P(=O)(F)—O—CH(CH₃)—CH₃ | 184.15 | Carboxypeptidase Chymotrypsin Complement Elastase Endoproteinase Kallikrein Plasmin Thrombin Pronase Proteinase |
| 2 | 3,4-Dichloro-isocoumarin | [structure: 3,4-dichloroisocoumarin] | 215.03 | Thrombin Papain Plasmin |

TABLE 41

Endoproteinase Glu-C inhibitor

| No. | Name | Structural formula | Molecular weight | Protease to be inhibited |
|---|---|---|---|---|
| 1 | Diisopropyl-fluoro-phosphate | 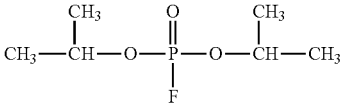 | 184.15 | Carboxypeptidase Chymotrypsin Complement Elastase Endoproteinase Kallikrein Plasmin Thrombin Pronase Proteinase |

TABLE 42

Endoproteinase Lys-C inhibitor

| No. | Name | Structural formula | Molecular weight | Protease to be inhibited |
|---|---|---|---|---|
| 1 | Diisopropyl-fluoro-phosphate | 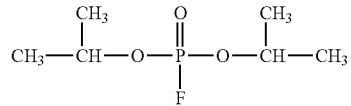 | 184.15 | Carboxypeptidase Chymotrypsin Complement Elastase Endoproteinase Kallikrein Plasmin Thrombin Pronase Proteinase |
| 2 | 3,4-Dichloro-isocoumarin | 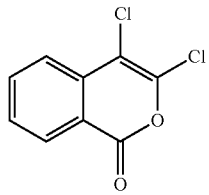 [SMILES: O=c1oc(Cl)c(Cl)c2ccccc12] | 215.03 | Thrombin Papain Plasmin |
| 3 | Leupeptin | 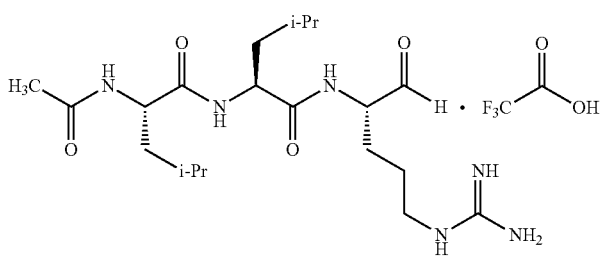 [SMILES: CC(=O)N[C@@H](CC(C)C)C(=O)N[C@@H](CC(C)C)C(=O)N[C@H](C=O)CCCNC(=N)N ; O=C(O)C(F)(F)F] | 426.55 | Plasmin Trypsin Papain Calpine Cathepsin B Thrombin Kellikrein Endoproteinase Chymotrypsin Proteasome (β2) |

TABLE 43

Ficin inhibitor

| No. | Name | Structural formula | Molecular weight | Protease to be inhibited |
|---|---|---|---|---|
| 1 | E-64 | | 357.41 | Cathepsin B<br>Ficin<br>Papein<br>Bromelain |
| 2 | N-Ethyl-maleimide | | 125.13 | Calpine<br>Ficin |
| 3 | N-p-Tosyl-L-phenilalanine chloromethyl ketone | | 351.85 | Papain<br>Chymotrypsin<br>Ficin<br>Bromelain |
| 4 | Sodium iodoactate | | 207.93 | Carboxypeptidase P<br>Bromelain<br>Ficin<br>Cathepsin |
| 5 | Nα-Tosyl-L-lysine chloromethyl ketone hydrochloride | | 369.31 | |

TABLE 44

Granzyme B inhibitor

| No. | Name | Structural formula | Molecular weight | Protease to be inhibited |
|-----|------|--------------------|------------------|--------------------------|
| 1 | Antipain-dihydrochloride from microbial source | (structure shown) ·2HCl | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 2 | 3,4-Dichloro-isocoumarin | (structure shown) | 215.03 | Thrombin<br>Papain<br>Plasmin |

TABLE 45

Kallikrein (tissue) inhibitor

| No. | Name | Structural formula | Molecular weight | Protease to be inhibited |
|-----|------|--------------------|------------------|--------------------------|
| 1 | Diisopropyl-fluoro-phosphate | $CH_3-CH(CH_3)-O-P(=O)(F)-O-CH(CH_3)-CH_3$ | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 3,4-Dichloro-isocoumarin | (structure shown) | 215.03 | Thrombin<br>Papain<br>Plasmin |
| 3 | Leupeptin | (structure shown) · $F_3C$-COOH | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 46

Kallikrein (plasma) inhibitor

| No. | Name | Structural formula | Molecular weight | Protease to be inhibited |
|---|---|---|---|---|
| 1 | Gabexate mesylate | | 417.48 | |

TABLE 47

Leucine aminopeptidase inhibitor

| No. | Name | Structural formula | Molecular weight | Protease to be inhibited |
|---|---|---|---|---|
| 1 | Actinonin | | 385.5 | |
| 2 | Bestatin hydrochloride | | 344.83 | Aminopeptidase B |

TABLE 48

Leucine aminopeptidase (cytosol) inhibitor

| No. | Name | Structural formula | Molecular weight | Protease to be inhibited |
|---|---|---|---|---|
| 1 | Actinonin | | 385.5 | |

TABLE 48-continued

Leucine aminopeptidase (cytosol) inhibitor

| No. | Name | Structural formula | Molecular weight | Protease to be inhibited |
|---|---|---|---|---|
| 2 | Amastatin hydrochloride hydrate | 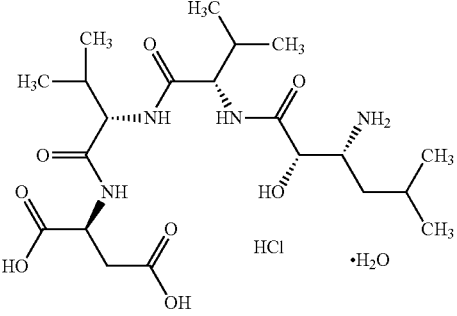 [SMILES: CC(C)C[C@@H](N)[C@H](O)C(=O)N[C@H](C(=O)N[C@H](C(=O)N[C@@H](CC(=O)O)C(=O)O)C(C)C)C(C)C ; Cl ; O] | 511.01 (anhydrous basis) | |
| 3 | Ethylene glycol-bis(2-aminoethyl ether)-N,N,N',N'-tetraacetic acid | 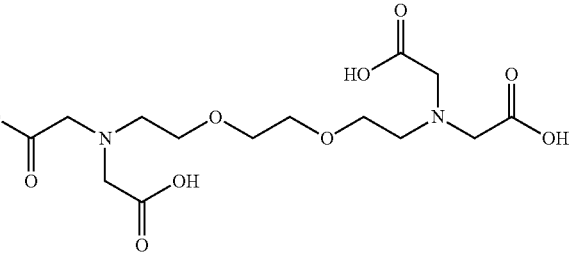 | 380.35 | |
| 4 | Ethylenediaminetetraacetic acid disodium salt dihydrate | 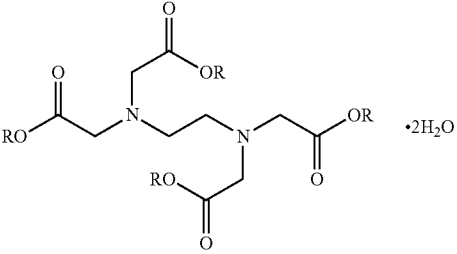<br>R = H or Na (2:2) | 372.24 | |

TABLE 49

Leucine aminopeptidase (cytosol) inhibitor (Continued)

| No. | Name | Structural formula | Molecular weight | Protease to be inhibited |
|---|---|---|---|---|
| 5 | Diethylene triaminepentaacetic acid | 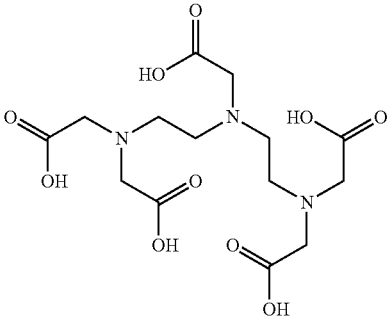 [SMILES: O=C(O)CN(CCN(CC(=O)O)CC(=O)O)CCN(CC(=O)O)CC(=O)O] | 393.35 | |

TABLE 49-continued

Leucine aminopeptidase (cytosol) inhibitor (Continued)

| No. | Name | Structural formula | Molecular weight | Protease to be inhibited |
|---|---|---|---|---|
| 6 | 3,4-Dichloro-isocoumarin | | 215.03 | Thrombin<br>Papain<br>Plasmin |
| 7 | 1,10-Phenanthroline monohydrate | | 198.22 | Carboxypeptidase A<br>Carboxypeptidase B<br>Dispase<br>Leucine aminopeptidase<br>Thermolysin |
| 8 | Bestatin hydrochloride | | 344.83 | AminopeptidaseB |

TABLE 50

Leucine aminopeptidase (microsome) inhibitor

| No. | Name | Structural formula | Molecular weight | Protease to be inhibited |
|---|---|---|---|---|
| 1 | Actinonin | | 385.5 | |
| 2 | Amastatin hydrochloride hydrate | | 511.01 (anhydrous basis) | |

TABLE 50-continued

Leucine aminopeptidase (microsome) inhibitor

| No. | Name | Structural formula | Molecular weight | Protease to be inhibited |
|---|---|---|---|---|
| 3 | Bestatin hydrochloride | 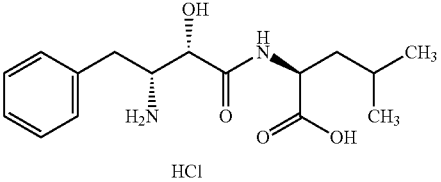 [SMILES: CC(C)C[C@H](NC(=O)[C@@H](O)[C@H](N)Cc1ccccc1)C(=O)O ; Cl] | 344.83 | Aminopeptidase B |

TABLE 51

Matrix aminopeptidase inhibitor

| No. | Name | Structural formula | Molecular weight | Protease to be inhibited |
|---|---|---|---|---|
| 1 | GM6001 | 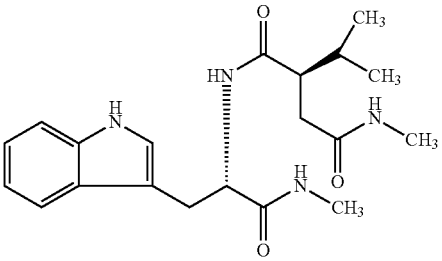 [SMILES: CNC(=O)C[C@@H](C(=O)N[C@@H](Cc1c[nH]c2ccccc12)C(=O)NC)C(C)C] | 388.46 | |

TABLE 52

Metalloprotease inhibitor

| No. | Name | Structural formula | Molecular weight | Protease to be inhibited |
|---|---|---|---|---|
| 1 | Epiamastatin hydrochloride | 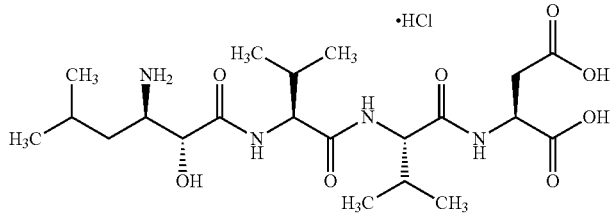 [SMILES: CC(C)C[C@@H](N)[C@@H](O)C(=O)N[C@H](C(=O)N[C@H](C(=O)N[C@@H](CC(=O)O)C(=O)O)C(C)C)C(C)C ; Cl] | 474.55 | |

TABLE 53
| | | Papain inhibitor | | |
|---|---|---|---|---|
| No. | Name | Structural formula | Molecular weight | Protease to be inhibited |
| 1 | E-64 | 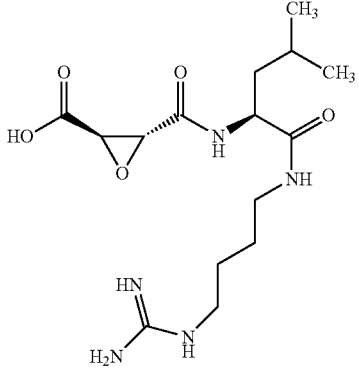 [SMILES: CC(C)C[C@H](NC(=O)[C@@H]1O[C@H]1C(=O)O)C(=O)NCCCCNC(=N)N] | 357.41 | |
| 2 | Gly-Gly-Tyr-Arg | 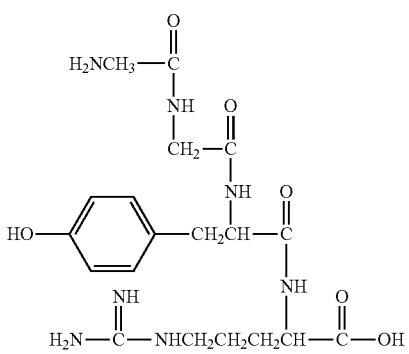 | 451.48 | |
| 3 | Antipain dihydrochloride from microbial source | 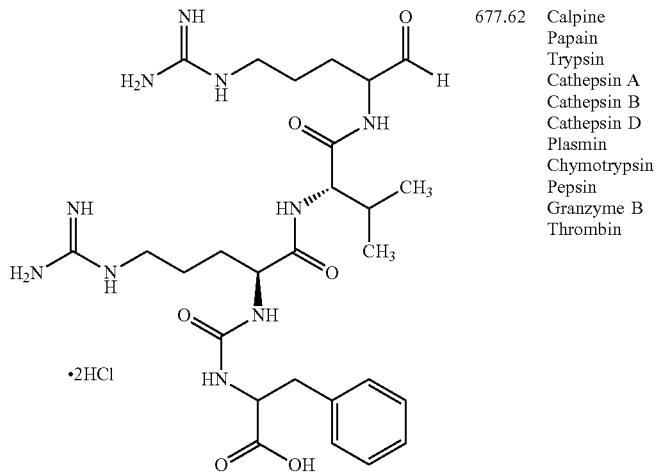 | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 4 | Ebselen | 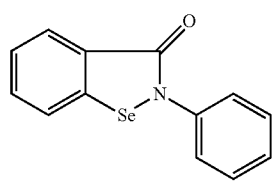 [SMILES: O=c1c2ccccc2[se]n1-c1ccccc1] | 274.18 | |

TABLE 54

Papain inhibitor (Continued)

| No. | Name | Structural formula | Molecular weight | Protease to be inhibited |
|---|---|---|---|---|
| 5 | Chymostatin | (structure shown)<br>Chymostatin A  X = Leu<br>Chymostatin B  X = Val<br>Chymostatin C  X = Ile | A: MW= 607.7<br>B: MW = 593.7<br>C: MW = 607.7 | Chymotrypsin<br>Papain<br>Chymotrypsin-like serine proteinase<br>Cathepsin A, B,C, B, H, L<br>Proteasome (β5) |
| 6 | Cystamine dihydrochloride | (structure shown) ·2HCl | 225.2 | |
| 7 | 3,4-Dichloroisocoumarin | (structure shown) | 215.03 | Thrombin<br>Papain<br>Plasmin |
| 8 | N-p-Tosyl-L-phenilalanine chloromethyl ketone | (structure shown) | 351.85 | Papain<br>Chymotrypsin<br>Ficin<br>Bromelain |
| 9 | Leupeptin | (structure shown) | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 55

Pepsin inhibitor

| No. | Name | Structural formula | Molecular weight | Protease to be inhibited |
|---|---|---|---|---|
| 1 | Pepstatin A | (structure shown) | 685.89 | Cathepsin D |

TABLE 56

| | | Plasmin inhibitor | | |
|---|---|---|---|---|
| No. | Name | Structural formula | Molecular weight | Protease to be inhibited |
| 1 | Diisopropyl-fluoro-phosphate | 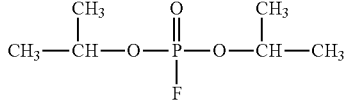 | 184.15 | Carboxypeptidase Chymotrypsin Complement Elastase Endoproteinase Kallikrein Plasmin Thrombin Pronase Proteinase |
| 2 | Elastatinal | 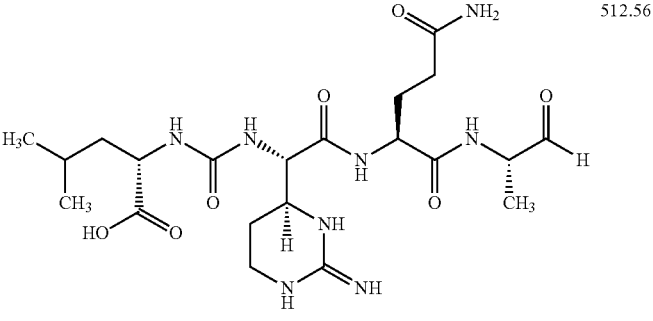 | 512.56 | |
| 3 | 4-(2-Aminoethyl)benzenesulfonyl fluoride hydrochloride (AEBSF) | 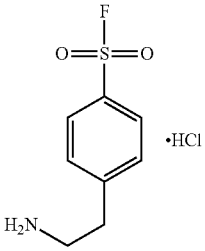 | 239.69 | Plasmin Trypsin Chymotrypsin |
| 4 | 6-Aminocaproic acid | 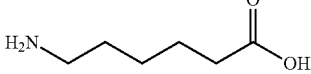 | 131.17 | |
| 5 | Antipain dihydrochloride from microbial source | 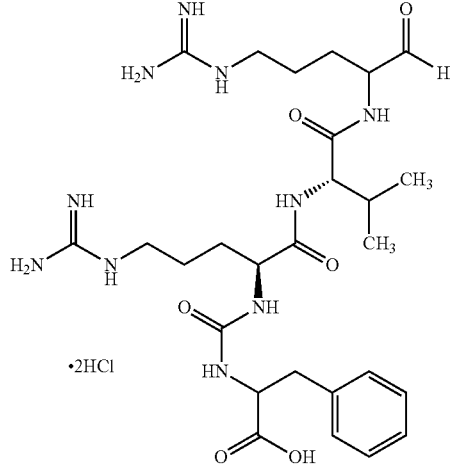 [SMILES: CC(C)[C@H](NC(=O)[C@H](CCCNC(=N)N)NC(=O)NC(Cc1ccccc1)C(=O)O)C(=O)NC(C=O)CCCNC(=N)N] | 677.62 | Calpine Papain Trypsin Cathepsin A Cathepsin B Cathepsin D Plasmin Chymotrypsin Pepsin Granzyme B Thrombin |

TABLE 57

Plasmin inhibitor (Continued)

| No. | Name | Structural formula | Molecular weight | Protease to be inhibited |
|---|---|---|---|---|
| 6 | 3,4-Dichloroisocoumarin | | 215.03 | Thrombin<br>Papain<br>Plasmin |
| 7 | Phenylmethanesulfonyl fluoride | | 174.19 | Thrombin<br>Elastase<br>Plasmin<br>Proteinase |
| 8 | Gabexate mesylate | | 417.48 | |
| 9 | Leupeptin | | 426.55 | Plasmin<br>Trypsin<br>Papain<br>Calpine<br>Cathepsin B<br>Thrombin<br>Kallikrein<br>Endoproteinase<br>Chymotrypsin<br>Proteasome ($\beta$2) |

TABLE 58

Thrombin inhibitor

| No. | Name | Structural formula | Molecular weight | Protease to be inhibited |
|---|---|---|---|---|
| 1 | Diisopropyl-fluorophosphate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | N$\alpha$-Tosyl-L-lysine chloromethyl ketone hydrochloride | | 369.31 | |

TABLE 58-continued

Thrombin inhibitor

| No. | Name | Structural formula | Molecular weight | Protease to be inhibited |
|---|---|---|---|---|
| 3 | 4-(2-Aminoethyl) benzenesulfonyl fluoride hydrochloride (AEBSF) | | 239.69 | |
| 4 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin |

TABLE 59

Thrombin inhibitor (Continued)

| No. | Name | Structural formula | Molecular weight | Protease to be inhibited |
|---|---|---|---|---|
| 5 | 3,4-Dichloroisocoumarin | | 215.03 | Thrombin<br>Papain<br>Plasmin |
| 6 | Phenylmethanesulfonyl fluoride | | 174.19 | Thrombin<br>Elastase<br>Plasmin<br>proteinase |
| 7 | Gabexate mesylate | | 417.48 | |

TABLE 59-continued

Thrombin inhibitor (Continued)

| No. | Name | Structural formula | Molecular weight | Protease to be inhibited |
|---|---|---|---|---|
| 8 | Leupeptin | (structure shown) · F₃C-COOH | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 60

Thermolysin inhibitor

| No. | Name | Structural formula | Molecular weight | Protease to be inhibited |
|---|---|---|---|---|
| 1 | Ethylene glycol-bis(2-aminoethyl ether)-N,N,N',N'-tetraacetic acid | (structure shown) | 380.35 | |
| 2 | Ethylenediaminetetraacetic acid disodium salt dihydrate | (structure shown) ·2H₂O<br>R = H or Na (2:2) | 372.24 | Carboxypeptidase A<br>Carboxypeptidase B<br>Dispase<br>Collagenase |
| 3 | Diethylene triaminepentaacetic acid | (structure shown) | 393.35 | |
| 4 | 1,10-Phenanthroline monohydrate | (structure shown) ·H₂O | 198.22 | Carboxypeptidase A<br>Carboxypeptidase B<br>Dispase<br>Leucine aminopeptidase<br>Thermolysin |

TABLE 60-continued

Thermolysin inhibitor

| No. | Name | Structural formula | Molecular weight | Protease to be inhibited |
|---|---|---|---|---|
| 5 | Phosphoramidon disodium salt | (structure shown) | 567.47 | |

TABLE 61

Trypsin inhibitor

| No. | Name | Structural formula | Molecular weight | Protease to be inhibited |
|---|---|---|---|---|
| 1 | 4-(2-Aminoethyl) benzenesulfonyl fluoride hydrochloride | (structure shown) | 239.69 | Plasmin<br>Trypsin<br>Chymotrypsin |
| 2 | Antipain dihydrochloride from microbial source | (structure shown) | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 3 | Boldine | (structure shown) | 327.37 | |

TABLE 62

Pronase E inhibitor

| No. | Name | Structural formula | Molecular weight | Protease to be inhibited |
|---|---|---|---|---|
| 1 | EDTA disodium salt | 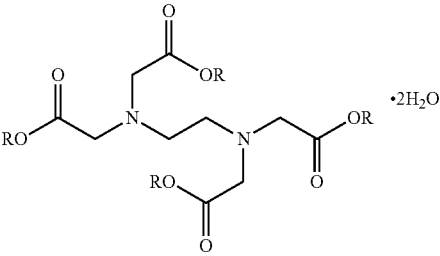 R = H or Na (2:2) | 372.24 | Carboxypeptidase A<br>Carboxypeptidase B<br>Dispase<br>Collagenase |
| 2 | Diisopropyl-fluorophosphate | 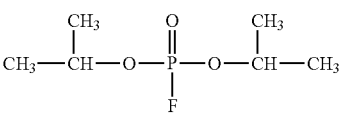 | 184.15 | Carboxypeptidase<br>Chymotrypsin<br>Complement<br>Elastase<br>Encloproteinase<br>Kallikrein<br>Plasmin<br>Thrombin<br>Pronase<br>Proteinase |

TABLE 63

Procaspase 3 inhibitor

| No. | Name | Structural formula | Molecular weight | Protease to be inhibited |
|---|---|---|---|---|
| 1 | N-Acetyl-Glu-Ser-Met-Asp-al (Ac-ESMD-CHO) | 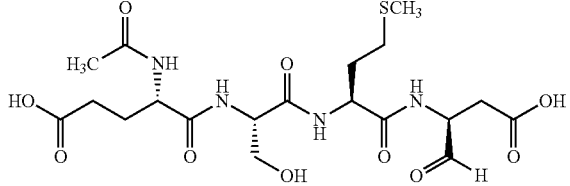 [SMILES: CSCC[C@H](NC(=O)[C@H](CO)NC(=O)[C@H](CCC(=O)O)NC(C)=O)C(=O)N[C@H](C=O)CC(=O)O] | 506.53 | |
| 2 | N-Acetyl-Ile-Glu-Thr-Asp-al (Ac-IETD-CHO) | 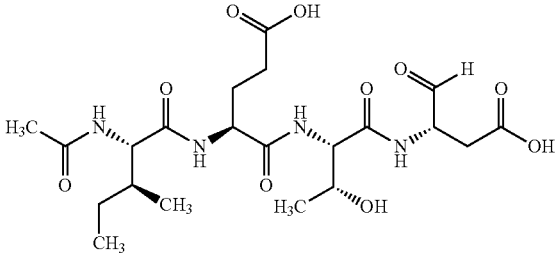 [SMILES: CC[C@H](C)[C@H](NC(C)=O)C(=O)N[C@@H](CCC(=O)O)C(=O)N[C@H](C(=O)N[C@H](C=O)CC(=O)O)[C@@H](C)O] | 502.52 | |

TABLE 64

Proteinase K inhibitor

| No. | Name | Structural formula | Molecular weight | Protease to be inhibited |
|---|---|---|---|---|
| 1 | Phenylmethane-sulfonyl fluoride | 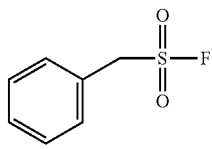 [SMILES: O=S(=O)(F)Cc1ccccc1] | 174.19 | Thrombin<br>Elastase<br>Plasmin<br>Proteinase |

TABLE 64-continued

Proteinase K inhibitor

| No. | Name | Structural formula | Molecular weight | Protease to be inhibited |
|-----|------|--------------------|------------------|---------------------------|
| 2 | Diisopropyl-fluorophosphate | (CH₃)₂CH—O—P(=O)(F)—O—CH(CH₃)₂ | 184.15 | Carboxypeptidase Chymotrypsin Complement Elastase Endoproteinase Kallikrein Plasmin Thrombin Pronase Proteinase |

TABLE 65

Renin inhibitor

| No. | Name | Structural formula | Molecular weight | Protease to be inhibited |
|-----|------|--------------------|------------------|---------------------------|
| 1 | Pepstatin A | [structure] | 685.89 | Cathepsin D |

TABLE 66

Caspase inhibitor

| No. | Name | Structural formula | Molecular weight | Protease to be inhibited |
|-----|------|--------------------|------------------|---------------------------|
| 1 | Boc-Asp(OMe)-fluoromethyl ketone (Boc-D-FMK) | [structure] | 263.26 | |
| 2 | Z-Ala-Glu(OMe)-Val-Asp(OMe)-fluoromethyl ketone (Z-AEVD-FMK) | [structure] | 610.63 | |

TABLE 67

Caspase 1 inhibitor

| No. | Name | Structural formula | Molecular weight | Protease to be inhibited |
|---|---|---|---|---|
| 1 | N-Acetyl-Trp-Glu-His-Asp-al (Ac-WEHD-CHO) | | 611.6 | |

TABLE 68

Caspase 2 inhibitor

| No. | Name | Structural formula | Molecular weight | Protease to be inhibited |
|---|---|---|---|---|
| 1 | N-Acetyl-Val-Asp-Val-Ala-Asp-CHO (Ac-VDVAD-CHO) | | 543.52 | |
| 2 | Z-Val-Asp(O—Me)-Val-Ala-Asp(O—Me) fluoromethyl ketone(Z-VDVAD-FMK) | | 695.73 | |

TABLE 69

Caspase 3 inhibitor

| No. | Name | Structural formula | Molecular weight | Protease to be inhibited |
|---|---|---|---|---|
| 1 | N-Acetyl-Gly-Ser-Met-Asp-al (Ac-ESMD-CHO) | | 506.53 | |

TABLE 69-continued

Caspase 3 inhibitor

| No. | Name | Structural formula | Molecular weight | Protease to be inhibited |
|---|---|---|---|---|
| 2 | Z-Asp(OMe)-Gln-Met-Asp(OMe) fluoromethyl ketone | | 685.72 | |
| 3 | N-Acetyl-Asp-Glu-Val-Asp-al (Ac-DEVD-CHO) | | 502.47 | |
| 4 | N-Acetyl-Ile-Glu-Thr-Asp-al (Ac-IETD-CHO) | | 502.52 | |

TABLE 70

Caspase 5 inhibitor

| No. | Name | Structural formula | Molecular weight | Protease to be inhibited |
|---|---|---|---|---|
| 1 | N-Acetyl-Trp-Glu-His-Asp-al (Ac-WEHD-CHO) | | 611.6 | |

TABLE 71

Casepase 6 inhibitor

| No. | Name | Structural formula | Molecular weight | Protease to be inhibited |
|---|---|---|---|---|
| 1 | N-Acetyl-Val-Glu-Ile-Asp-al | | 500.54 | |
| 2 | Z-Asp(OMe)-Gln-Met-Asp(OMe) fluoromethyl ketone | | 685.72 | |
| 3 | Z-Val-Glu(O—Me)-Ile-Asp(O—Me) fluoromethyl ketone (Z-DEVD-FMK) | | 652.71 | |

TABLE 72

Caspase 7 inhibitor

| No. | Name | Structural formula | Molecular weight | weight inhibited |
|---|---|---|---|---|
| 1 | Z-Asp(O—Me)-Glu(O—Me)-Val-Asp(O—Me) fluoeomethyl ketone (Z-DEVD-FMK) | | 668.66 | |

TABLE 73

Casepase 8 inhibitor

| No. | Name | Structural formula | Molecular weight | Protease to be inhibited |
|---|---|---|---|---|
| 1 | Z-Ile-Glu(O—Me)-Thr-Asp(O—Me) fluoromethyl ketone (Z-IETO-FMK) | | 654.68 | |
| 2 | Z-Leu-Glu(OMe)-Thr-Asp(OMe)-fluoromethyl ketone (Z-LETD-FMK) | | 655.69 | |
| 3 | N-Acetyl-Ile-Glu-Thr-Asp-al (Ac-IETD-CHO) | | 502.52 | |

TABLE 74

Caspase 9 inhibitor

| No. | Name | Structural formula | Molecular weight | Protease to be inhibited |
|---|---|---|---|---|
| 1 | Z-Leu-Glu(O—Me)-His-Asp(O—Me) fluoromethyl ketone (Z-LE(OMe)HD(OMe)-FMK, Z-LEHD-FMK) | | 690.72 | |

TABLE 75

Caspase 13 inhibitor

| No. | Name | Structural formula | Molecular weight | Protease to be inhibited |
|---|---|---|---|---|
| 1 | Z-Leu-Glu(OMe)-Glu(OMe)-Asp(OMe)-fluoromethyl ketone (Z-LEED-FMK) | | 696.72 | |

TABLE 76

Cytosol alanyl aminopeptidase inhibitor

| No. | Name | Structural formula | Molecular weight | Protease to be inhibited |
|---|---|---|---|---|
| 1 | Puroycin | | 471.51 | Dipeptidyl peptidase II<br>Cytosol alanyl aminopeptidase |
| 2 | Opiorphin | | 692.77 | Enkephalinase<br>Neprilysin<br>Dipeptidyl peptidase III<br>Cytosol alanyl aminopeptidase |

TABLE 77

Enkephalinase inhibitor

| No. | Name | Structural formula | Molecular weight | Protease to be inhibited |
|-----|------|-------------------|------------------|--------------------------|
| 1 | Opiorphin | (structure) | 692.77 | Enkephalinase<br>Neprilysin<br>Dipeptidyl peptidase III<br>Cytosol alanyl aminopeptidase |

TABLE 78

Nephrilysin inhibitor

| No. | Name | Structural formula | Molecular weight | Protease to be inhibited |
|-----|------|-------------------|------------------|--------------------------|
| 1 | Opiorphin | (structure) | 692.77 | Enkephalinase<br>Neprilysin<br>Dipeptidyl peptidase III<br>Cytosol alanyl aminopeptidase |

It is noted that in the above descriptions, proteasome inhibitors and protease inhibitors other than the proteasome inhibitors are separately discussed for convenience, but a compound is also known which can inhibit the activities of both a proteasome and a protease other than proteasomes. Therefore, a protein-degradation inducing tag having an affinity with both a proteasome and a protease other than proteasomes can be obtained when such a compound is used.

Examples of the compound which can inhibit the activities of both a proteasome and a protease other than proteasomes are shown in the following table 79. In Example 10 described below, the protein-degradation inducing tag is used in which the protease (proteasome) inhibitory activity of a calpain inhibitor (ALLN) shown in No. 1 of Table 79 is inactivated. However, the compound which can inhibit the activities of both a proteasome and a protease other than proteasomes shall not be limited to these examples.

TABLE 79

| No. | Name | Structural formula | Molecular weight | Protease to be inhibited |
|---|---|---|---|---|
| 1 | Calpain Inhibitor I (ALLN, Ac-LLnL-CHO, MG-101) | | 383.53 | Proteasome Cathepsin B Cathepsin L Calpine |
| 2 | Calpain Inhibitor II | | 401.56 | Proteasome Cathepsin B Calpine |
| 3 | Leupeptin | | 426.55 | Plasmin Trypsin Papain Calpine Cathepsin B Thrombin Kallikrein Endoproteinase Chymotrypsin Proteasome ($\beta$2) |
| 4 | Chymostatin | Chymostatin A X = Leu<br>Chymostatin B X = Val<br>Chymostatin C X = Ile | A: MW = 607.47<br>B: MW = 593.7<br>C: MW = 607.7 | Proteasome ($\beta$5) Chymotrypsin Papain Chymotrypsin-like serine proteinase Cathepsin A, B, C, B, H, L |
| 5 | clasto-Lactacystin $\beta$-lactone | | 213.23 | tripeptidyl peptidase II chlamydial protease-like activity factor |

In another embodiment, a proteasome activator can be used as a protein-degradation inducing tag. A proteasome activator is a compound having an affinity with a proteasome (a protease complex) without inhibiting degradation of a protein by the proteasome, and can be used as a protein-degradation inducing tag. That is, according to the present disclosure, use of a proteasome activator as a protein-degradation inducing tag is provided.

Examples of the proteasome activator are shown in the following Tables 80 to 82. However, the proteasome activator which can be used in the present embodiment shall not be limited to these examples.

TABLE 80

| No. | Generic name/Product name | Structural formula | Molecular weight |
|---|---|---|---|
| 1 | Oleuropein | | 540.51 |
| 2 | Betulinic acid | | 456.70 |

TABLE 81

19s/11s (PA28) proteasome activator

| No. | Generic name/Product name | Structural formula | Molecular weight |
|---|---|---|---|
| 1 | IU1 (Usp 14 inhibitor) | | 300.38 |
| 2 | b-AP-15 (Usp 14 and Uch-L5 inhibitor) | | 419.39 |

TABLE 81-continued

19s/11s (PA28) proteasome activator

| No. | Generic name/ Product name | Structural formula | Molecular weight |
|---|---|---|---|
| 3 | 17-AAG | | 585.7 |
| 4 | PU3 | | 371.44 |
| 5 | PU-H71 | | 512.37 |
| 6 | NVP-AUY922 | | 493.60 |

TABLE 82

19s/11s (PA28) proteasome activator (Continued)

| No. | Generic name/Product name | Structural formula | Molecular weight |
|-----|---------------------------|--------------------|------------------|
| 7 | SNX-5422 | | 521.54 |
| 8 | HBX 19,818 | | 407.94 |
| 9 | LS1 | | 518.53 |
| 10 | LDN91946 | | 314.32 |
| 11 | P005091 | | 348.21 |
| 12 | P0040429 | | 484.38 |

Method of Screening for Protein-Degradation Inducing Tag

The method of screening for a protein-degradation inducing tag according to the present disclosure includes a step of selecting a molecule having an affinity with a protease without inhibiting degradation of a protein by the protease from candidate molecules. In a certain embodiment, the protease is a proteasome (a protease complex).

There is no particular limitation for a method of selecting, from candidate molecules, a molecule having an affinity with a protease without inhibiting degradation of a protein by the protease, but, for example, the following method may be used.

First, candidate molecules are prepared. As the candidate molecules, a library can be used such as a compound library, a drug library, and a natural-product library. The candidate molecules are preferably pre-immobilized on each well of a plate for high throughput screening (HTS), a microarray plate, a metal plate, and the like.

Next, the candidate molecules immobilized on each well are subjected to treatment with a protease labelled with a fluorochrome, nucleic acid (mRNA or DNA), or the like, and then each well is washed. In order to label a protease with a fluorochrome, a fusion protein with GFP (Green Fluorescent Protein), labelling by C-terminus labeling, and the like can be used. In order to label a protease with nucleic acid, a display method can be used such as the IVV (in vitro virus) method (may also be referred to as the mRNA display method) and the DNA display method. Then, a molecule having an affinity with a protease will be specified based on the label on a protease. When a protease is labelled with a fluorochrome, a molecule having an affinity with the protease can be specified by detecting fluorescence. When a protease is labelled with mRNA, a molecule having an affinity with the protease can be specified by detecting the sequence of the nucleic acid by reverse transcription PCR.

Next, a molecule which does not inhibit degradation of a protein by the protease will be specified from molecules having an affinity with the protease. To evaluate whether degradation of a protein by a protease is inhibited or not, a method can be use which is described in Example below.

Method of Manufacturing Protein-Degradation Inducing Tag

The method of manufacturing a protein-degradation inducing tag according to the present disclosure includes a step of modifying a structure of an active site of a protease inhibitor to inactivate the protease inhibitory activity. In a certain embodiment, the protease inhibitor is a proteasome inhibitor, and a protein-degradation inducing tag is manufactured by inactivating the proteasome inhibitory activity of the proteasome inhibitor.

As described above, the protease inhibitor is a compound having an affinity with a protease and inhibiting degradation of a protein by the protease. Therefore, a protein-degradation inducing tag can be obtained by modifying structure of the active site of a protease inhibitor to inactivate the protease inhibitory activity.

The protease inhibitor used for manufacturing a protein-degradation inducing tag may be a known protease inhibitor, or may be obtained by screening candidate molecules. That is, the method of manufacturing a protein-degradation inducing tag may further include a step of selecting, as a protease inhibitor, a molecule having an affinity with a protease and inhibiting degradation of a protein by the protease from candidate molecules. For example, in the aforementioned method of screening for a protein-degradation inducing tag, a molecule which does not inhibit degradation of a protein by a protease is specified from molecules having an affinity with the protease, and thus a molecule (a protease inhibitor) having an affinity with the protease and inhibiting degradation of a protein by the protease is specified during the screening process. Therefore, a protein-degradation inducing tag may be manufactured using a protease inhibitor obtained by the screening method as described above.

Library of Protein-Degradation Inducing Tags

The library of protein-degradation inducing tags according to the present disclosure includes two or more types of the aforementioned protein-degradation inducing tags. The library of protein-degradation inducing tags can be used in the screening method described below.

Protein-Degradation Inducing Molecule

The protein-degradation inducing molecule according the present disclosure is a conjugate of at least one protein-degradation inducing tag described above and at least one protein binding molecule capable of binding to a protein. The above protein-degradation inducing molecule enables the at least one protein binding molecule to bind with a target protein, leading the target protein to degradation (knockdown) by a protease (for example, a proteasome) without ubiquitination of the target protein (see Examples 2, 7, 12, 15, 16, 21 to 23 described above). It is noted that there is no particular limitation for the binding mode between the protein binding molecule and the target protein, but examples of the binding mode include a covalent bond, a hydrogen bond, a hydrophobic bond, Van der Waals force, and the like.

Examples of the target protein include proteins residing inside a cell or on a cell membrane. The target protein may be a mutant protein produced by mutation, or may be a fusion protein produced by translocation and the like. Further, the target protein may be an endogenous protein, or may be an exogenous protein from viruses, bacteria, and the like. Moreover, the target protein may be a protein which is not promptly degraded, and thus accumulated for some reasons. In a certain embodiment, the target protein is a protein involving in cell cycle, signal transduction, cell differentiation, cell dedifferentiation, cell proliferation, production of a biologically active substance such as cytokine, or the like. It is noted that the target protein does not need to be pre-specified. An unknown target protein can be identified as described below by using a protein-degradation inducing molecule.

Examples of the protein binding molecule include medicaments such as low molecular weight compounds, antibodies, and peptides; endogenous biologically active substances such as cytokines, growth factors, hormones; natural products; metabolites; plant ingredients; food ingredients; and the like. Binding molecules (e.g. inhibitors) in some types of the target protein are known (for example, see WO2008/123266), and thus these known molecules can be used as protein binding molecules. When a molecule capable of binding to a target protein is unknown, binding molecules may be screened by high throughput screening (HTS). Alternatively, an antibody capable of binding to a target protein may be produced, which may be used as a protein binding molecule.

There is no particular limitation for the form of a conjugate of a protein-degradation inducing tag and a protein binding molecule as long as the affinity of the protein-degradation inducing tag with a protease and the binding of the protein binding molecule with a protein are maintained.

For example, the protein-degradation inducing molecule may have a structure in which at least one protein-degradation inducing tag and at least one protein binding molecule are linked. The protein-degradation inducing molecule may have a structure in which one protein-degradation inducing tag is linked to one protein binding molecule, or may have a structure in which one protein-degradation inducing tag is linked to a plurality of protein binding molecules, or may have a structure in which a plurality of protein-degradation inducing tags are linked to one protein binding molecule, or may have a structure in which a plurality of protein-degradation inducing tags are linked to a plurality of protein binding molecules. In a certain embodiment, the protein-degradation inducing molecule has a structure in which one protein-degradation inducing tag is linked to one protein binding molecule.

There is no particular limitation for the linkage position of a protein-degradation inducing tag with the protein binding molecule as long as an affinity with a protease is maintained. For example, when the protein-degradation inducing tag has a structure in which the active site of a protease inhibitor (for example, a proteasome inhibitor) is replaced with another structural moiety as described above, the protein-degradation inducing tag can be bound to the protein binding molecule at the replaced another structural moiety. Specifically, when the active site of a protease inhibitor is replaced with a carboxy group, the protein-degradation inducing tag can be bound to the protein binding molecule through the carboxy group. On the other hand, there is no particular limitation for the linkage position of the protein binding molecule with the protein-degradation inducing tag as long as binding property with a protein is maintained.

It is noted that the protein-degradation inducing tag and the protein binding molecule may be configured to be linked to each other. When a protein-degradation inducing tag is difficult to be directly linked to a protein binding molecule, a structure which enables mutual linkage may be introduced into at least one of the protein-degradation inducing tag and the protein binding molecule. For example, a molecule known to bind with a target protein can be used as a protein binding molecule, but a direct linkage between this known molecule and a protein-degradation inducing tag may potentially be difficult to form. In such a case, a structure which can be linked to a protein-degradation inducing tag may be introduced into the aforementioned known molecule for use as a protein binding molecule.

Library of Protein-Degradation Inducing Molecules

The library of protein-degradation inducing molecules according to the present disclosure includes two or more types of the aforementioned protein-degradation inducing molecules. Examples of the form in which two or more types of protein-degradation inducing molecules are included include a form in which two or more types of protein-degradation inducing molecules having the same type of protein-degradation inducing tags but having different types of protein binding molecules are included, a form in which two or more types of protein-degradation inducing molecules having the same type of protein binding molecules but having different types of protein-degradation inducing tags are included, and a form in which two or more types of protein-degradation inducing molecules having different types of protein-degradation inducing tags and having different types of protein binding molecules are included.

There is no particular limitation for the method of manufacturing a library of protein-degradation inducing molecules. Examples of the method of manufacturing a library of protein-degradation inducing molecules include a method in which protein-degradation inducing tags are conjugated to each protein binding molecule included in the library of protein binding molecules. Examples of the library of protein binding molecules include a compound library, a drug library, a natural product library, and the like. For example, a library of protein-degradation inducing molecules can be manufactured by linking protein-degradation inducing molecules to each protein binding molecule included in a library of protein binding molecules using a chemical reaction, a crosslinking reaction, and the like. Other examples of the method of manufacturing a library of protein-degradation inducing molecules include a method in which protein binding molecules are conjugated to each protein-degradation inducing tag included in the aforementioned library of protein-degradation inducing tags.

The library of protein-degradation inducing molecules can be used in the screening method described below.

Pharmaceutical Composition

The pharmaceutical composition according to the present disclosure includes the aforementioned protein-degradation inducing tag or the protein-degradation inducing molecule. As described above, the protein-degradation inducing tag can lead a target protein to degradation (knockdown) by a protease (for example, a proteasome) without ubiquitination of the target protein, the protein-degradation inducing tag being used alone when the protein-degradation inducing tag is capable of binding to the target protein, or conjugated (the protein-degradation inducing molecule) to a protein binding molecule capable of binding to the target protein when the protein-degradation inducing tag is incapable of binding to the target protein. Therefore, when a target protein is responsible for a certain disease (disease causative agent), a pharmaceutical composition against that disease can be manufactured by using a protein-degradation inducing tag or a protein-degradation inducing molecule which can lead the target protein to degradation. Then, the above pharmaceutical composition is administered to a patient to promote degradation of the target protein in the body of the patient. This can lead to prevention or treatment of that disease (for example, see Example 16 described below which represents a knockdown experiment in mouse individuals).

In the conventional drug discovery methodology where drug discovery is performed based on the form of a target protein, about 75% of the proteome are thought to be undruggable targets. In contrast, according to the aforementioned protein-degradation inducing tag, or protein-degradation inducing molecule, any protein can be targeted in principle. Here, the target protein is from eukaryote or prokaryote (animal, plant, fungus, yeast, E. coli, and the like). The target protein may be a mutant protein produced by mutation, or may be a fusion protein produced by translocation and the like. Further, the target protein may be an endogenous protein, or may be an exogenous protein from viruses, bacteria, and the like. Moreover, the target protein may be a protein which is not promptly degraded, and thus accumulated for some reasons.

The pharmaceutical composition may include an ingredient other than the protein-degradation inducing tag or protein-degradation inducing molecule. For example, the pharmaceutical composition may include an organic or inorganic carrier which is conventionally used as a formulation material. The above carrier is formulated as an excipient, a lubricant, a binder, a disintegrating agent, and the like in a solid preparation, and as a solvent, a solubilizing agent, a suspending agent, an isotonizing agent, a buffer agent, and the like in a liquid preparation. Further, the pharmaceutical composition may include a formulation additive such as an antiseptic agent, an anti-oxidative agent, a coloring agent, a sweetening agent, and the like.

There is no particular limitation for the dosage form of the pharmaceutical composition. Examples of the dosage form of the pharmaceutical composition include oral preparations such as tablet, capsule, granule, powder, trochiscus, syrup, emulsion, suspension, and film preparations; parenteral preparations such injectable preparations, infusion preparations, external preparations, suppository, pellets, transnasal preparations, pulmonary preparations (inhalation), and eye drops; and the like.

The dose of the pharmaceutical composition is appropriately determined depending on the subject, route of administration, target disease, conditions, and the like.

Method of Degrading Target Protein

The method of degrading a target protein according to the present disclosure includes a step of inducing degradation of a target protein using the aforementioned protein-degradation inducing tag or protein-degradation inducing molecule.

There is no particular limitation for the method of inducing degradation of a target protein using the protein-degradation inducing tag or protein-degradation inducing molecule. For example, the protein-degradation inducing tag or protein-degradation inducing molecule may be added to a medium in which cells, a tissue, or an organ is cultured. Any cells, tissue, and organ can be used as long as they are from eukaryote or prokaryote (animal, plant, fungus, yeast, E. coli, and the like) which have a protease (for example, a proteasome). Alternatively, the protein-degradation inducing tag or protein-degradation inducing molecule may be administered orally or parenterally to the living body of eukaryote or prokaryote which has a protease (for example, a proteasome). Subjects of administration include primate such as human, mouse, rat, swine, canine, feline, and the like. Alternatively, the protein-degradation inducing tag or protein-degradation inducing molecule may be added to an in vitro (cell free) protease degradation system (for example, a proteasome degradation system).

As described above, the protein-degradation inducing tag can lead a target protein to degradation (knockdown) by a protease (for example, a proteasome) without ubiquitination of the target protein, the protein-degradation inducing tag being used alone when the protein-degradation inducing tag is capable of binding to the target protein, or conjugated (the protein-degradation inducing molecule) to a protein binding molecule capable of binding to the target protein when the protein-degradation inducing tag is incapable of binding to the target protein.

Method of Performing Functional Analysis on Target Protein

The method of performing functional analysis on a target protein according to the present disclosure includes a step of inducing degradation of the target protein using the aforementioned protein-degradation inducing tag or protein-degradation inducing molecule. As used herein, the term "functional analysis on a target protein" means analyzing functions of the target protein when the target protein is specified. The target protein may have completely unknown functions or partially elucidated functions.

There is no particular limitation for the method of inducing degradation of a target protein using the protein-degradation inducing tag or protein-degradation inducing molecule. For example, the protein-degradation inducing tag or protein-degradation inducing molecule may be added to a medium in which cells, a tissue, or an organ is cultured. Alternatively, the protein-degradation inducing tag or protein-degradation inducing molecule may be administered orally or parenterally to the living body of eukaryote or prokaryote which has a protease (for example, a proteasome). Alternatively, the protein-degradation inducing tag or protein-degradation inducing molecule may be added to an in vitro (cell free) functional analysis system along with a protease degradation system (for example, a proteasome degradation system).

As described above, the protein-degradation inducing tag can lead a target protein to degradation (knockdown) by a protease (for example, a proteasome) without ubiquitination of the target protein, the protein-degradation inducing tag being used alone when the protein-degradation inducing tag is capable of binding to the target protein, or conjugated (the protein-degradation inducing molecule) to a protein binding molecule capable of binding to the target protein when the protein-degradation inducing tag is incapable of binding to the target protein. Accordingly, when eukaryote or prokaryote, or cells thereof are used, functions of a target protein can be analyzed by, for example, inducing degradation of the target protein using the protein-degradation inducing tag or protein-degradation inducing molecule, and then analyzing changes in the phenotype of the cells or living body. Alternatively, when an in vitro (cell free) functional analysis system is used, functions of a target protein can be analyzed by inducing degradation of the target protein using the protein-degradation inducing tag or protein-degradation inducing molecule, and then analyzing differences (changes) in molecular networks in the presence or absence of the target protein.

Traditionally, when functions of a target protein are analyzed in the living body of an animal, a gene knockout mouse is usually created. However, disadvantageously, a long period of time (for example, 1 year or more) is required to create a gene knockout mouse. In recent years, the genome editing technique (CRISPR/CAS9) has been developed. Nonetheless, creation of a gene knockout mouse takes several months to half a year even when this CRISPR/CAS9 technique is used. In contrast, according to the aforementioned protein-degradation inducing tag or protein-degradation inducing molecule, a target protein can be led to degradation (knockdown) in a short period of time, and an effect comparable to a case where a gene knockout mouse is created can be obtained. Further, according to the aforementioned protein-degradation inducing tag or protein-degradation inducing molecule, functions of a target protein can also be analyzed dynamically.

Method of Identifying Target Protein

The method of identifying a target protein according to the present disclosure includes a step of inducing degradation of the target protein using the aforementioned protein-degradation inducing tag or protein-degradation inducing molecule; and a step of identifying a protein subjected to degradation induced by the protein-degradation inducing tag or protein-degradation inducing molecule. As used herein, the term "identifying a target protein" means that a target protein capable of binding to a protein-degradation inducing tag or a protein binding molecule is identified. The protein-degradation inducing tag or the protein binding molecule may bind to not only a completely unknown target protein but a partially known target protein.

According to the method of identifying a target protein, protein degradation is first induced using the aforementioned protein-degradation inducing tag or protein-degradation inducing molecule. There is no particular limitation for the method of inducing protein degradation using the protein-degradation inducing tag or protein-degradation inducing molecule. For example, the method of degrading a target protein as described above may be adopted.

Next, a protein is identified, of when degradation having been induced by the protein-degradation inducing tag or the protein-degradation inducing molecule. As described above, the protein-degradation inducing tag can lead a target protein to degradation (knockdown) by a protease (for example, a proteasome) without ubiquitination of the target protein, the protein-degradation inducing tag being used alone when the protein-degradation inducing tag is capable of binding to the target protein, or conjugated (the protein-degradation inducing molecule) to a protein binding molecule capable of binding to the target protein when the protein-degradation inducing tag is incapable of binding to the target protein. Subsequently, the target protein can be identified by, for example, extracting proteins from cells, and performing proteome analysis to specify a protein present in a reduced amount.

Method of Identifying Pathway Molecule Through Target Protein

The method of identifying a pathway molecule through a target protein according to the present disclosure includes a step of inducing degradation of the target protein using the aforementioned protein-degradation inducing tag or protein-degradation inducing molecule; and a step of identifying a protein showing an altered activity or expression, the protein being different from the target protein. As used herein, the term "identifying a pathway molecule through a target protein" means that identifying a protein other than the target protein in a protein pathway (a signal transduction pathway and the like) where the target protein is involved. The pathway molecule through a target protein may be not only completely unknown but partially known.

According to the method of identifying a pathway molecule through a target protein, protein degradation is first induced using the aforementioned protein-degradation inducing tag or protein-degradation inducing molecule. There is no particular limitation for the method of inducing protein degradation using the protein-degradation inducing tag or protein-degradation inducing molecule. For example, the method of degrading a target protein as described above may be adopted.

Next, a protein showing an altered activity or expression which is different from the target protein is identified. As described above, the protein-degradation inducing tag can lead a target protein to degradation (knockdown) by a protease (for example, a proteasome) without ubiquitination of the target protein, the protein-degradation inducing tag being used alone when the protein-degradation inducing tag is capable of binding to the target protein, or conjugated (the protein-degradation inducing molecule) to a protein binding molecule capable of binding to the target protein when the protein-degradation inducing tag is incapable of binding to the target protein. At this time, the activity or expression of another protein along a protein pathway where the target protein is involved may be altered as the target protein undergoes degradation. Therefore, a pathway molecule can be identified through a target protein by specifying another protein showing an altered activity or expression.

It is noted that when an increase or decrease in the target protein is responsible for a decrease, identification of a pathway molecule through the target protein can contribute to elucidation of the mechanism of that disease.

Method of Screening for Protein-Degradation Inducing Tag or
Protein-Degradation Inducing Molecule The method of screening for a protein-degradation inducing tag or protein-degradation inducing molecule according to the present disclosure includes a step of introducing the aforementioned protein-degradation inducing tag, library of protein-degradation inducing tags, protein-degradation inducing molecules, or library of protein-degradation inducing molecules to a system including a target protein present, and a step of selecting a protein-degradation inducing tag or protein-degradation inducing molecule which has induced degradation of the target protein.

There is no particular limitation for the system including a target protein, but it may be, for example, a protease degradation system (for example, a proteasomal degradation system) using eukaryotic or prokaryotic cells which have a protease (for example, a proteasome) or an in vitro (cell-free) protease degradation system (for example, a proteasomal degradation system).

When a protein-degradation inducing tag or protein-degradation inducing molecule capable of binding to a target protein is included in the protein-degradation inducing tag, library of protein-degradation inducing tags, protein-degradation inducing molecule, or library of protein-degradation inducing molecules introduced to the system including the target protein, the target protein is led to degradation (knockdown) by a protease (for example, a proteasome). Therefore, what is necessary is just to select a protein-degradation inducing tag or protein-degradation inducing molecule which has induced such degradation of the target protein upon screening.

According to the above screening method, a protein-degradation inducing tag or protein-degradation inducing molecule which leads any selected target protein to degradation can be obtained in principle. Further, when a target protein is responsible for a certain disease (disease causative agent), a protein-degradation inducing tag or protein-degradation inducing molecule which leads the target protein to degradation can be selected as a candidate ingredient for preventing or treating that disease.

Method of Screening Candidate Ingredient for Preventing or Treating Disease

One embodiment of the method of screening for a candidate ingredient for preventing or treating a disease according to the present disclosure includes a step of introducing the aforementioned protein-degradation inducing tag, library of protein-degradation inducing tags, protein-degradation inducing molecule, or library of protein-degradation inducing molecules to a disease model system, and selecting a protein-degradation inducing tag or protein-degradation inducing molecule which has improves a condition of the disease. Moreover, another embodiment of the method of screening for a candidate ingredient for preventing or treating a disease according to the present disclosure includes a step of introducing the aforementioned protein-degradation inducing tag, library of protein-degradation inducing tags, protein-degradation inducing molecule, or library of protein-degradation inducing molecules to a disease model system, and extracting a protein-degradation inducing tag or a protein-degradation inducing molecule which has aggravated a condition of the disease, and selecting a protein subjected to degradation induced by the extracted protein-degradation inducing tag or the extracted protein-degradation inducing molecule.

There is no particular limitation for the disease model system, but examples thereof include disease model animals, disease model cells, and the like.

When a protein-degradation inducing tag or protein-degradation inducing molecule capable of binding to a protein related to a disease (disease-related protein) is included in the protein-degradation inducing tag, library of protein-degradation inducing tags, protein-degradation inducing molecule, or library of protein-degradation inducing molecules introduced into the disease model system, the disease-related protein is led to degradation (knockdown) by a protease (for example, a proteasome). When a condition of the disease is improves as a result of degradation of the disease-related protein, an increase in the disease-related protein may potentially be related to development or progress of the disease. Therefore, a candidate ingredient for preventing or treating a disease can be obtained by selecting a protein-degradation inducing tag or protein-degradation inducing molecule which has improved a condition of the disease. On the other hand, when a condition of the disease is aggravated as a result of degradation of the disease-related protein, a decrease in the disease-related protein may potentially be related to development or progress of the disease. Therefore, a candidate ingredient for preventing or treating a disease can be obtained by extracting a protein-degradation inducing tag or protein-degradation inducing molecule which aggravates a condition of the disease, and selecting a protein subjected to degradation induced by the extracted protein-degradation inducing tag or the extracted protein-degradation inducing molecule.

Method of Specifying Disease-Related Protein

The method of specifying a disease-related protein according to the present disclosure includes a step of introducing the aforementioned protein-degradation inducing tag, library of protein-degradation inducing tags, protein-degradation inducing molecule, or library of protein-degradation inducing molecules into a disease model system, and extracting a protein-degradation inducing tag or a protein-degradation inducing molecule which has altered a condition of the disease, and selecting a protein subjected to degradation induced by the extracted protein-degradation inducing tag or the extracted protein-degradation inducing molecule.

When a protein-degradation inducing tag, a library of protein-degradation inducing tags, a protein-degradation inducing molecule, or a library of protein-degradation inducing molecules is introduced into a disease model system, a condition of a disease may be altered as protein degradation (knockdown) progresses in the disease model system. Therefore, disease-related protein can be specified by extracting a protein-degradation inducing tag or protein-degradation inducing molecule which has altered a condition of the disease, and selecting a protein subjected to degradation induced by the extracted protein-degradation inducing tag or the extracted protein-degradation inducing molecule.

Information about a disease-related protein specified can be used, for example, to develop an ingredient for preventing or treating a disease.

EXAMPLES

Below, the present invention will be described specifically with reference to Examples, but the present invention shall not be limited to Examples.

Abbreviations of compounds used in the following Examples are as follows.

ec: *Escherichia coli*
DHFR: Dihydrofolate reductase
TMP: Trimethoprim
H-Phe-OtBu.HCl: L-Phenylalanine t-butyl ester hydrochloride
DMF: N,N-Dimethylformamide
DMT-MM: 4-(4,6-Dimethoxy-1,3,5-triazin-2-yl)-4-methyl-morpholinium chloride n-hydrate
TFA: Trifluoroacetic acid
H-Leu-OtBu.HCl: L-Leucine t-butyl ester hydrochloride
DIEA: N,N-Diisopropylethylamine
D-MEM: Dulbecco's modified eagle's medium
FBS: Fetal bovine serum
EDTA: Ethylenediamine tetraacetic acid
HA: Hemagglutinin
GFP: Green fluorescent protein
DsRed: Discosoma sp. red fluorescent protein
DMSO: Dimethyl sulfoxide
PBS: Phosphate buffered saline
TBS: Tris buffered saline
SDS: Sodium dodecyl sulfate
PAGE: Polyacrylamide gel ectrophoresis
BPB: Bromophenol blue
PVDF: Polyvinylidene difluoride
AMC: 7-Amino-4-methylcoumarin
H-Gly-OtBu.HCl: L-Glycine t-butyl ester hydrochloride
PyBOP: 1H-Benzotriazol-1-yloxy-tri(pyrrolidino)phosphonium hexafluorophosphate
MTX: Methotrexate
DMA: N,N-Dimethylacetamide
BOP: 1H-Benzotriazol-1-yloxy-tris(dimethylamino)phosphonium hexafluorophosphate
TEA: Triethylamine
HATU: O-(7-Azabenzotriazol-1-yl)-N,N,N',N'-tetramethyluronium hexafluorophosphate
GAPDH: Glyceraldehyde 3-phosphate dehydrogenase Example 1

Synthesis of Protein-Degradation Inducing Molecule (TMP-CiKD_Bortezomib) Having CiKD_Bortezomib as Protein-Degradation Inducing Tag and TMP Derivative as Protein Binding Molecule In Example 1, TMP-CiKD_Bortezomib as a protein-degradation inducing molecule was synthesized according to the following synthesis scheme. Bortezomib-COOH (CiKD_Bortezomib) in which the boronyl group as the active site of bortezomib was replaced with a carboxy group was used as a protein-degradation inducing tag. Further, a TMP derivative (TMP-NH$_2$) in which a functional group including an amino group was introduced into TMP as a dihydrofolate reductase inhibitor capable of binding to *E. coli* DHFR was used as a protein binding molecule. Then, Bortezomib-COOH was linked to TMP-NH$_2$ to synthesize TMP-CiKD_Bortezomib as a protein-degradation inducing molecule.

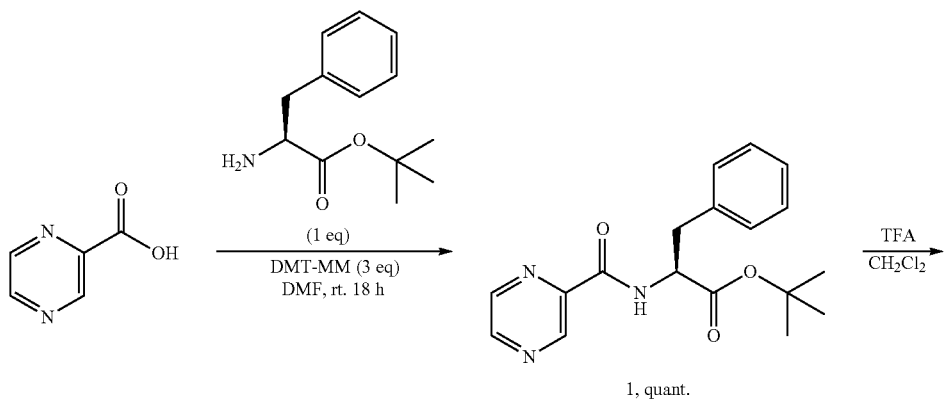

1, quant.

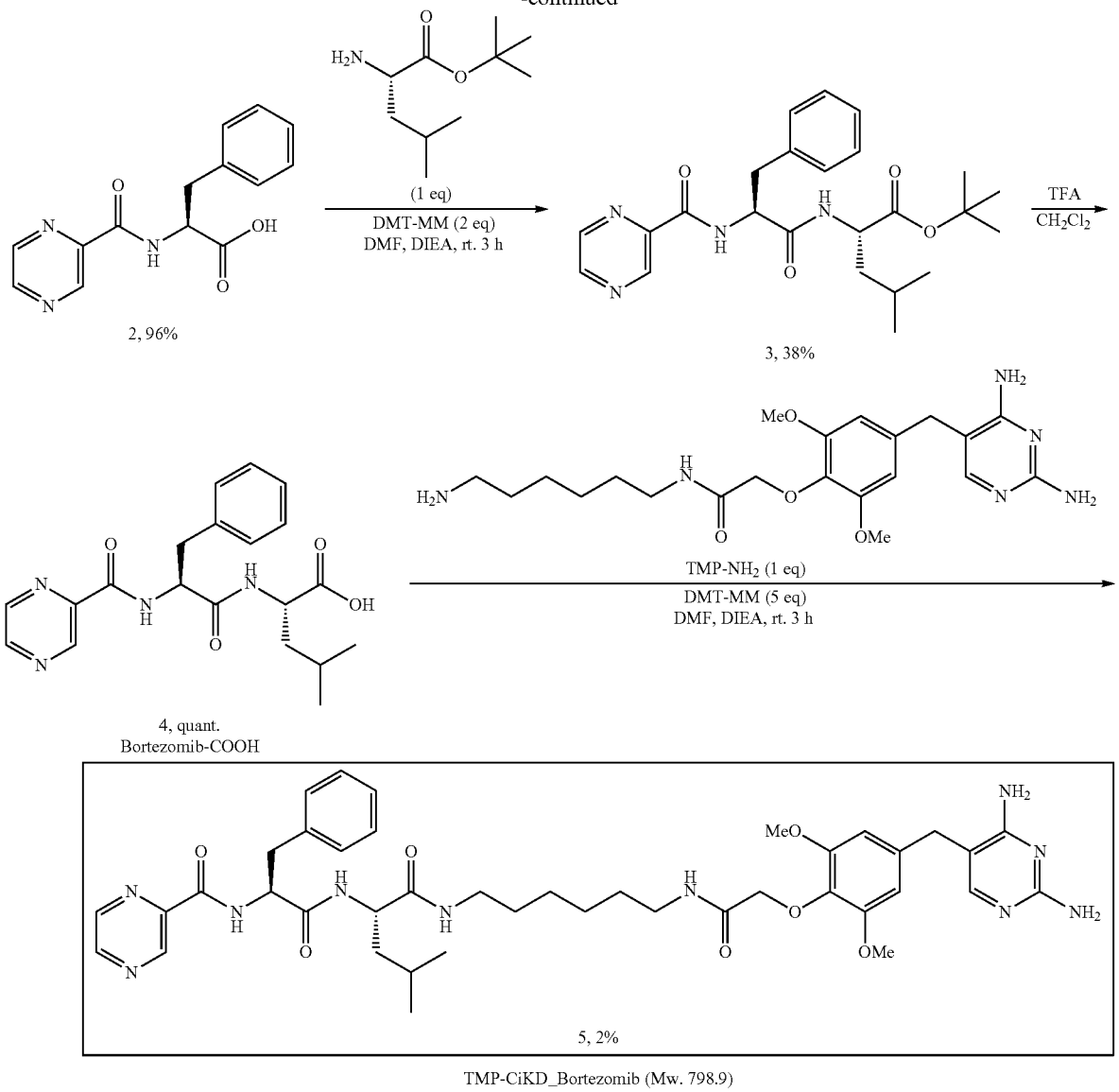

The method of synthesizing TMP-CiKD_Bortezomib is described in detail as follows.

(Synthesis of Compound 1)

Pyrazinecarboxylic acid (152.8 mg, 1.23 mmol, 1 eq, Code No. 357-00042, Wako Pure Chem Industries, Ltd.) and H-Phe-OtBu.HCl (253.8 mg, 0.98 mmol, 0.8 eq, Code No. 10Y830617, Watanabe Chemical Industries, Ltd.) were charged into an eggplant flask, and 10 mL of dehydrate DMF was then added. After stirred for 5 minutes at room temperature, DMT-MM (1.02 g, 3.69 mmol, 3 eq, Code No. 329-53751, Wako Pure Chem Industries, Ltd.) was directly added to the reaction solution, and stirred at room temperature for 18 hours. The reaction solution was diluted with water, and extracted with ethyl acetate for 3 times. This was washed with brine, and then dried over anhydrous sodium sulfate. After evaporating the solvent under reduced pressure, separation and purification treatment was performed by silica gel chromatography (Code No. 30511-35, Nacalai Tesque, Inc.) (hexane/chloroform=1/1 to 0/1, gradient) to obtain a compound 1 (482.3 mg, 1.47 mmol, quant.).

(Synthesis of Compound 2)

The compound 1 (398.4 mg, 1.22 mmol) was charged into an eggplant flask, and 5 mL of dichloromethane was then added. This was stirred at room temperature for 5 minutes, and then 7 mL of TFA was added, and stirred at room temperature for 2 hours. After evaporating the solvent under reduced pressure, vacuum drying was performed to obtain a compound 2 (318.8 mg, 96%).

(Synthesis of Compound 3>

The compound 2 (271.3 mg, 1.00 mmol, 1 eq) and H-Leu-OtBu.HCl (223.8 mg, 1.00 mmol, 1 eq, Code No. 14G110356, Watanabe Chemical Industries, Ltd.) were charged into an eggplant flask, and 10 mL of dehydrate DMF was then added. After stirred at room temperature for 5 minutes, 2 mL of DIEA was added to neutralize the solution. After stirred for 5 minutes at room temperature, DMT-MM (553.4 mg, 2.00 mmol, 2 eq, Code No. 329-53751, Wako Pure Chemical Industries, Ltd.) was directly added to the reaction solution, and stirred at room temperature for 3 hours. Under cooling conditions, 20 mL of 10 mass % brine/0.1 N aqueous hydrochloric acid was added, and extracted with ethyl acetate for 3 times. This was washed with 0.5 N aqueous hydrochloric acid and then brine, and then dried over anhydrous sodium sulfate. After evaporating the solvent under reduced pressure, separation and purification treatment was performed by silica gel chromatography (Code No. 30511-35, Nacalai Tesque, Inc.) (hexane/chloroform=1/1 to 0/1, gradient) to obtain a compound 3 (168.1 mg, 0.38 mmol, 38%)

(Synthesis of Compound 4 (Bortezomib-COOH))

The compound 3 (157.3 mg, 0.36 mmol) was charged into an eggplant flask, and 5 mL of dichloromethane was then added. This was stirred at room temperature for 5 minutes, and then 6 mL of TFA was added, and stirred at room temperature for 2 hours. After evaluating the solvent under reduced pressure, vacuum drying was performed to obtain a compound 4 (Bortezomib-COOH) (179.6 mg, 0.48 mmol, quant.).

(Synthesis of Compound 5 (TMP-CiKD_Bortezomib))

The compound 4 (Bortezomib-COOH) (55.7 mg, 0.15 mmol, 1 eq) and TMP-NH$_2$ synthesized separately (Long, M. J. et al., Chem. Biol., 2012, 19 (5), 629-637) (62.7 mg, 0.15 mmol, 1 eq) were charged into an eggplant flask, and 7 mL of dehydrate DMF was added. After stirred at room temperature for 5 minutes, 2 mL of DIEA was added to neutralize the solution. After stirred at room temperature for 5 minutes, DMT-MM (207.5 mg, 0.75 mmol, 5 eq, Code No. 329-53751, Wako Pure Chemical Industries, Ltd.) was directly added to the reaction solution, and stirred at room temperature for 3 hours. Under cooling conditions, 20 mL of 10 mass % brine/0.1 N aqueous hydrochloric acid was added, and extracted with ethyl acetate for 3 times. This was washed with 0.5 N aqueous hydrochloric acid and then brine, and then dried over anhydrous sodium sulfate. After evaporating the solvent under reduced pressure, separation and purification treatment was performed by silica gel chromatography (Code No. 30511-35, Nacalai Tesque, Inc.) (chloroform/methanol=10/1). Subsequently, separation and purification treatment was performed with a TLC silica gel 60 (Code No. HX264817, Merck) (chloroform/methanol=10/1) to obtain a compound 5 (TMP-CiKD_Bortezomib) (2.3 mg, 0.0029 mmol, 2%, isolated yield).

Example 2

Evaluation (FACS Analysis) of Degradation (Knockdown) of Forcedly Expressed Target Protein (E. coli DHFR) in HeLa Cells to which Protein-Degradation Inducing Molecule (TMP-CiKD_Bortezomib) was Added In Example 2, degradation (knockdown) of a forcedly expressed target protein (E. coli DHFR) in HeLa cells to which TMP-CiKD_Bortezomib was added was evaluated by FACS analysis.

(Preparation of Cultured Cells)

As a preculture medium, prepared was a medium where 10 mass % FBS (Code No. SH30910.03, Lot. No. AYG161516, HyClone) and 1 mass % PenStrep (100 U/mL sodium penicillin G and 100 µg/mL streptomycin sulfate) (Code No. 168-23191, Wako Pure Chemical Industries, Ltd.) were added to D-MEM (low D-glucose, L-glutamine, phenol red (Code No. 041-29775, Wako Pure Chemical Industries, Ltd.). Then, HeLa cells (Lot No. 60143948, ATCC) were cultured in the preculture medium under conditions of 37° C. and 5 vol % CO$_2$. As a culture dish for passage culture, used was a cell culture-dish, treated having a diameter of 100 mm (sterile, non pyrogenic) (Code No. TR4002, TrueLine). Passage culture was performed at the time of 70% to 80% confluence. Cells were detached by trypsin treatment (0.25 w/v % trypsin-1 mmol/L EDTA-4 Na solution with phenol red) (Code No. 201-16945, Wako Pure Chemical Industries, Ltd.), and then one quarter of the cells were cultured in 10 mL of the preculture medium.

(Introduction of Plasmid into HeLa Cells and Cell Seeding)

A plasmid was introduced into HeLa cells to transiently overexpress E. coli DHFR as a target protein (specifically, a fusion protein of E. coli DHFR and GFP through a HA tag) or DsRed for comparison in the cells, and the effects of TMP-CiKD_Bortezomib on the target protein were evaluated.

The plasmid (pMIR DsRed-IRES-ecDHFR-HA-GFP) was provided by Professor Lizbeth Hedstrom at Brandeis University (the United States) (Long, M. J. et al., "Inhibitor mediated protein degradation." Chem. Biol., 2012, 19 (5), 629-637). The plasmid map of pMIR DsRed-IRES-ecDHFR-HA-GFP is shown in FIG. 1. The plasmid was amplified in E. coli, and then purified with a Miniprep kit (Code No. 27106, QIAGEN).

ScreenFect™ A (Code No. 297-73201, Wako Pure Chemical Industries, Ltd.) as a transfection reagent was used to introduce the plasmid into HeLa cells. A dilution buffer of ScreenFect™ A was added to two 1.5 mL tubes at 600 UL per tube. Then, 30 µL of a transfection reagent of ScreenFect™ A was added to one tube (a solution A), and 12 µg of the plasmid was added to the other tube (a solution B), and each tube was lightly pipetted, and then allowed to stand at room temperature for 2 minutes. The solution A was lightly mixed with the solution B, and allowed to stand at room temperature for 30 minutes (a solution C). The solution C was mixed with a cell solution at 1.2×10$^5$ cells/24 mL collected from trypsin treatment, and seeded on a 24-well plate (Code No. TR5002, TrueLine, Nippon Genetics Co., Ltd.) at a cell density of 4×10$^4$ cells/800 µL/well, and then cultured under conditions of 37° C. and 5 vol % CO$_2$ for 40 hours.

(Addition of Protein-Degradation Inducing Molecule (TMP-CiKD_Bortezomib) to HeLa Cells)

TMP-CiKD_Bortezomib was added to HeLa cells as follows. Culture was performed for 40 hours after introduction of the plasmid, and then the preculture medium was removed, and a serum-free medium (37° C.) in which a 1 mass % L-glutamine solution (Code No. G7513, Sigma-Aldrich) was added to D-MEM (high D-Glucose, phenol red, and sodium pyruvate (Code No. 045-32245, Wako Pure Chemical Industries, Ltd.) was added to each well at 300 µL/well. It is noted that the L-glutamine solution was added immediately before use. A DMSO solution containing a predetermined concentration of TMP-CiKD_Bortezomib was added to each well at 3 µL/well, and cultured under conditions of 37° C. and 5 vol % CO$_2$. It is noted that a DMSO solution containing TMP or DMSO was used as a control in place of the DMSO solution containing TMP-CiKD_Bortezomib.

(Evaluation of Target Degradation (Knockdown) Due to TMP-CiKD_Bortezomib by FACS Analysis)

The medium was removed 24 hours after addition of TMP-CiKD_Bortezomib (80 µM) or TMP (80 µM), and then PBS (Wako Pure Chemical Industries, Ltd.) at 37° C. was added to each well at 2 mL/well to wash the cells. After removing PBS, trypsin (0.25 w/v % trypsin-1 mmol/L EDTA-4 Na solution with phenol red) (Wako Pure Chemical Industries, Ltd.) at 37° C. was added to each well at 200 µL/well, and cultured under conditions of 37° C. and 5 vol % CO$_2$ for 1 minute. After culturing, a medium where 10 mass % FBS (Code No. SH30910.03, Lot No. AYG161516, HyClone) and 1 mass % PenStrep (100 U/mL sodium penicillin G and 100 μg/mL streptomycin sulfate) (Code No. 168-23191, Wako Pure Chemical Industries, Ltd.) were added to D-MEM (low D-glucose, L-glutamine, phenol red (Code No. 041-29775, Wako Pure Chemical Industries, Ltd.)) was added to each well at 300 μL/well, and suspended, and then a cell solution was collected in a 15 mL tube.

The cell solution collected was centrifuged (at 1000 rpm×5 minutes, 4° C.), and the supernatant was removed, and then suspended in 2 ml of PBS (37° C.). The cell solution after suspension was centrifuged (at 1000 rpm×5 minutes, 4° C.), and the supernatant was removed, and then 500 μL of an FACS buffer (1 mass % FBS/PBS) at 4° C. was added, and allowed to stand on ice.

A BD FACSCanto™ II (BD Biosciences) was used for flow cytometry, and the expression levels of GFR and DsRed in cells were quantified. The cell solution was passed through a mesh with a pore size of 32 μm, and transferred to an FACS tube immediately before FACS analysis. The GFR/DsRed ratio per cell was computed using an analysis software FLOWJO™ (TOMY Digital Biology Co., Ltd.), and the efficiency of target degradation (knockdown) by TMP-CiKD_Bortezomib was determined from a shift by target degradation in a graph.

Figures 2A, 2B:
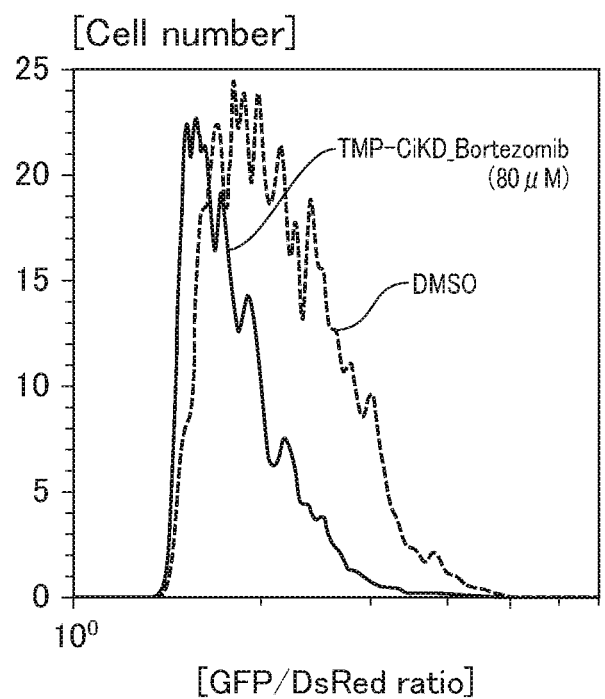
FIG. 2A shows results from FACS (Fluorescence Activated Cell Sorting) analysis of a forcedly expressed target protein (*E. coli* DHFR) in HeLa cells to which TMP-CiKD_Bortezomib was added.
FIG. 2B shows results from the FACS analysis of a forcedly expressed target protein (*E. coli* DHFR) in HeLa cells to which TMP was added.

FIG. 2A shows results from the FACS analysis of a forcedly expressed target protein (*E. coli* DHFR) in HeLa cells to which TMP-CiKD_Bortezomib was added. Further, FIG. 2B shows results from the FACS analysis of a forcedly expressed target protein (*E. coli* DHFR) in HeLa cells to which TMP was added. As can be seen in FIG. 2A, when TMP-CiKD_Bortezomib (80 μM) was added, the graph was found to be significantly shifted to the left as compared with that of the control (DMSO), indicating that the target protein (*E. coli* DHFR) was degraded. The degradation efficiency estimated from the amount of a shift was about 50% to 60%. In contrast, as can be seen in FIG. 2B, when TMP (80 μM) was added, the graph was found to be overlapped with that of the control (DMSO), indicating that the target protein was not degraded.

Example 3

Evaluation (Thermal Shift Assay) of Affinity of Protein-Degradation Inducing Molecule (TMP-CiKD_Bortezomib) with Forcedly Expressed Target Protein (ecDHFR) in HeLa Cells to which Protein-Degradation Inducing Molecule (TMP-CiKD_Bortezomib) was Added In Example 3, the affinity of TMP-CiKD_Bortezomib with a forcedly expressed target protein (*E. coli* DHFR) in HeLa cells to which TMP-CiKD_Bortezomib was added was evaluated by thermal shift assay.

Preparation of Cultured Cells, Introduction of Plasmid into HeLa Cells, and Cell Seeding HeLa cells were prepared as in Example 2. A plasmid (pMIR DsRed-IRES-ecDHFR-HA-GFP) was introduced into HeLa cells as in Example 2, and then seeded on a 24-well plate.

(Addition of Protein-Degradation Inducing Molecule (TMP-CiKD_Bortezomib) to HeLa Cells)

TMP-CiKD_Bortezomib was added to HeLa cells as in Example 2. A DMSO solution containing TMP or DMSO was used as a control in place of the DMSO solution containing TMP-CiKD_Bortezomib.

(Evaluation of Affinity of TMP-CiKD_Bortezomib with Target by Thermal Shift Assay)

The medium was removed 3 hours after addition of TMP-CiKD_Bortezomib (40 μM) or TMP (40 μM), and then PBS (Wako Pure Chemical Industries, Ltd.) at 37° C. was added to each well at 2 mL/well to wash the cells. After removing PBS, trypsin (0.25 w/v % trypsin-1 mmol/L EDTA-4 Na solution with phenol red) (Wako Pure Chemical Industries, Ltd.) at 37° C. was added to each well at 200 μL/well, and cultured under conditions of 37° C. and 5 vol % $CO_2$ for 1 minute. After culturing, a medium where 10 mass % FBS (Code No. SH30910.03, Lot No. AYG161516, HyClone) and 1 mass % PenStrep (100 U/mL sodium penicillin G and 100 μg/mL streptomycin sulfate) (Code No. 168-23191, Wako Pure Chemical Industries, Ltd.) were added to D-MEM (low D-glucose, L-glutamine, phenol red (Code No. 041-29775, Wako Pure Chemical Industries, Ltd.) was added to each well at 300 μL/well, and suspended, and then a cell solution was collected in a 15 mL tube.

The cell solution collected was centrifuged (at 1000 rpm×5 minutes, 4° C.), and the supernatant was removed, and then suspended in 2 ml of PBS (37° C.). The cell solution after suspension was centrifuged (at 1000 rpm×5 minutes, 4° C.), and the supernatant was removed, and then 180 UL of a CETSA buffer (cOmplete™ Mini, EDTA-free (Roche) as a protease inhibitor was added to TBS immediately before use) was added, and then suspended. The cell solution after suspension was dispensed to nine 1.5 mL tubes at 20 μL per tube, and allowed to stand at room temperature for 30 minutes. After allowed to stand, the 9 tubes were heat-treated for 3 minutes, one each at 38° C., 42° C., 46° C., 50° C., 54° C., 58° C., 62° C., 66° C., or 70° C., and allowed to stand at room temperature for 3 minutes. After allowed to stand, the cell solution was flash frozen in liquid nitrogen, and thawed on ice. After repeating this freeze-thaw cycle for 3 times, the solution was centrifuged (at 13500 rpm×20 minutes, 4° C.), and the supernatant (cell extract) was collected.

The cell extract collected was subjected to Western blot analysis. A SDS-PAGE gel (14 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. The electrophoresis samples prepared were applied to each well at 17 μL/well. Precision Plus Protein™ Dual Color Standards (Bio-Rad) were used as electrophoresis markers. Electrophoresis was performed at 150 V for 40 minutes (electrophoresis buffer; 195 mM glycine, 25 mM Tris).

After electrophoresis, proteins were transferred to a PVDF membrane (Immobion™-P, Millipore) under conditions of 100 V and 40 minutes using a tank-type blotting device and a transfer buffer (25 mM Tris-HCl, 195 mM glycine, 0.01% SDS, 15% methanol). The membrane after transfer was shaken and blocked in 5% skim milk/high-salt TBS-T (100 mM Tris-HCl, 500 mM NaCl, 0.2% Tween-20, pH 7.6) at room temperature for 30 minutes. After blocking, the membrane was rinsed with high-salt TBS-T, and an antibody reaction was performed in 1% skim milk/high-salt TBS-T. With regard to antibody, anti-HA-peroxidase, high-affinity (3F10) rat monoclonal antibody (25 U/mL) (Roche) diluted 1500 times was used. The membrane was shaken at room temperature for 90 minutes, and then washed with high-salt TBS-T for 5 minutes. It is noted that washing was performed for 3 times. Further, the membrane was washed with high-salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Figure 3:
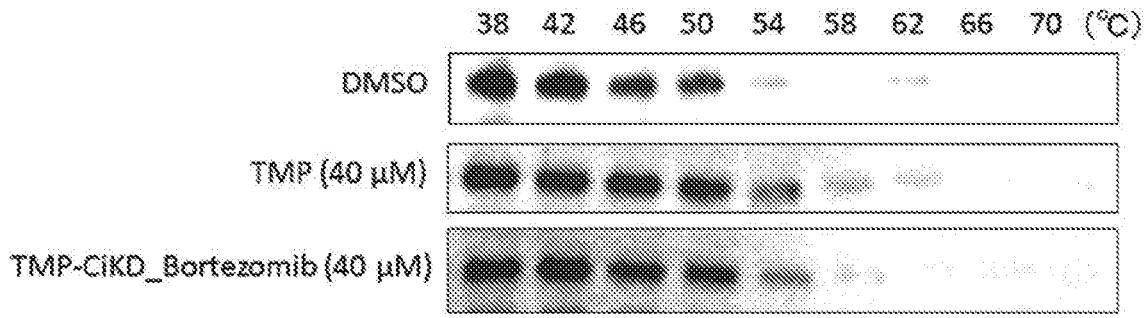
FIG. 3 shows results from the thermal shift assay of a forcedly expressed target protein (*E. coli* DHFR) in HeLa cells to which TMP-CiKD_Bortezomib or TMP was added.

FIG. 3 shows results from the thermal shift assay of a forcedly expressed target protein (*E. coli* DHFR) in HeLa cells to which TMP-CiKD_Bortezomib or TMP was added. As shown in FIG. 3, *E. coli* DHFR was able to be detected only up to about 50° C. for the control (DMSO). In contrast, *E. coli* DHFR was able to be detected up to about 54° C. by virtue of interaction between *E. coli* DHFR and TMP when TMP (40 μM) was added. Similarly, *E. coli* DHFR was able to be detected up to about 54° C. by virtue of interaction between *E. coli* DHFR and TMP-CiKD_Bortezomib when TMP-CiKD_Bortezomib (40 μM) was added. It is noted that bortezomib alone as a proteasome inhibitor did not interact with *E. coli* DHFR. These results show that TMP-CiKD_Bortezomib, in which TMP-NH$_2$ is linked to CiKD_Bortezomib, has an affinity with *E. coli* DHFR to a similar extent as TMP.

Example 4

Evaluation of Proteasome Inhibitory Activity of Protein-Degradation Inducing Molecule (TMP-CiKD_Bortezomib) and Affinity Thereof with Proteasome In Example 4, the proteasome inhibitory activity of TMP-CiKD_Bortezomib, and the affinity of TMP-CiKD_Bortezomib with a proteasome were evaluated.

For evaluation, AMC released when the C-terminus of an AMC-conjugated proteasome fluorescent substrate specific to a β subunit of β5 (chymotrypsin-like activity), β2 (trypsin-like activity), and β1 (caspase-like activity) of 20S proteasome was cut using 20S Proteasome StressXpress™ Assay Kit Gold (Bioscience) was measured with a multi-detection microplate reader (Synergy HT, BIO-TEK). The measurement wavelengths were 360 nm for excitation light (Ex.), and 460 nm for fluorescence (Em.).

Figure 4A:
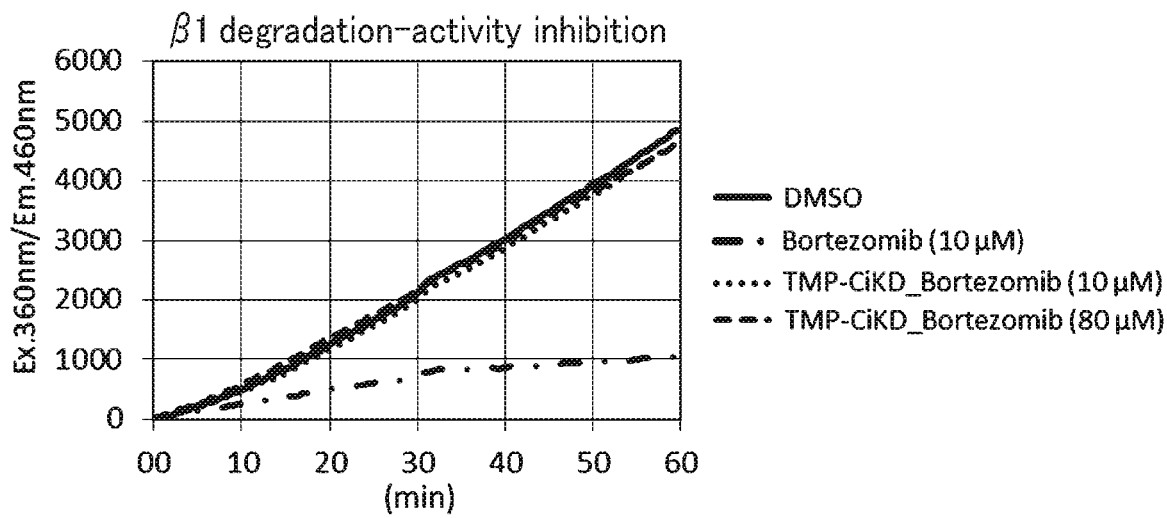
FIG. 4A shows the inhibitory activity of TMP-CiKD_Bortezomib and Bortezomib against the catalytic subunit β1 of a proteasome.
Figure 4B:
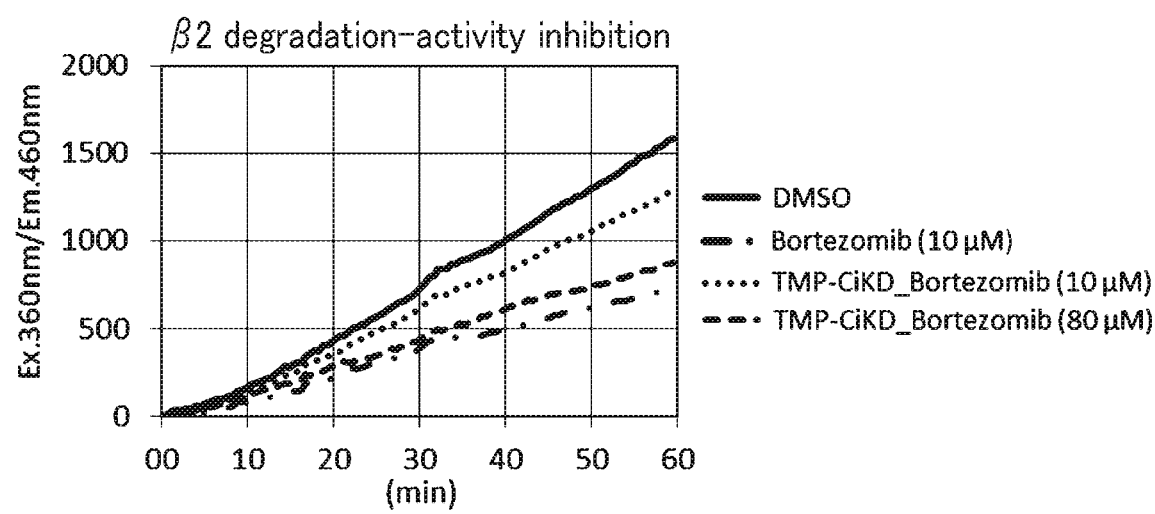
FIG. 4B shows the inhibitory activity of TMP-CiKD_Bortezomib and Bortezomib against the catalytic subunit β2 of the proteasome.
Figure 4C:
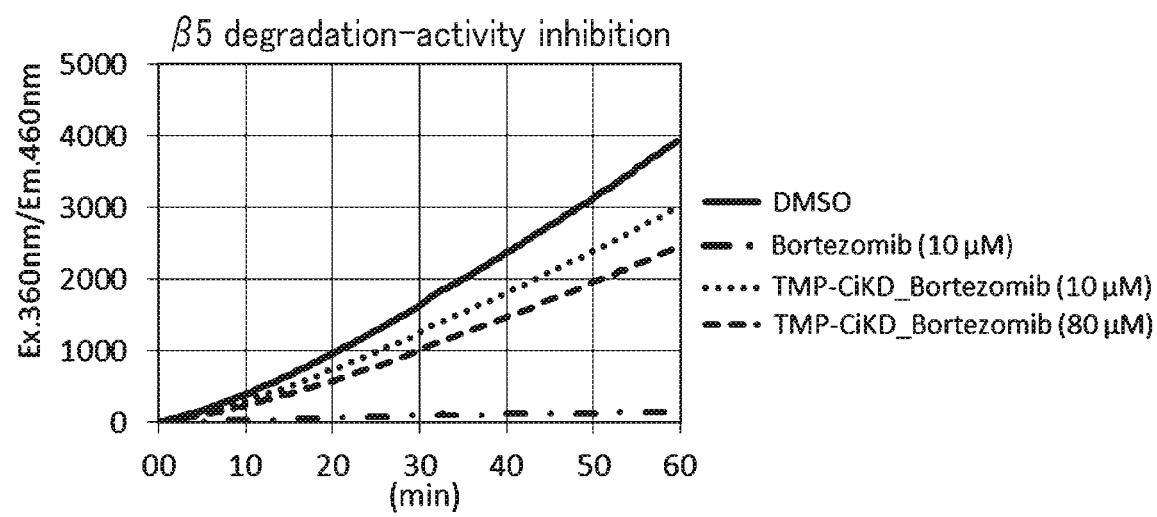
FIG. 4C shows the inhibitory activity of TMP-CiKD_Bortezomib and Bortezomib against the catalytic subunit β5 of the proteasome.

FIGS. 4A to 4C show the proteasome activities against 01 (caspase-like activity), β2 (trypsin-like activity), and β5 (chymotrypsin-like activity), respectively. As can be seen in FIGS. 4A to 4C, the inhibitory activity of TMP-CiKD_Bortezomib against β1 and β5 was found to be substantially weakened as compared with bortezomib alone, indicating that the inhibitory activity of bortezomib was inactivated. For 32, the present results were consistent with a previous report stating that 32 was not significantly inhibited by bortezomib (Kisselev, A. F. et al., Chemistry & Biology, 2012, 19, 99-115). Further, the inhibitory activity of TMP-CiKD_Bortezomib against β2 and β5 was found to be increased in a concentration dependent manner, indicating that TMP-CiKD_Bortezomib had an affinity with a proteasome.

Example 5

Measurement of 50% Inhibition Concentration (IC$_{50}$) of Protein-Degradation Inducing Molecule (TMP-CiKD_Bortezomib)

In Example 5, 50% inhibition concentrations (IC$_{50}$) of TMP-CiKD_Bortezomib and bortezomib (Code No. sc-217785, Santa Cruz Biotechnology) were measured for each of the proteasome activities of β1, β2, and β5 of 20S proteasome.

For the 50% inhibition concentration (IC$_{50}$), AMC released when the C-terminus of an AMC-conjugated proteasome fluorescent substrate specific to a β subunit of β5 (chymotrypsin-like activity), β2 (trypsin-like activity), and β1 (caspase-like activity) of 20S proteasome was cut using 20S Proteasome StressXpress™ Assay Kit Gold (Bioscience) was measured with a multi-detection microplate reader (Synergy HT, BIO-TEK). The measurement wavelengths were 360 nm for excitation light (Ex.), and 460 nm for fluorescence (Em.).

Test compounds (TMP-CiKD_Bortezomib and bortezomib) were each adjusted to 6 concentrations as shown in the following Table 83.

TABLE 83

| TMP-CiKD_Bortezomib | β1: 1, 4, 10, 40, 80, 160 μM |
| | β2: 1, 4, 10, 40, 80, 160 μM |
| | β5: 1, 4, 10, 40, 80, 160 μM |
| Bortezomib | β1: 0.01, 0.04, 0.1, 0.4, 1, 10 μM |
| | β2: 0.4, 1, 4, 10, 40, 100 μM |
| | β5: 0.001, 0.004, 0.01, 0.04, 0.1, 0.4 μM |

A test compound and 20S proteasome (0.1 μg) were incubated at room temperature for 30 minutes. To these, Suc-LLVY-AMC (degradable by β5), Bz-VGR-AMC (degradable by β2), and Z-LLE-AMC (degradable by β1) as a luminescent substrates were added so that the concentrations thereof were each 100 μM, and incubated at room temperature. After one hour, AMC produced by the proteasome activity was measured. Values of proteasome degradation inhibition of the test compounds at each concentration were calculated as relative values to the control (DMSO). Using the inhibition values at the 6 concentrations, a regression curve was created with an analysis software ImageJ (NIH) to obtain 4 parameters (a: Malthusian parameter, b: crowdedness constant, c: slope, d: intercept). Then, the obtained 4 parameters and y=0.5 (50% inhibition) were introduced into the following regression expression of 4-parameter logistic curve, and a value of x (IC$_{50}$) was computed.

Regression expression of 4-parameter logistic curve:
$$y=d+(a-d)/(1+(x/c)^b)$$

The 50% inhibition concentrations (IC$_{53}$) of TMP-CiKD_Bortezomib and bortezomib are shown in the following Table 84.

TABLE 84

| | IC$_{50}$ (μM) | | |
| --- | --- | --- | --- |
| | β1 | β2 | β5 |
| TMP-CiKD_Bortezomib | >160 | >160 | >160 |
| Bortezomib | 0.129 | 2.61 | 0.00314 |

As can be seen in Table 84, TMP-CiKD_Bortezomib was found to have significantly increased 50% inhibition concentrations (IC$_{50}$) against all of β1, β2, and β5 as compared with bortezomib, indicating that the inhibitory activity of bortezomib was inactivated.

Example 6

Synthesis of Protein-Degradation Inducing Molecule (TMP-CiKD_ALLN) Using CiKD_ALLN as Protein-Degradation Inducing Tag and TMP Derivative as Protein Binding Molecule In Example 6, TMP-CiKD_ALLN as a protein-degradation inducing molecule was synthesized according to the following synthesis scheme. As a protein-degradation inducing tag, used was ALLN-COOH (CiKD_ALLN) in which the formyl group as the active site of ALLN was replaced with a carboxy group. As a protein binding molecule, TMP-NH$_2$ was used as in Example 1. Then, ALLN-COOH was linked to TMP-NH$_2$ to synthesize TMP-CiKD_ALLN as a protein-degradation inducing molecule.

10/1, gradient) to obtain a compound 6 (ALLN-COOH) (27.0 mg, 0.068 mmol, 30%).

(Synthesis of Compound 7 (TMP-CiKD_ALLN))

The compound 6 (ALLN-COOH) (26.8 mg, 0.067 mmol, 1 eq) and TMP-NH$_2$ synthesized separately (Long, M. J. et al., Chem. Biol., 2012, 19 (5) 629-637) (26.0 mg, 0.060

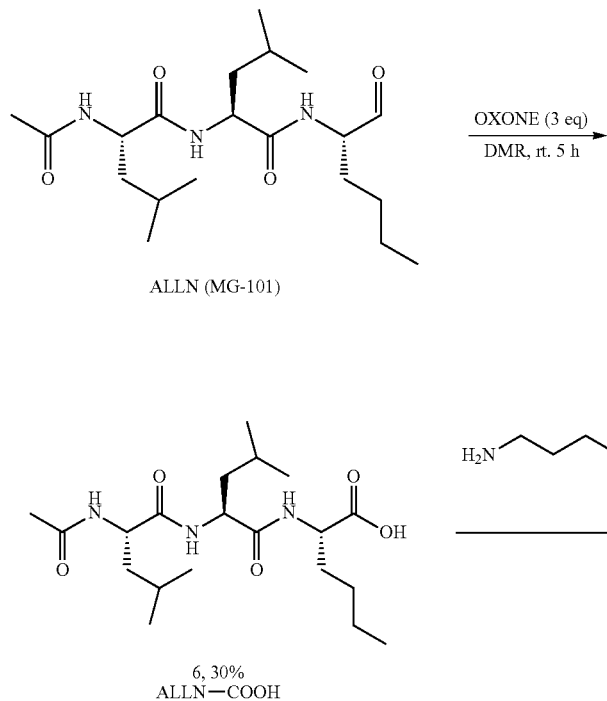

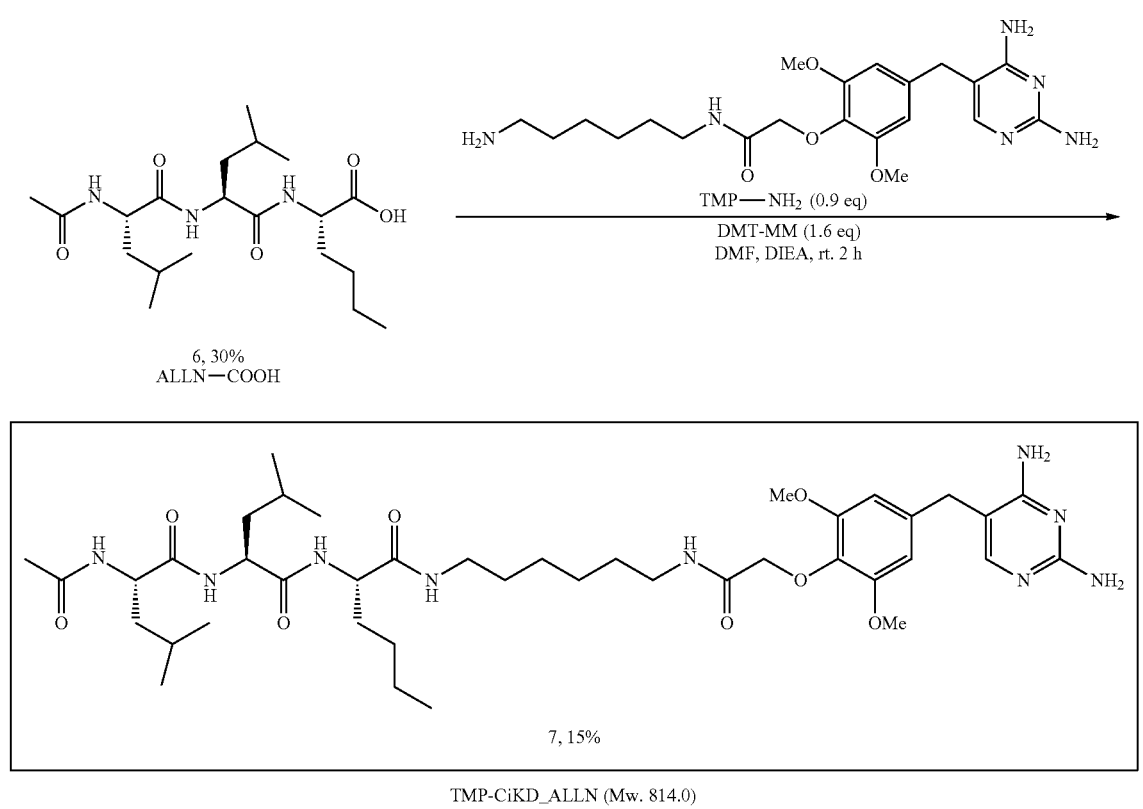

TMP-CiKD_ALLN (Mw. 814.0)

The method of synthesizing TMP-CiKD_ALLN is described in detail as follows.

(Synthesis of Compound 6 (ALLN-COOH)>

ALLN (87.2 mg, 0.23 mmol, 1 eq, Code No. 07036-24, Nacalai Tesque, Inc.) was charged into an eggplant flask, and 2 mL of dehydrate DMF was added. After stirred at room temperature for 5 minutes, Oxone (212.1 mg, 0.69 mmol, 3 eq, Code No. 228036, Sigma-Aldrich) was added directly to the reaction solution, and stirred at room temperature for 5 hours. The reaction solution was diluted with water, and extracted with chloroform for 3 times. After dried over anhydrous sodium sulfate, the solvent was evaporated under reduced pressure. Separation and purification treatment was performed by silica gel chromatography (Code No. 30511-35, Nacalai Tesque, Inc.) (chloroform/methanol=20/1 to mmol, 0.9 eq) was charged into an eggplant flask, and 2 mL of dehydrate DMF was added. After stirred at room temperature for 5 minutes, 0.1 mL of DIEA was added to neutralize the solution. After stirred at room temperature for 5 minutes, DMT-MM (30.0 mg, 0.11 mmol, 1.6 eq, Code No. 329-53751, Wako Pure Chemical Industries, Ltd.) was added directly to the reaction solution, and stirred at room temperature for 2 hours. Under cooling conditions, 10 mL of 10 mass % brine/0.1 N aqueous hydrochloric acid was added, and extracted with ethyl acetate for 3 times. This was washed with 0.5 N aqueous hydrochloric acid and then brine, and then dried over anhydrous sodium sulfate. After evaporating the solvent under reduced pressure, separation and purification treatment was performed by silica gel chromatography (Code No. 30511-35, Nacalai Tesque, Inc.) (chloroform/methanol=10/1) to obtain a compound 7 (TMP-CiKD_ALLN) (8.2 mg, 0.010 mmol, 15%, isolated yield).

Example 7

Evaluation (FACS Analysis) of Degradation (Knockdown) of Forcedly Expressed Target Protein (*E. coli* DHFR) in HeLa Cells to which Protein-Degradation Inducing Molecule (TMP-CiKD_ALLN) was Added In Example 7, degradation (knockdown) of a forcedly expressed target protein (*E. coli* DHFR) in HeLa cells to which TMP-CiKD_ALLN was added was evaluated by FACS analysis.
(Preparation of Cultured Cells, Introduction of Plasmid into HeLa Cells, and Cell Seeding)

HeLa cells were prepared as in Example 2. A plasmid (pMIR DsRed-IRES-ecDHFR-HA-GFP) was introduced into HeLa cells as in Example 2, and then seeded on a 24-well plate.
(Addition of Protein-Degradation Inducing Molecule (TMP-CiKD_ALLN) to HeLa Cells)

TMP-CiKD_ALLN was added to HeLa cells as in Example 2 except that TMP-CiKD_ALLN was used in place of TMP-CiKD_Bortezomib. A DMSO solution containing TMP or DMSO was used as a control in place of the DMSO solution containing TMP-CiKD_ALLN.
(Evaluation of Target Degradation (Knockdown) Due to TMP-CiKD_ALLN by FACS Analysis)

The efficiency of target degradation (knockdown) by TMP-CiKD_ALLN was determined as in Example 2 except that TMP-CiKD_ALLN was used in place of TMP-CiKD_Bortezomib.

Figure 5A:
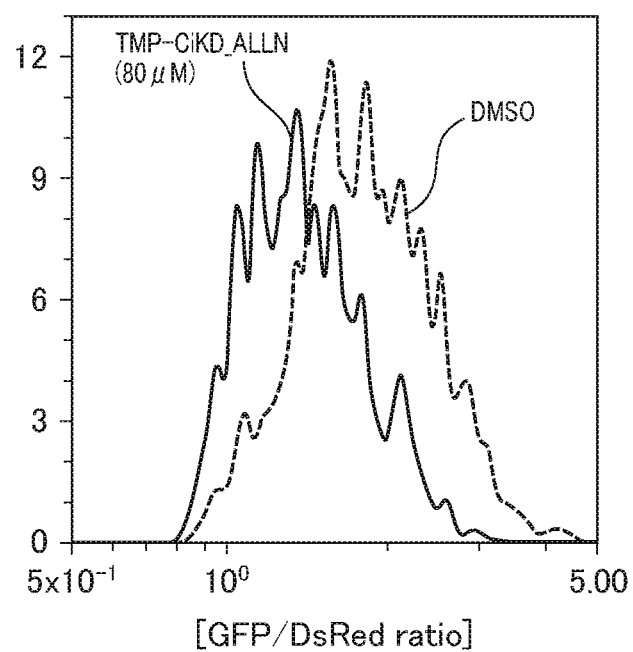
FIG. 5A shows results from the FACS analysis of a forcedly expressed target protein (*E. coli* DHFR) in HeLa cells to which TMP-CiKD_ALLN was added.
Figure 5B:
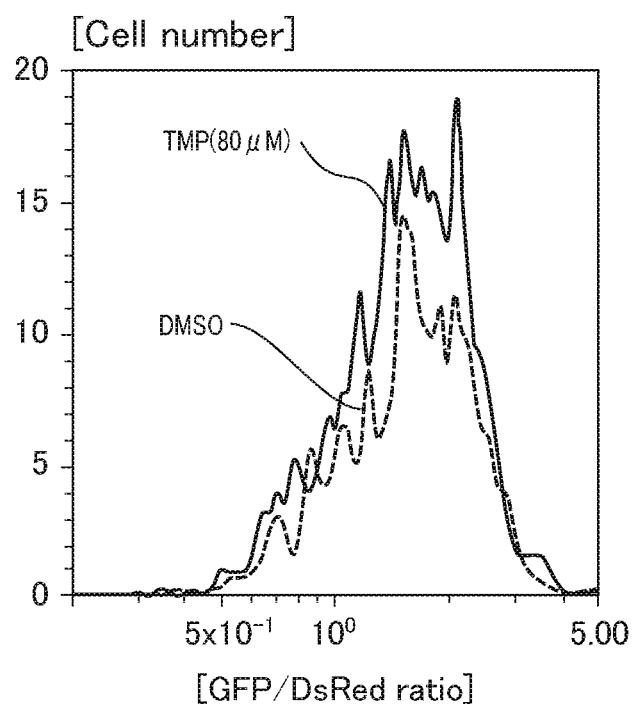
FIG. 5B shows results from the FACS analysis of a forcedly expressed target protein (*E. coli* DHFR) in HeLa cells to which TMP was added.

FIG. 5A shows results from the FACS analysis of a forcedly expressed target protein (*E. coli* DHFR) in HeLa cells to which TMP-CiKD_ALLN was added. Further, FIG. 5B shows results from the FACS analysis of a forcedly expressed target protein (*E. coli* DHFR) in HeLa cells to which TMP was added. As can be seen in FIG. 5A, when TMP-CiKD_ALLN (80 μM) was added, the graph was found to be significantly shifted to the left as compared with that of the control (DMSO), indicating that the target protein (*E. coli* DHFR) was degraded. The degradation efficiency estimated from the amount of a shift was about 60% to 70%. In contrast, as can be seen in FIG. 5B, when TMP (80 μM) was added, the graph was found to be overlapped with that of the control (DMSO), indicating that the target protein was not degraded.

Example 8

Evaluation (Thermal Shift Assay) of Affinity of Protein-Degradation Inducing Molecule (TMP-CiKD_ALLN) with Forcedly Expressed Target Protein (*E. coli* DHFR) in HeLa Cells to which Protein-Degradation Inducing Molecule (TMP-CiKD_ALLN) was Added In Example 8, the affinity of TMP-CiKD_ALLN with a forcedly expressed target protein (*E. coli* DHFR) in HeLa cells to which TMP-CiKD_ALLN was added was evaluated by thermal shift assay.
(Preparation of Cultured Cells, Introduction of Plasmid into HeLa Cells, and Cell Seeding)

HeLa cells were prepared as in Example 2. A plasmid (pMIR DsRed-IRES-ecDHFR-HA-GFP) was introduced into HeLa cells as in Example 2, and then seeded on a 24-well plate.
(Addition of Protein-Degradation Inducing Molecule (TMP-CiKD_ALLN) to HeLa Cells)

TMP-CiKD_ALLN was added to HeLa cells as in Example 2 except that TMP-CiKD_ALLN was used in place of TMP-CiKD_Bortezomib. A DMSO solution containing TMP or DMSO was used as a control in place of the DMSO solution containing TMP-CiKD_ALLN.
(Evaluation of Affinity of TMP-CiKD_ALLN with Target by Thermal Shift Assay)

The affinity of TMP-CiKD_ALLN with a target was evaluated by thermal shift assay as in Example 3 except that TMP-CiKD_ALLN was used in place of TMP-CiKD_Bortezomib.

Figure 6:
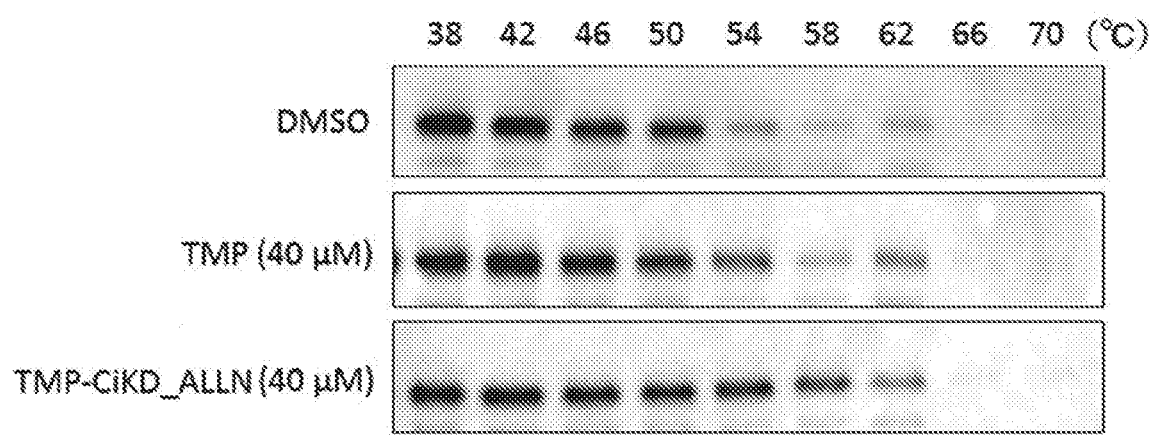
FIG. 6 shows results from the thermal shift assay of a forcedly expressed target protein (*E. coli* DHFR) in HeLa cells to which TMP-CiKD_ALLN or TMP was added.

FIG. 6 shows results from the thermal shift assay of a forcedly expressed target protein (*E. coli* DHFR) in HeLa cells to which TMP-CiKD_ALLN or TMP was added. As shown in FIG. 6, *E. coli* DHFR was able to be detected only up to about 50° C. for the control (DMSO). In contrast, *E. coli* DHFR was able to be detected up to about 54° C. by virtue of interaction between *E. coli* DHFR and TMP when TMP (40 μM) was added. Similarly, *E. coli* DHFR was able to be detected up to about 58° C. by virtue of interaction between *E. coli* DHFR and TMP-CiKD_ALLN when TMP-CiKD_ALLN (40 μM) was added. These results show that TMP-CiKD_ALLN, in which TMP-NH$_2$ is linked to CiKD_ALLN, has a higher affinity with *E. coli* DHFR than TMP.

Example 9

Evaluation of Proteasome Inhibitory Activity of Protein-Degradation Inducing Molecule (TMP-CiKD_ALLN) and Affinity Thereof with Proteasome In Example 9, the proteasome inhibitory activity of TMP-CiKD_ALLN, and the affinity of TMP-CiKD_ALLN with a proteasome were evaluated as in Example 4 except that TMP-CiKD_ALLN was used in place of TMP-CiKD_Bortezomib.

Figure 7A:
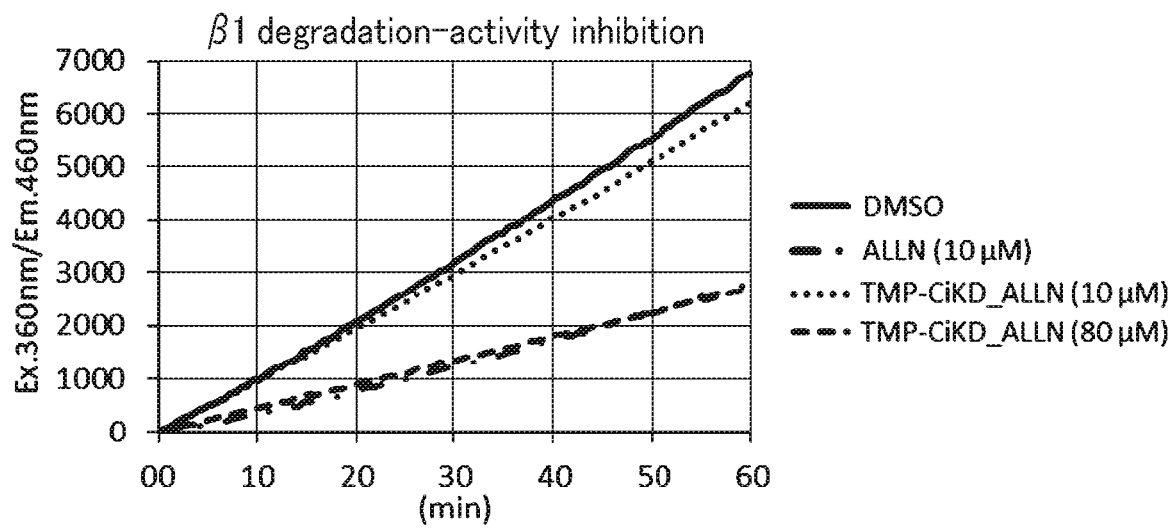
FIG. 7A shows the inhibitory activity of TMP-CiKD_ALLN and ALLN against the catalytic subunit β1 of the proteasome.
Figure 7B:
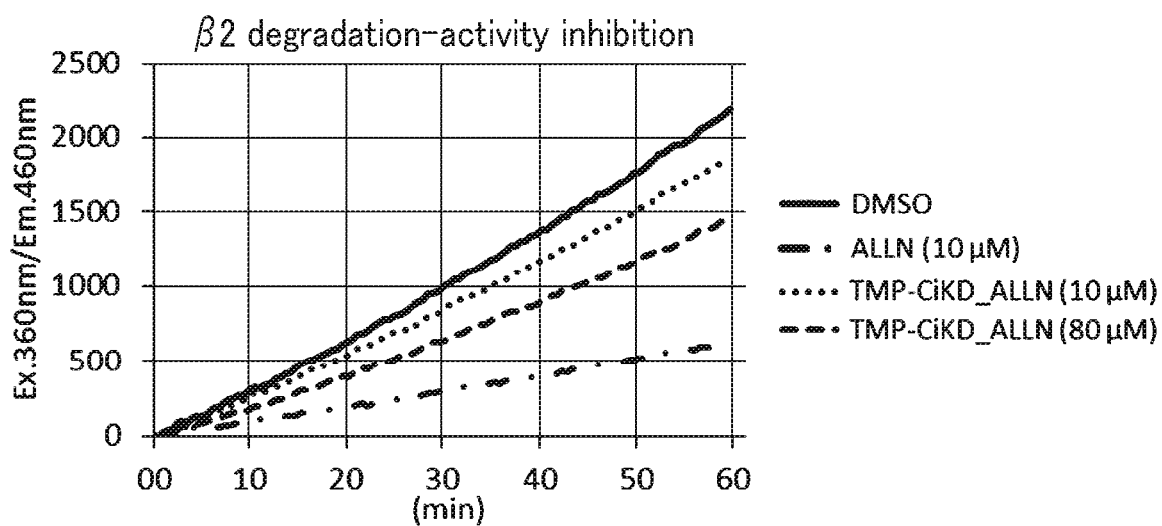
FIG. 7B shows the inhibitory activity of TMP-CiKD_ALLN and ALLN against the catalytic subunit β2 of the proteasome.
Figure 7C:
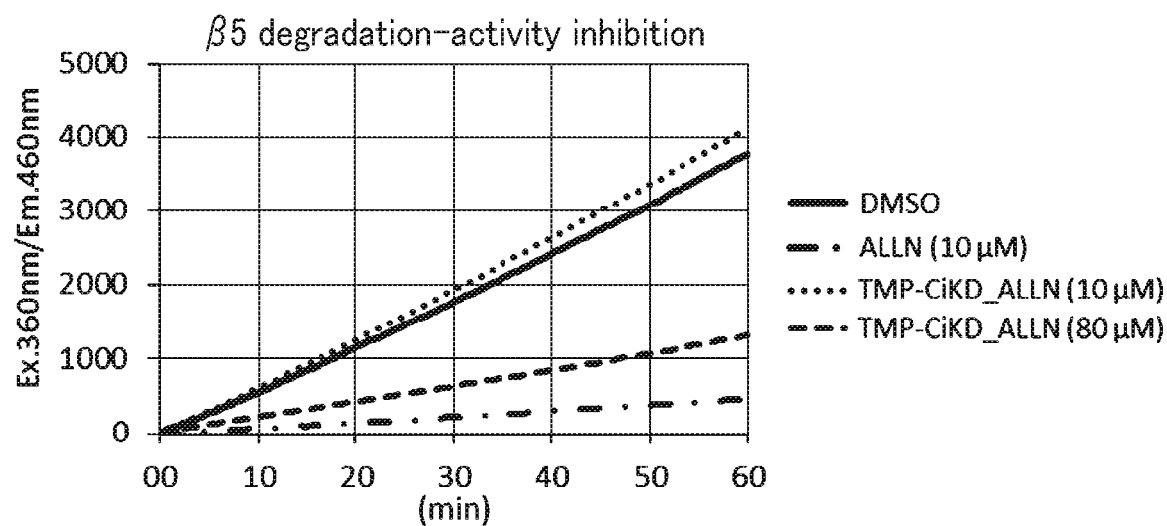
FIG. 7C shows the inhibitory activity of TMP-CiKD_ALLN and ALLN against the catalytic subunit (5 of the proteasome.

FIGS. 7A to 7C show the proteasome activities against β1 (caspase-like activity), β2 (trypsin-like activity), and β5 (chymotrypsin-like activity), respectively. As can be seen in FIGS. 7A to 7C, the inhibitory activity of TMP-CiKD_ALLN against β2 and β5 was found to be weakened as compared with ALLN alone, indicating that the activity of ALLN was inactivated. For β1, the present results were consistent with a previous report stating that β1 was not significantly inhibited by ALLN (Kaiser, M. et al., Chem. Bio. Chem., 2004, 5, 1256-1266). Further, the inhibitory activity of TMP-CiKD_ALLN was found to be increased against any of β1, β2, and β5 in a concentration dependent manner, indicating that TMP-CiKD_ALLN had an affinity with a proteasome.

Example 10

Measurement of 50% Inhibition Concentration (IC$_{50}$) of Protein-Degradation Inducing Molecule (TMP-CiKD_ALLN)

In Example 10, the 50% inhibition concentrations (IC$_{50}$) of TMP-CiKD_ALLN and ALLN (Code No. 07036-82, Nacalai Tesque, Inc.) were measured for each of the proteasome activities of β1, β2, and β5 of 20S proteasome as in Example 5 except that TMP-CiKD_ALLN and ALLN were used in place of TMP-CiKD_Bortezomib and bortezomib. It is noted that test compounds (TMP-CiKD_ALLN and ALLN) were each adjusted to 6 concentrations as shown in the following Table 85.

TABLE 85

| TMP-CiKD_ALLN | β1: 5, 10, 20, 40, 80, 160 μM |
| --- | --- |
| | β2: 5, 10, 20, 40, 80, 160 μM |
| | β5: 5, 10, 20, 40, 80, 160 μM |
| ALLN | β1: 0.4, 1, 4, 10, 20, 40 μM |
| | β2: 0.4, 1, 4, 10, 20, 40 μM |
| | β5: 0.04, 0.1, 0.4, 1.4, 10 μM |

The 50% inhibition concentrations (IC$_5$s) of TMP-CiKD_ALLN and ALLN are shown in the following Table 86.

TABLE 86

| | IC$_{50}$ (μM) | | |
| --- | --- | --- | --- |
| | β1 | β2 | β5 |
| TMP-CiKD_ALLN | 38.8 | >160 | 42.3 |
| ALLN | 12.4 | 5.25 | 1.15 |

As can be seen in Table 86, TMP-CiKD_ALLN was found to have significantly increased 50% inhibition concentrations (IC$_5$s) for all of 01, (2, and 05 as compared with ALLN, indicating that the inhibitory activity of ALLN was inactivated.

Example 11

Synthesis of Protein-Degradation Inducing Molecule (TMP-CiKD_MLN) Using CiKD_MLN as Protein-Degradation Inducing Tag and TMP Derivative as Protein Binding Molecule In Example 11, TMP-CiKD_MLN as a protein-degradation inducing molecule was synthesized according to the following synthesis scheme. As a protein-degradation inducing tag, used was MLN-COOH (CiKD_MLN) in which the boronic acid ester moiety or boronyl group as the active site of MLN9708 and MLN2238 was replaced with a carboxy group. As a protein binding molecule, TMP-NH$_2$ was used as in Example 1. Then, MLN-COOH was linked to TMP-NH$_2$ to synthesize TMP-CiKD_MLN as a protein-degradation inducing molecule.

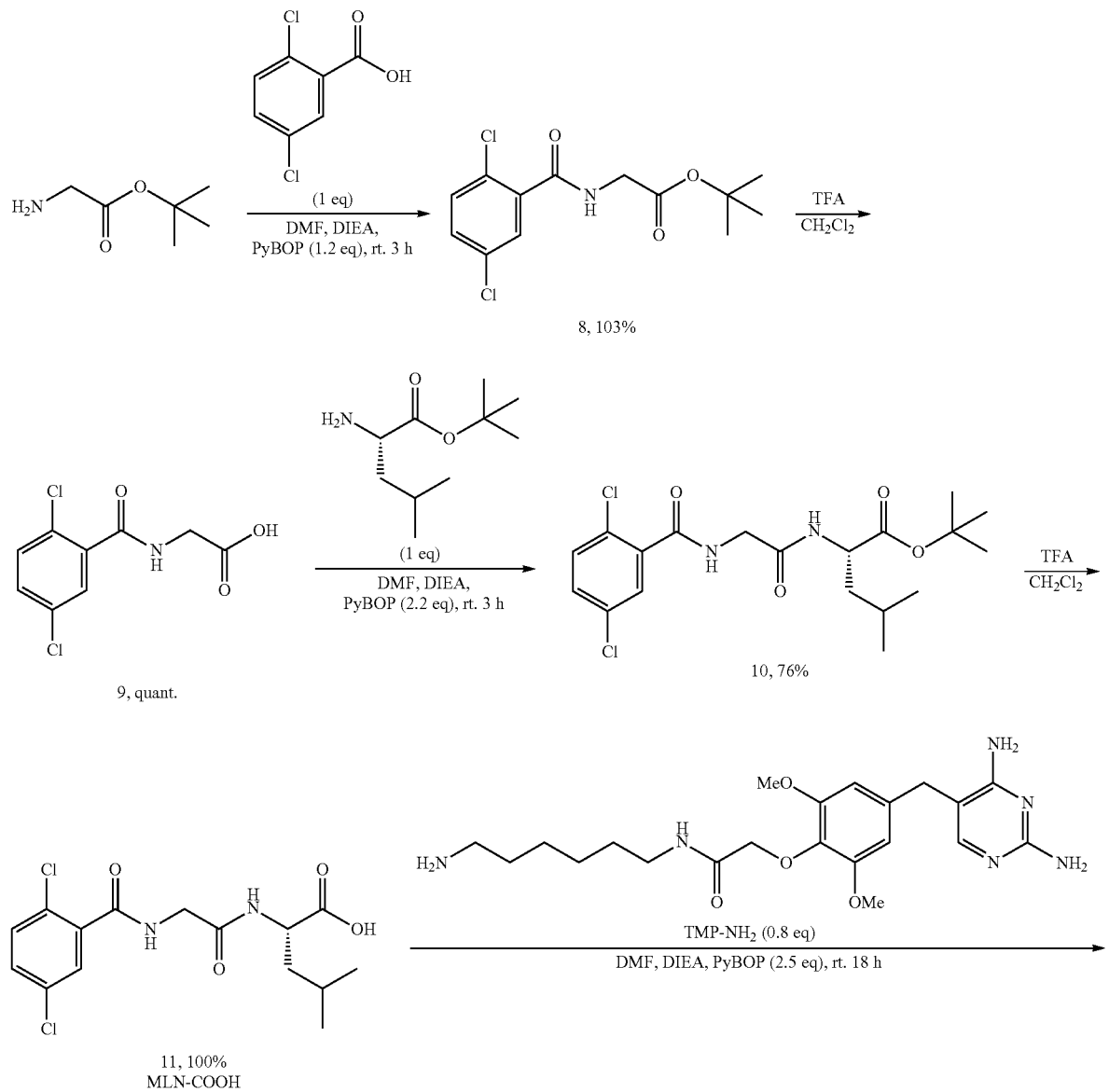

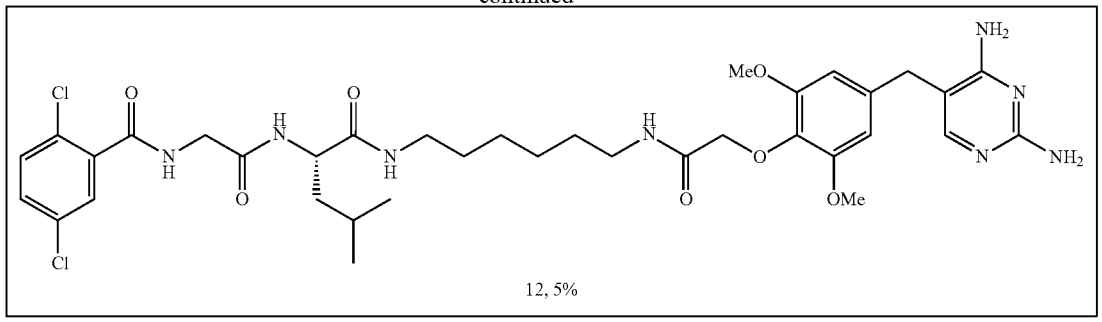

TMP-CiKD_MLN (Mw. 775.7)

The method of synthesizing TMP-CiKD_MLN is described in detail as follows.
(Synthesis of Compound 8)

H-Gly-OtBu.HCl (286.8 mg, 1.69 mmol, 1 eq, Code No. AK-46074, Ark Pharm) was charged into a side-arm eggplant flask, and purged with nitrogen. Under nitrogen gas stream, 10 mL of dehydrate DMF and 5 mL of DIEA were added, and stirred at room temperature. In 1 mL of dehydrate DMF and 1 mL of DIEA, dissolved was 2,5-dichlorobenzoic acid (309.3 mg, 1.62 mmol, 1 eq, Code No. AK-47665, Ark Pharm), which was then added to the reaction solution, and stirred at room temperature for 20 minutes. PyBOP (1.02 g, 1.96 mmol, 1.2 eq, Code No. 8.51009.0005, Novabiochem, Merck) was dissolved in 1 mL of dehydrate DMF, and then added to the reaction solution, and stirred at room temperature for 3 hours. The reaction solution was diluted with water and aqueous sodium hydrogen carbonate, and extracted twice with ethyl acetate/hexane (=4/1). After dried over anhydrous sodium sulfate, the solvent was evaporated under reduced pressure. Separation and purification treatment was performed by silica gel chromatography (Code No. 30511-35, Nacalai Tesque, Inc.) (hexane/chloroform=1/1 to 0/1, gradient) to obtain a compound 8 (531.0 mg, 1.75 mmol, 103%).
(Synthesis of Compound 9)

The compound 8 (212.4 mg, 0.70 mmol) was charged into an eggplant flask, and 5 mL of dichloromethane was then added. This was stirred at room temperature for 5 minutes, and then 5 mL of TFA was added, and stirred at room temperature for 1 hour. After evaporating the solvent under reduced pressure, vacuum drying was performed to obtain a compound 9 (190.7 mg, quant.).
(Synthesis of Compound 10)

The compound 9 (190.7 mg, 0.77 mmol, 1 eq) and H-Leu-OtBu.HCl (175.8 mg, 0.79 mmol, 1 eq, Code No. 14G110356, Watanabe Chemical Industries, Ltd.) were charged into a side-arm eggplant flask, and purged with nitrogen. Under nitrogen gas stream, 5 mL of dehydrate DMF and 5 mL of DIEA were added, and stirred at room temperature for 20 minutes. PyBOP (886.7 mg, 1.70 mmol, 2.2 eq, Code No. 8.51009.0005, Novabiochem, Merck) was dissolved in 1.5 mL of dehydrate DMF, and added to the reaction solution, and stirred at room temperature for 3 hours. The reaction solution was diluted with water and aqueous sodium hydrogen carbonate, and extracted twice with ethyl acetate/hexane (=4/1). After dried over anhydrous sodium sulfate, the solvent was evaporated under reduced pressure. Separation and purification treatment was performed by silica gel chromatography (Code No. 30511-35, Nacalai Tesque, Inc.) (hexane/chloroform=1/1 to 0/1, gradient) to obtain a compound 10 (244.2 mg, 0.58 mmol, 76%).
(Synthesis of Compound 11 (MLN-COOH)

The compound 10 (240.8 mg, 0.58 mmol) was charged into an eggplant flask, and 5 mL of dichloromethane was added. This was stirred at room temperature for 5 minutes, and then 5 mL of TFA was added, and stirred at room temperature for 1 hour. After evaporating the solvent under reduced pressure, vacuum drying was performed to obtain a compound 11 (MLN-COOH) (214.7 mg, 0.59 mmol, 100%).
(Synthesis of Compound 12 (TMP-CiKD_MLN))

The compound 11 (MLN-COOH) (210.3 mg, 0.58 mmol, 1 eq) was charged into a side-arm eggplant flask, and purged with nitrogen. TMP-NH$_2$ synthesized separately (Long, M. J. et al., Chem. Biol., 2012, 19 (5), 629-637) (207.6 mg, 0.48 mmol, 0.8 eq) was dissolved in 5 mL of dehydrate DMF, and added to the reaction solution. To this, 5 ml of DIEA was added, and stirred at room temperature for 20 minutes. PyBOP (765.2 mg, 1.47 mmol, 2.5 eq, Code No. 8.51009.0005, Novabiochem, Merck) was dissolved in 1.5 mL of dehydrate DMF, and then added to the reaction solution, and stirred at room temperature for 18 hours. The reaction solution was diluted with water and aqueous sodium hydrogen carbonate, and extracted twice with ethyl acetate. After dried over anhydrous sodium sulfate, the solvent was evaporated under reduced pressure, and separation and purification treatment was performed by silica gel chromatography (Code No. 30511-35, Nacalai Tesque, Inc.) (chloroform/methanol=20/1 to 4/1, gradient). Subsequently, separation and purification treatment was performed using a TLC silica gel 60 (Code No. HX264817, Merck) (chloroform/methanol=10/1) to obtain a compound 12 (TMP-CiKD_MLN) (20.2 mg, 0.026 mmol, 5%, isolated yield).

Example 12

Evaluation (FACS Analysis) of Degradation (Knockdown) of Forcedly Expressed Target Protein (*E. coli* DHFR) in HeLa Cells to which Protein-Degradation Inducing Molecule (TMP-CiKD_MLN) was Added In Example 12, degradation (knockdown) of a forcedly expressed target protein (*E. coli* DHFR) in HeLa cells to which TMP-CiKD_MLN was added was evaluated by FACS analysis.
(Preparation of Cultured Cells, Introduction of Plasmid into HeLa Cells, and Cell Seeding)

HeLa cells were prepared as in Example 2. A plasmid (pMIR DsRed-IRES-ecDHFR-HA-GFP) was introduced into HeLa cells as in Example 2, and then seeded on a 24-well plate.

(Addition of Protein-Degradation Inducing Molecule (TMP-CiKD_MLN) to HeLa Cells)

TMP-CiKD_MLN was added to HeLa cells as in Example 2 except that TMP-CiKD_MLN was used in place of TMP-CiKD_Bortezomib. Further, an experiment group where a DMSO solution containing TMP-CiKD_MLN and bortezomib was added was also prepared in addition to an experiment group where a DMSO solution containing TMP-CiKD_MLN was added. A DMSO solution containing TMP or DMSO was used as a control in place of the DMSO solution containing TMP-CiKD_MLN.

(Evaluation of Target Degradation (Knockdown) Due to TMP-CiKD_MLN by FACS Analysis)

The efficiency of target degradation (knockdown) by TMP-CiKD_MLN was determined as in Example 2 except that TMP-CiKD_MLN or TMP-CiKD_MLN and bortezomib were used in place of TMP-CiKD_Bortezomib.

Figure 8A:
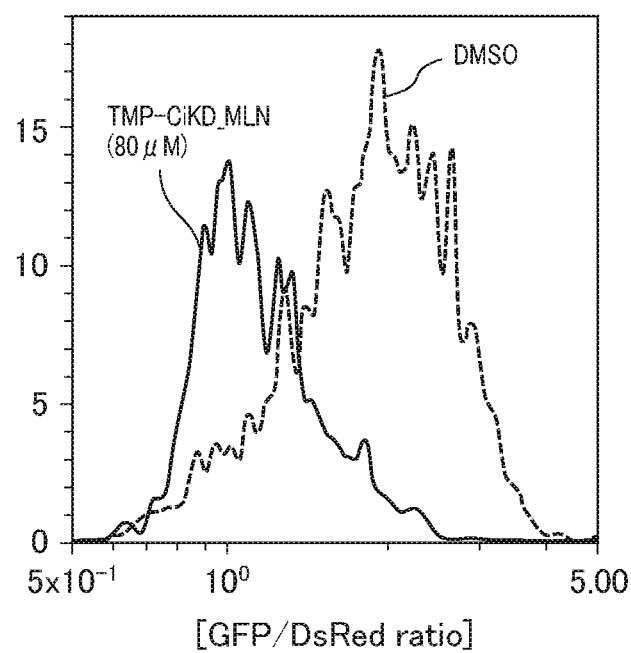
FIG. 8A shows results from the FACS analysis of a forcedly expressed target protein (*E. coli* DHFR) in HeLa cells to which TMP-CiKD_MLN was added.
Figure 8B:
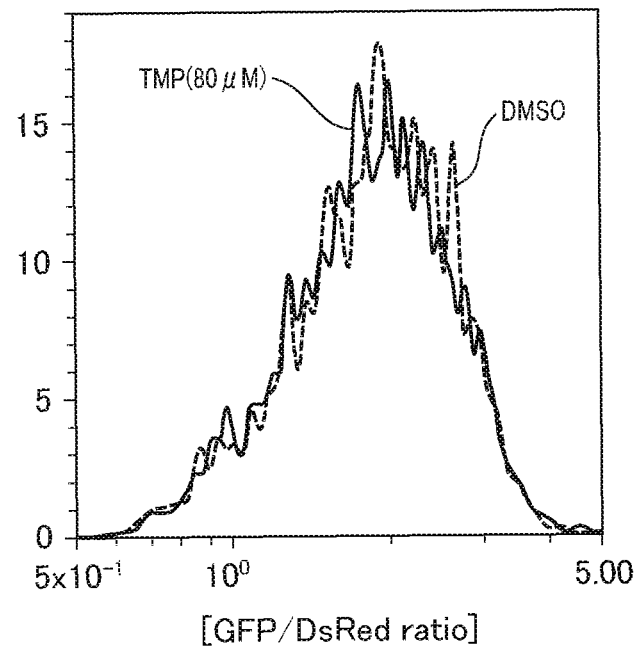
FIG. 8B shows results from the FACS analysis of a forcedly expressed target protein (*E. coli* DHFR) in HeLa cells to which TMP was added.
Figure 8C:
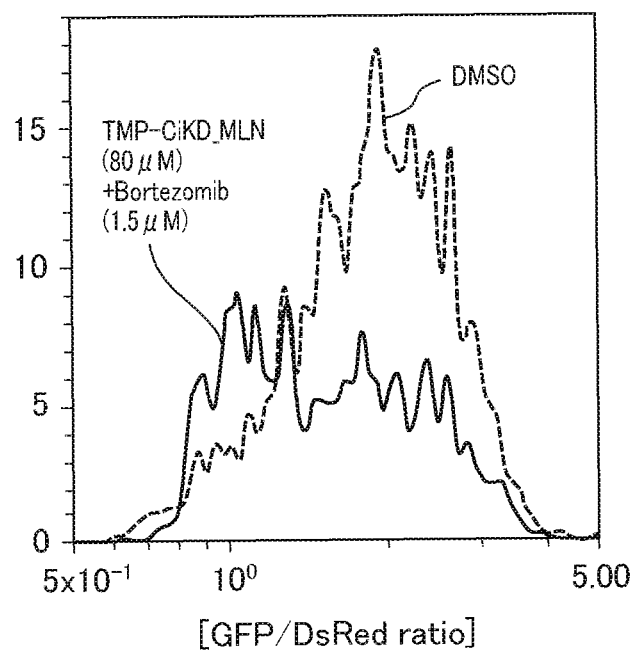
FIG. 8C shows results from the FACS analysis of a forcedly expressed target protein (*E. coli* DHFR) in HeLa cells to which TMP-CiKD_MLN and Bortezomib were added.

FIG. 8A shows results from the FACS analysis of a forcedly expressed target protein (*E. coli* DHFR) in HeLa cells to which TMP-CiKD_MLN was added. Further, FIG. 8B shows results from the FACS analysis of a forcedly expressed target protein (*E. coli* DHFR) in HeLa cells to which TMP was added. Moreover, FIG. 8C shows results from the FACS analysis of a forcedly expressed target protein (*E. coli* DHFR) in HeLa cells to which TMP-CiKD_MLN and bortezomib were added. As can be seen in FIG. 8A, when TMP-CiKD_MLN (80 μM) was added, the graph was found to be significantly shifted to the left as compared with that of the control (DMSO), indicating that the target protein (*E. coli* DHFR) was degraded. The degradation efficiency estimated from the amount of a shift was about 60% to 70%. In contrast, as can be seen in FIG. 8B, when TMP (80 μM) was added, the graph was found to be overlapped with that of the control (DMSO), indicating that the target protein was not degraded. Moreover, as shown in FIG. 8C, when TMP-CiKD_MLN (80 μM) and bortezomib (1.5 μM) were added, degradation of the target protein was more significantly inhibited than a case where TMP-CiKD_MLN (80 μM) was added. These results suggest that TMP-CiKD_MLN enabled the target protein to lead to degradation by the proteasome.

Example 13

Synthesis of Protein-Degradation Inducing Molecule (MTX-CiKD_MLN) Using CiKD_MLN as Protein-Degradation Inducing Tag and MTX Derivative as Protein Binding Molecule In Example 13, MTX-CiKD_MLN as a protein-degradation inducing molecule was synthesized according to the following synthesis scheme. As a protein-degradation inducing tag, used was MLN-COOH (CiKD_MLN) in which the boronic acid ester moiety or boronyl group as the active site of MLN9708 and MLN2238 was replaced with a carboxy group. As a protein binding molecule, used was an MTX derivative (MTX-NH₂) in which a functional group including an amino group was introduced into MTX as a dihydrofolate reductase inhibitor capable of binding to DHFR. Then, MLN-COOH was linked to MTX-NH₂ to synthesize MTX-CiKD_MLN as a protein-degradation inducing molecule.

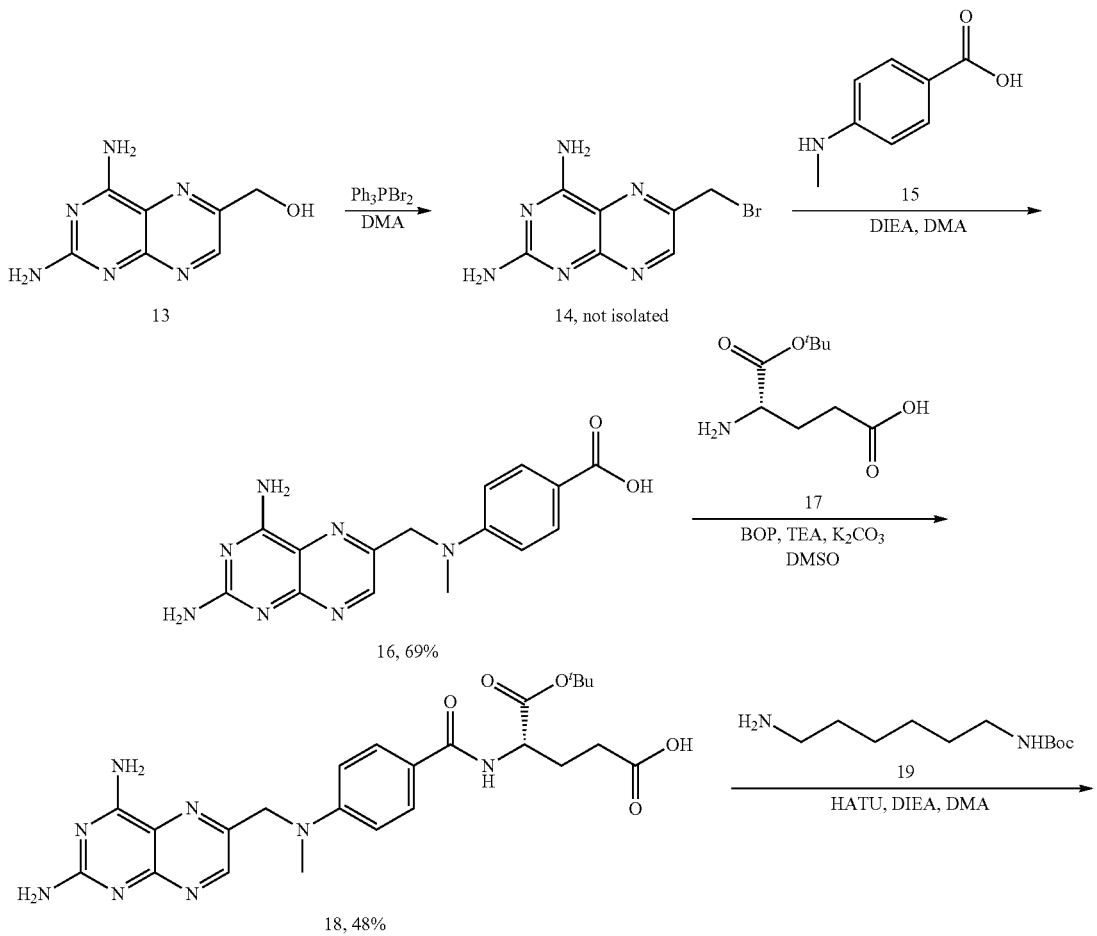

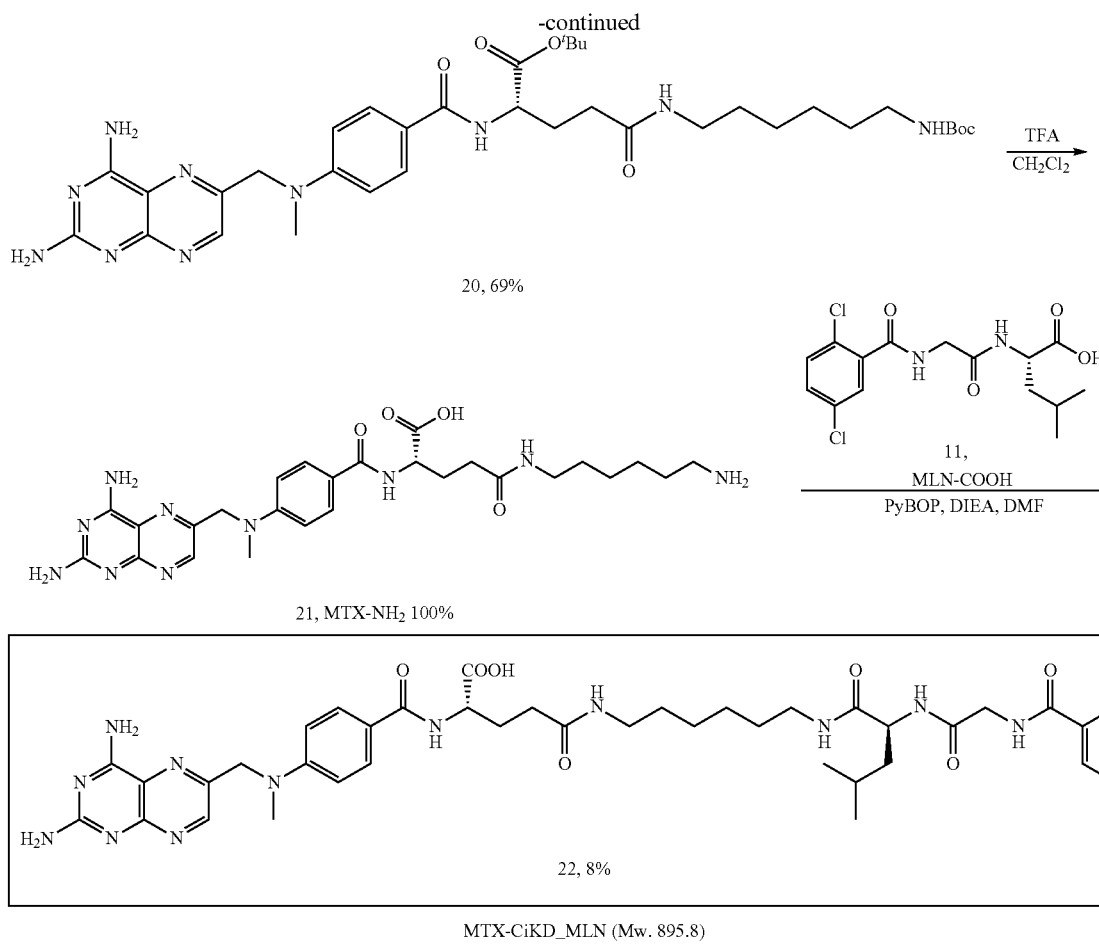

The method of synthesizing MTX-CiKD_MLN is described in detail as follows.
(Synthesis of Compound 21 (MTX-NH₂))

The compound 13 was allowed to react with triphenylphosphine dibromide in DMA to obtain a compound 14. The compound 14 was dissolved in DMA under nitrogen gas stream, and then the compound 15 and DIEA were added and reacted to obtain a compound 16 (yield: 69%). Subsequently, the compound 16 and the compound 17 were dissolved in DMSO under nitrogen gas stream, and condensation reaction was performed with a BOP reagent to obtain a compound 18 (yield: 46%). Subsequently, the compound 18 and the compound 19 were dissolved in DMA under nitrogen gas stream, and condensation reaction was performed with HATU to obtain a compound 20 (yield: 69%). Then, the compound 20 was dissolved in dichloromethane, and deprotection was performed with TFA to obtain a compound 21 (MTX-NH₂).
(Synthesis of Compound 22 (MTX-CiKD_MLN))

The compound 21 (MTX-NH₂) and the compound 11 used for synthesis of the compound 12 (TMP-CiKD_MLN) were dissolved in DMF under nitrogen gas stream, and a condensation reaction was performed with PyBOP (at room temperature for 3 hours). The reaction solution was diluted with water and aqueous sodium hydrogen carbonate, and extracted with ethyl acetate for 3 times. After dried over anhydrous sodium sulfate, the solvent was evaporated under reduced pressure, and separation and purification treatment was performed by silica gel chromatography (chloroform/methanol=20/1 to 4/1, gradient). Subsequently, separation and purification treatment was performed using a TLC silica gel 60 (chloroform/methanol=85/15) to obtain a compound 22 (MTX-CiKD_MLN) (isolated yield: 8%).

Example 14

Evaluation (Thermal Shift Assay) of the Affinity of a Protein-Degradation Inducing Molecule (MTX-CiKD_MLN) with Endogenously Expressed Target Protein (Human DHFR) in HeLa Cells to which a Protein-Degradation Inducing Molecule MTX-CiKD_MLN was Added In Example 14, the affinity of MTX-CiKD_MLN with an endogenously expressed target protein (human DHFR) in HeLa cells to which MTX-CiKD_MLN was added was evaluated by thermal shift assay.
(Preparation of Cultured Cells and Cell Seeding)

HeLa cells were prepared as in Example 2. The cell solution collected after trypsin treatment was seeded on a 24-well plate (Code No. TR5002, TrueLine, Nippon Genetics Co., Ltd.) at a cell density of $4 \times 10^4$ cells/800 µL/well, and then cultured under conditions of 37° C. and 5 vol % $CO_2$ for 16 hours.
(Addition of Protein-Degradation Inducing Molecule (MTX-CiKD_MLN) to HeLa Cells)

MTX-CiKD_MLN was added to HeLa cells as follows 16 hours after cell seeding. As a medium, used was a serum free medium (37° C.) in which a 1 mass % L-glutamine solution (Code No. G7513, Sigma-Aldrich) was added to D-MEM (high D-glucose, phenol red, sodium pyruvate (Code No. 045-32245, Wako Pure Chemical Industries, Ltd.). It is noted that the L-glutamine solution was added immediately before use. A DMSO solution containing MTX-CiKD_MLN was mixed with the medium so that the concentration of DMSO was 1 vol %, and added to each well where the pre-culture medium had been removed at 500 μL/well, and cultured under conditions of 37° C. and 5 vol % $CO_2$. It is noted that a DMSO solution containing MTX or DMSO was used as a control in place of the DMSO solution containing MTX-CiKD_MLN.

(Evaluation of Affinity of MTX-CiKD_MLN with Target by Thermal Shift Assay)

The medium was removed 3 hours after addition of MTX-CiKD_MLN (40 μM) or MTX (40 μM), and then PBS (Wako Pure Chemical Industries, Ltd.) at 37° C. was added to each well at 1 mL/well to wash the cells. After removing PBS, trypsin (0.25 w/v % trypsin-1 mmol/L EDTA-4 Na solution with phenol red) (Wako Pure Chemical Industries, Ltd.) at 37° C. was added to each well at 200 μL/well, and cultured under conditions of 37° C. and 5 volt $CO_2$ for 1 minute. After culturing, a medium where 10 mass % FBS (Code No. SH30910.03, Lot. No. AYG161516, HyClone) and 1 mass % PenStrep (100 U/mL sodium penicillin G and 100 μg/mL streptomycin sulfate) (Code No. 168-23191, Wako Pure Chemical Industries, Ltd.) were added to D-MEM (low D-glucose, L-glutamine, phenol red (Code No. 041-29775, Wako Pure Chemical Industries, Ltd.) was added to each well at 0.8 mL/well, and suspended, and then a cell solution was collected in a 15 mL tube.

The cell solution collected was centrifuged (at 1000 rpm×5 minutes, 4° C.), and the supernatant was removed, and then suspended in 2 ml of PBS (37° C.). The cell solution after suspension was centrifuged (at 1000 rpm×5 minutes, 4° C.), and the supernatant was removed, and then 170 μL of a CETSA buffer (cOmplete™ Mini, EDTA-free (Roche) as a protease inhibitor was added to TBS just before use) was added, and then suspended. The cell solution after suspension was dispensed to nine 1.5 mL tubes at 20 μL per tube, and allowed to stand at room temperature for 30 minutes. After allowed to stand, the 9 tubes were heat-treated for 3 minutes, one each at 38° C., 42° C., 46° C., 50° C., 54° C., 58° C., 62° C., 66° C., or 70° C., and allowed to stand at room temperature for 3 minutes. After allowed to stand, the cell solution was flash frozen in liquid nitrogen, and thawed on ice. After repeating this freeze-thaw cycle for 3 times, the cell solution was centrifuged (at 13500 rpm×20 minutes, 4° C.), and the supernatant (cell extract) was collected.

The cell extract collected was subjected to Western blot analysis. An SDS-PAGE gel (14 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. The electrophoresis samples prepared were applied to each well at 17 μL/well. Precision Plus Protein™ Dual Color Standards (Bio-Rad) were used as electrophoresis markers. Electrophoresis was performed at 160 V for 60 minutes (electrophoresis buffer; 195 mM glycine, 25 mM Tris).

After electrophoresis, proteins were transferred to a PVDF membrane (Immobion™-P, Millipore) under conditions of 100 V and 2 hours using a tank-type blotting device and a transfer buffer (25 mM Tris-HCl, 195 mM glycine, 0.01% SDS, 15% methanol). The membrane after transfer was shaken and blocked in 5% skim milk/TBS-T (100 mM Tris-HCl, 150 mM NaCl, 0.1% Tween-20, pH 7.6) at room temperature for 30 minutes. After blocking, a primary antibody reaction was performed in 5% skim milk/TBS-T. As a primary antibody, anti-DHFR antibody (sc-377091, Santa-Cruz) diluted 500 times was used. After shaken at 4° C. overnight, the membrane was washed with TBS-T for 5 minutes. It is noted that washing was performed for 3 times. After the primary antibody reaction, a secondary antibody reaction was performed in 2% skim milk/TBS-T. As a secondary antibody, anti-mouse IgG (H+L) antibody (A90-116P-33, BETHYL) diluted 10000 times was used. The membrane was shaken at room temperature for 30 minutes, and then washed with TBS-T for 5 minutes. It is noted that washing was performed for 3 times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJI-FILM Corporation).

Figure 9:
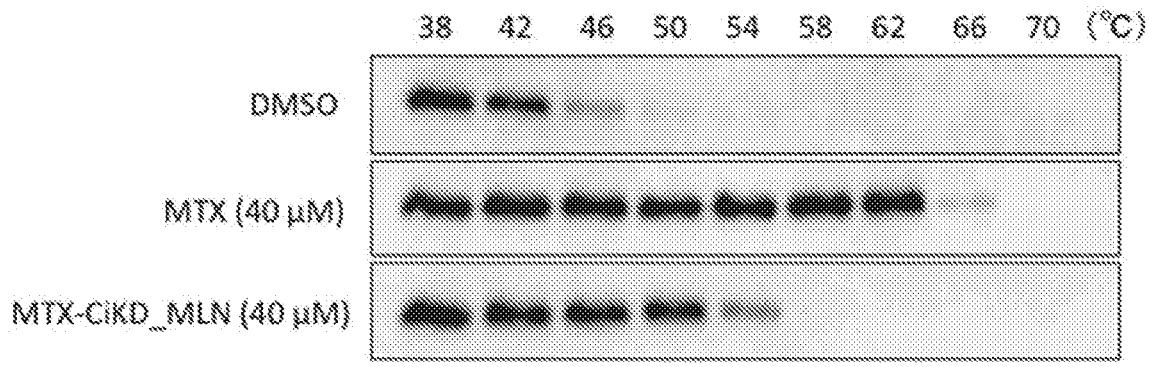
FIG. 9 shows results from the thermal shift assay of an endogenously expressed target protein (human DHFR) in HeLa cells to which MTX-CiKD_MLN or MTX was added.

FIG. 9 shows results from the thermal shift assay of an endogenously expressed target protein (human DHFR) in HeLa cells to which MTX-CiKD_MLN or MTX was added. As shown in FIG. 9, human DHFR was able to be detected only up to about 42° C. for the control (DMSO) while human DHFR was able to be detected up to about 50° C. by virtue of interaction between human DHFR and MTX-CiKD_MLN when MTX-CiKD_MLN (40 μM) was added. These results indicate that MTX-CiKD_MLN, in which MTX-$NH_2$ was linked to CiKD_MLN, had an affinity with human DHFR.

Example 15

Evaluation (Western Blot Analysis) of Degradation (Knockdown) of Endogenously Expressed Target Protein (Human DHFR) in HeLa Cells to which Protein-Degradation Inducing Molecule (MTX-CiKD_MLN) was Added In Example 15, degradation (knockdown) of an endogenously expressed target protein (human DHFR) in HeLa cells to which MTX-CiKD_MLN was added was evaluated by Western blot analysis.

(Preparation of Cultured Cells and Cell Seeding)

HeLa cells were prepared, and seeded on a 24-well plate as in Example 14.

(Addition of Protein-Degradation Inducing Molecule (MTX-CiKD_MLN) to HeLa Cells)

MTX-CiKD_MLN was added to HeLa cells as in Example 14. A DMSO solution containing MTX or DMSO was used as a control in place of the DMSO solution containing MTX-CiKD_MLN.

(Evaluation of Target Degradation (Knockdown) Due to MTX-CiKD_MLN by Western Blot Analysis)

The medium was removed 16 hours after addition of MTX-CiKD_MLN (50 μM, 100 μM, or 200 μM) or MTX (50 μM, 100 μM, or 200 μM), and then PBS (Wako Pure Chemical Industries, Ltd.) at 4° C. was added to each well at 1 mL/well to wash the cells. After removing PBS, a mixed solution of a cell lysis buffer (CelLytic™ M, Sigma) and a protease inhibitor (cOmplete™ Mini, EDTA-free (REF 11 836 170 001), Roche) was added to each well at 27 μL/well. After allowed to stand at 4° C. for 15 minutes, cells were detached with a pipette tip (P1000) on ice. A cell solution was collected in a 1.5 mL tube, and flash frozen in liquid nitrogen, and then thawed on ice. After thawed, the cell solution was centrifuged (at 12000 rpm×15 minutes, 4° C.), and the supernatant (cell extract) was collected.

The cell extract collected was subjected to Western blot analysis. An SDS-PAGE gel (14 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. The electrophoresis samples prepared were applied to each well at 20 µL/well. Precision Plus Protein™ Dual Color Standards (Bio-Rad) were used as electrophoresis markers. Electrophoresis was performed at 160 V for 65 minutes (electrophoresis buffer; 195 mM glycine, 25 mM Tris).

After electrophoresis, proteins were transferred to a PVDF membrane (Immobion™-P, Millipore) under conditions of 100 V and 2 hours using a tank-type blotting device and a transfer buffer (25 mM Tris-HCl, 195 mM glycine, 0.01% SDS, 15% methanol). The Membrane was split into two at the position of a 25 kDa marker. The membrane after transfer was shaken and blocked in 5% skim milk/TBS-T (100 mM Tris-HCl, 150 mM NaCl, 0.1% Tween-20, pH 7.6) at room temperature for 30 minutes. After blocking, a primary antibody reaction was performed in 5% skim milk/TBS-T. As a primary antibody, anti-DHFR antibody (sc-14780, SantaCruz, diluted 500 times) and anti-GAPDH antibody (sc-32233, SantaCruz, diluted 20000 times) were used. After shaken at room temperature for 90 minutes (anti-DHFR antibody) or for 45 minutes (anti-GAPDH antibody), the membranes were washed with TBS-T for 5 minutes. It is noted that washing was performed for 3 times. After the primary antibody reaction, a secondary antibody reaction was performed in 2% skim milk/TBS-T. The membranes were shaken at room temperature for 30 minutes, and then washed with TBS-T for 5 minutes. It is noted that washing was performed for 3 times. Further, the membranes were washed with TBS (100 mM Tris-HCl, 150 mM NaCl, pH 7.6) for 5 minutes. Subsequently, the membranes were treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 10A:
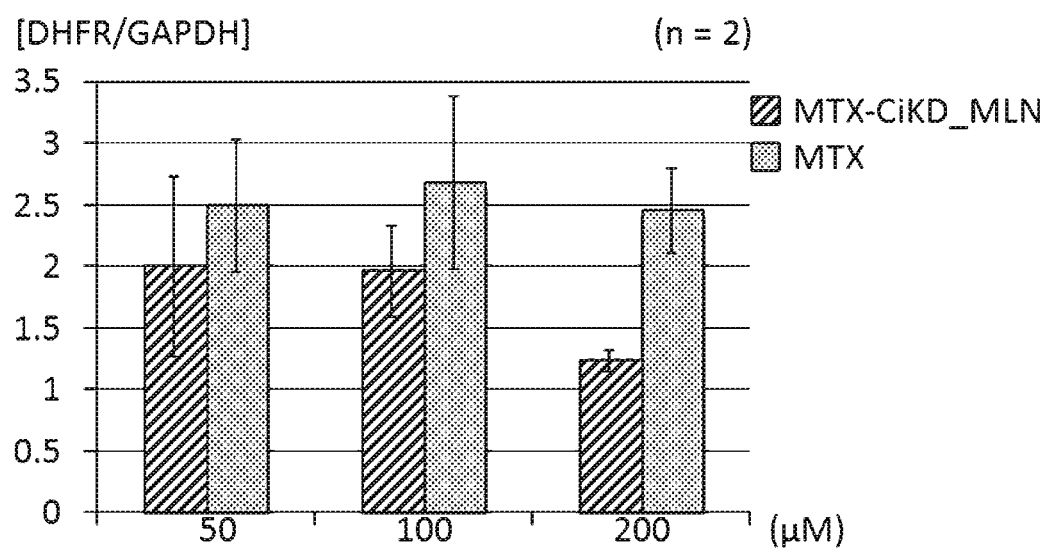
FIG. 10A shows results from quantification of bands detected in the Western blot analysis of an endogenously expressed target protein (human DHFR) in HeLa cells to which MTX-CiKD_MLN or MTX was added.
Figure 10B:
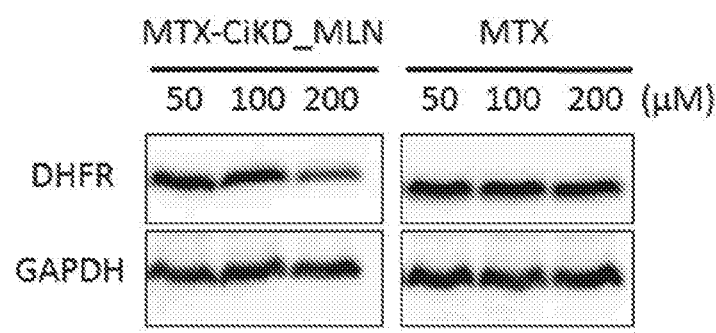
FIG. 10B shows bands detected in the Western blot analysis of an endogenously expressed target protein (human DHFR) in HeLa cells to which MTX-CiKD_MLN or MTX was added.

FIG. 10A shows results from quantification of bands detected in the Western blot analysis of the endogenously expressed target protein (human DHFR) in HeLa cells to which MTX-CiKD_MLN or MTX was added. FIG. 10B shows the detected bands. As can be seen in FIGS. 10A and 10B, the amount of the target protein (human DHFR) was decreased in a concentration dependent manner when MTX-CiKD_MLN was added. In contrast, when MTX was added, a decrease in the amount of the target protein (human DHFR) was not observed even at a concentration of 200 µM.

Example 16

Evaluation of Degradation (Knockdown) of Endogenously Expressed Target Protein (Mouse DHFR) in Mouse Individuals to which Protein-Degradation Inducing Molecule (MTX-CiKD_MLN) is Administered In Example 16, degradation (knockdown) of an endogenously expressed target protein (mouse DHFR) in mouse individuals to which MTX-CiKD_MLN was administered was evaluated by Western blot analysis.
(Administration of Protein-Degradation Inducing Molecule (MTX-CiKD_MLN) to Mice)

DMSO, 10 mg/kg of MTX, 50 mg/kg of MTX-CiKD_MLN, or 100 mg/kg of MTX-CiKD_MLN was administered to C57BL/6J wild type mice (7 weeks old, male) (CLEA Japan, Inc.) for 24 hours (n=3). MTX-CiKD_MLN and MTX were dissolved in DMSO, and then dissolved in corn oil (Code No. 25606-55, Nacalai Tesque, Inc.) so that the concentration of DMSO was 10 vol %, and then administered intraperitoneally. The mice were kept under an environment of ad libitum access to food and water. The mice were dissected under deep Somnopentyl anesthesia (serial number: 3214101, Kyoritsuseiyaku Corporation) 24 hours after administration. The liver, kidney, spleen, heart, and lung were excised, and flash freeze in liquid nitrogen.
(Western Blot Analysis of Mouse Tissues)

The frozen liver (40 mg) was triturated, and then 980 µL of 1×TKM tissue lysis buffer (50 mM triethanolamine (pH 7.8), 50 mM KCl, 5 mM $MgCl_2$, 0.25 M sucrose, 1 mM PMSF, Protein Inhibitors Cocktail-EDTA free (Code No. 03969-21, Nacalai Tesque, Inc.), 1 mM DTT, recombinant RNase inhibitor 5 µL/mL (40 U/µL, Cat No. 2313A, Lot No. K8402DA, TAKARA) were added, and rotated for 15 minutes (1 rpm, 25° C.). After centrifugation (at 3000 rpm×15 minutes, 4° C.), the supernatant (liver tissue extract) was collected. The concentration of extracted proteins was quantified with a spectrophotometer.

The liver tissue extract collected was subjected to Western blot analysis. An SDS-PAGE gel (14 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 5 minutes. The electrophoresis samples prepared were applied at 100 µg/20 µL/well (for detection of DHFR) or 50 µg/10 µL/well (for detection of GAPDH). Precision Plus Protein™ Dual Color Standards (Bio-Rad) were used as electrophoresis markers. Electrophoresis was performed at 160 V for 60 minutes (electrophoresis buffer; 195 mM glycine, 25 mM Tris).

After electrophoresis, proteins were transferred to a PVDF membrane (Immobion™-P, Millipore) under conditions of 100 V and 90 minutes using a tank-type blotting device and a transfer buffer (25 mM Tris-HCl, 195 mM glycine, 0.01% SDS, 15% methanol). The membrane after transfer was shaken and blocked in 5% skim milk/TBS-T (100 mM Tris-HCl, 150 mM NaCl, 0.1% Tween-20, pH 7.6) at room temperature for 30 minutes. After blocking, a primary antibody reaction was performed in 5% skim milk/TBS-T. As a primary antibody, anti-DHFR antibody (sc-14780, SantaCruz, diluted 500 times) and anti-GAPDH antibody (sc-32233, SantaCruz, diluted 20000 times) were used. The membrane was shaken at room temperature for 60 minutes, and then washed with TBS-T for 5 minutes. It is noted that washing was performed for 3 times. After the primary antibody reaction, a secondary antibody reaction was performed in 1% skim milk/TBS-T. The membrane was shaken at room temperature for 30 minutes, and then washed with TBS-T for 5 minutes. It is noted that washing was performed for 3 times. Further, the membrane was washed with TBS (100 mM Tris-HCl, 150 mM NaCl, pH 7.6) for 10 minutes. Subsequently, the membrane was treated with a chemiluminescence reagent Immobilon™ Western (Millipore), and then chemiluminescence was detected using a lumino image analyzer LAS-3000 (FUJIFILM Corporation).

Figure 11:
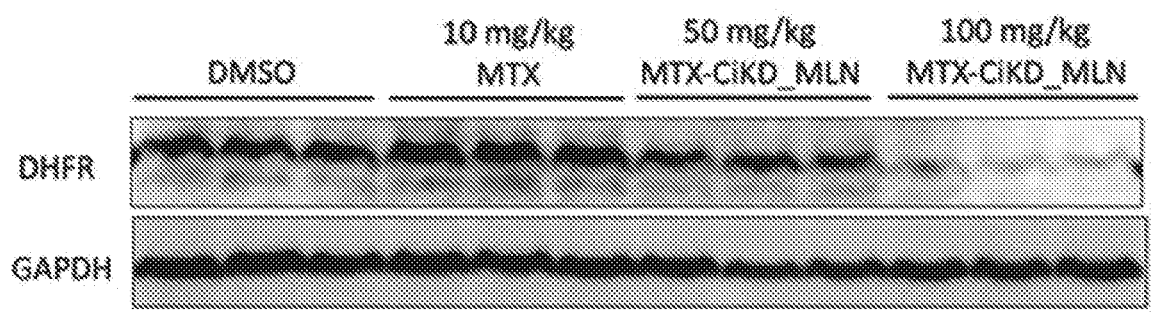
FIG. 11 shows results from the Western blot analysis of an endogenously expressed target protein (human DHFR) in a liver tissue extract from a mouse individual to which MTX-CiKD_MLN or MTX was administered.

FIG. 11 shows results from the Western blot analysis of an endogenous expressed target protein (mouse DHFR) in a liver tissue extract from a mouse individual to which MTX-CiKD_MLN or MTX was administered. As can be seen in FIG. 11, when 50 mg/kg or 100 mg/kg of MTX-CiKD_MLN was administered to mice for 24 hours, the amount of the target protein (mouse DHFR) in the liver tissue was decreased in a concentration dependent manner. These results show that about 70% to 80% of the target protein (mouse DHFR) was degraded as fast as one day in the mouse individuals. In contrast, when 10 mg/kg of MTX was administered to mice for 24 hours, the amount of the target protein (mouse DHFR) in the liver tissue was increased as compared with that of the control (DMSO).

Example 17

Synthesis of Protein-Degradation Inducing Molecule (TMP-CiKD_DMT) Using CiKD_DMT as Protein-Degradation Inducing Tag and TMP Derivative as Protein Binding Molecule In Example 17, TMP-CiKD_DMT as a protein-degradation inducing molecule was synthesized according to the following synthesis scheme. As a protein-degradation inducing tag, used was a compound (DMT) in which $R^1$ and $R^2$ in the aforementioned formula (I) were each a methoxy group. DMT is a compound which is not derived from a proteasome inhibitor, but has an affinity with a proteasome. As a protein binding molecule, TMP-$NH_2$ was used as in Example 1. Then, DMT was linked to TMP-$NH_2$ to synthesize TMP-CiKD_DMT as a protein-degradation inducing molecule.

reduced pressure. Separation and purification treatment was performed by silica gel chromatography (Code No. 30511-35, Nacalai Tesque, Inc.) (chloroform/methanol=92/8) to obtain TMP-CiKD_DMT (25.8 mg, 0.045 mmol, 62%, isolated yield).

Example 18

Evaluation of Proteasome Inhibitory Activity of Protein-Degradation Inducing Molecule (TMP-CiKD_DMT) and Affinity Thereof with Proteasome In Example 18, the proteasome inhibitory activity of TMP-CiKD_DMT and the affinity of TMP-CiKD_DMT with a proteasome were evaluated as in Example 4 except that 10 μM or 100 μM of TMP-CiKD_DMT was used in place of TMP-CiKD_Bortezomib. As a positive control, used was MG-132 as a proteasome inhibitor.

Figure 12A:
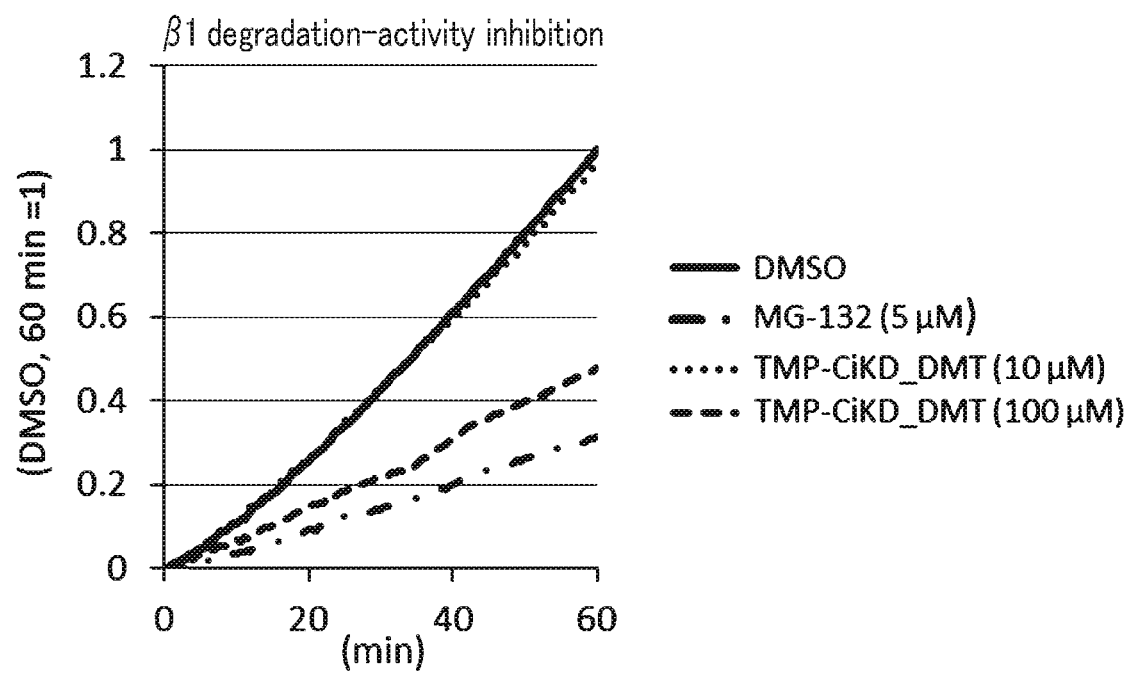
FIG. 12A shows the inhibitory activity of TMP-CiKD_DMT and MG-132 against the catalytic subunit β1 of the proteasome.
Figure 12B:
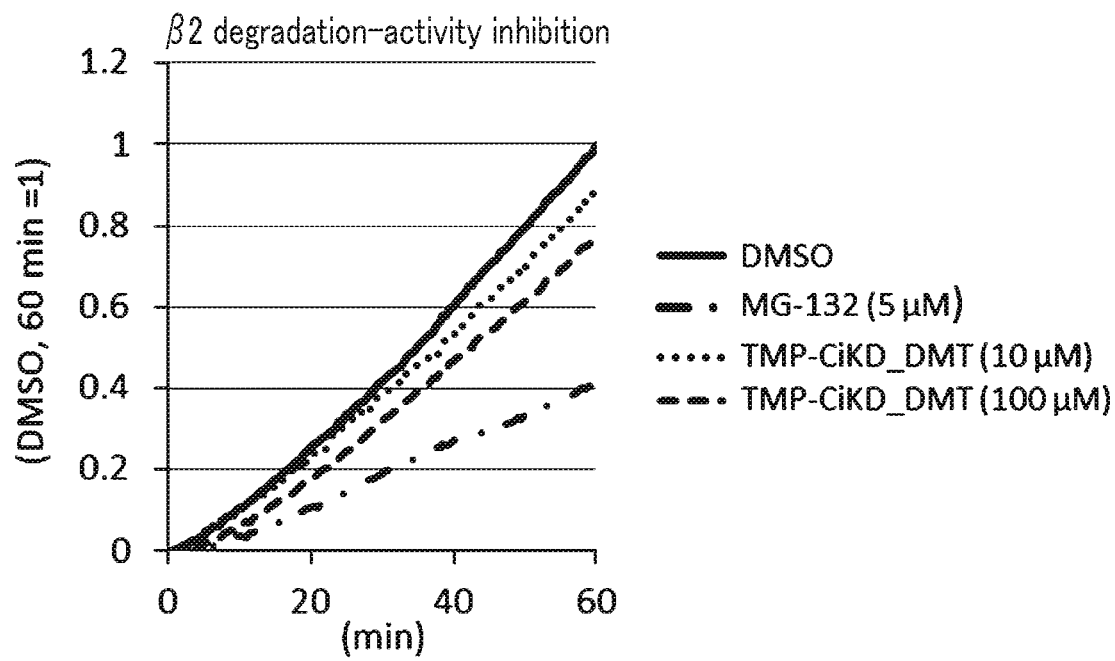
FIG. 12B shows the inhibitory activity of TMP-CiKD_DMT and MG-132 against the catalytic subunit β2 of the proteasome.
Figure 12C:
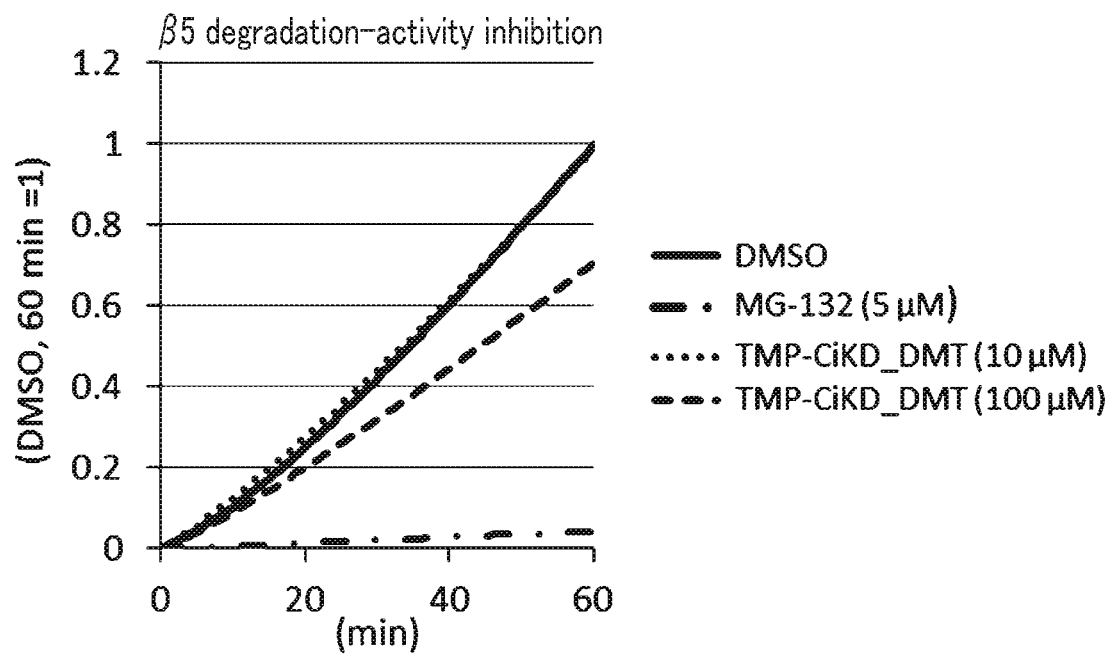
FIG. 12C shows the inhibitory activity of TMP-CiKD_DMT and MG-132 against the catalytic subunit β5 of the proteasome.

FIGS. 12A to 12C show the proteasome activities against β1 (caspase-like activity), β2 (trypsin-like activity), and β5 (chymotrypsin-like activity), respectively. As can be seen in FIGS. 12A to 12C, TMP-CiKD_DMT was found to have a significantly lower proteasome inhibitory activity as compared with MG-132. Moreover, the inhibitory activity of TMP-CiKD_DMT was increased in a concentration dependent manner against any of β1, β2, and β5, suggesting that TMP-CiKD_DMT has a moderate affinity with a protea-

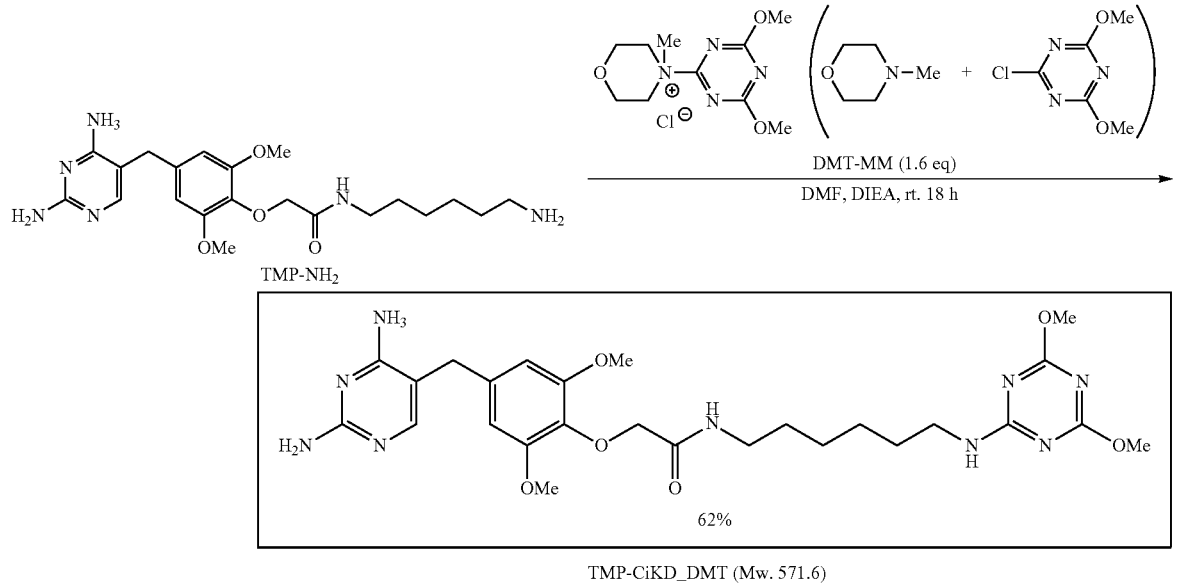

The method of synthesizing TMP-CiKD_DMT is described in detail as follows.

TMP-$NH_2$ (Long, M. J. et al., Chem. Biol., 2012, 19 (5), 629-637) (31.7 mg, 0.073 mmol) was charged into an eggplant flask, and 0.3 mL of dehydrate DMF was added. After stirred at room temperature for 10 minutes, 0.1 mL of DIEA was added, and stirred at room temperature for 10 minutes. DMT-MM (33.6 mg, 0.12 mmol, 1.6 eq, Code No. 329-53751, Wako Pure Chemical Industries, Ltd.) was directly added to the reaction solution, and stirred at room temperature for 18 hours. The reaction solution was diluted with water and aqueous sodium hydrogen carbonate, and extracted with chloroform for 5 times. After dried over anhydrous sodium sulfate, the solvent was evaporated under some. That is, DMT was evaluated to have an affinity with a proteasome, but does not inhibit degradation.

Example 19

Measurement of 50% Inhibition Concentration ($IC_{50}$) of Protein-Degradation Inducing Molecule (TMP-CiKD_DMT In Example 19, the 50% inhibition concentration ($IC_{50}$) of TMP-CiKD_DMT against each of the proteasome activities of β1, β2, and β5 of 20S proteasome was measured as in Example 5 except that TMP-CiKD_DMT was used in place of TMP-CiKD_Bortezomib. As a positive control, used was MLN2238 as a proteasome inhibitor.

The 50% inhibition concentrations (IC$_5$s) of TMP-CiKD_DMT and MLN2238 are shown in the following Table 87.

TABLE 87

| | IC$_{50}$ (μM) | | |
| --- | --- | --- | --- |
| | β1 | β2 | β5 |
| TMP-CiKD_DMT | >100 | >100 | 90.5 |
| MLN2238 | 0.0079 | 6.4 | 0.043 |

As can be seen in Table 87, TMP-CiKD_DMT was found to have a significantly lower proteasome inhibitory activity as compared with MLN2238.

Example 20

Evaluation (Thermal Shift Assay) of Affinity of Protein-Degradation Inducing Molecule (TMP-CiKD_ALLN) with Forcedly Expressed Target Protein (*E. coli* DHFR) in HeLa Cells to which Protein-Degradation Inducing Molecule (TMP-CiKD_DMT) was Added In Example 20, the affinity of TMP-CiKD_DMT with a forcedly expressed target protein (*E. coli* DHFR) in HeLa cells to which TMP-CiKD_DMT was added was evaluated by thermal shift assay.

(Preparation of Cultured Cells)

HeLa cells were prepared as in Example 2.

(Introduction of Plasmid into HeLa Cells and Cell Seeding)

A plasmid was introduced into HeLa cells to transiently overexpress ecDHFR as a target protein (specifically, a fusion protein of ecDHFR and GFP through a HA tag) or DsRed for comparison in the cells, and the effects of TMP-CiKD_DMT on the target protein were evaluated.

The plasmid (pMIR DsRed-IRES-ecDHFR-HA-GFP) was provided by Professor Lizbeth Hedstrom at Brandeis University (the United States) (Long, M. J. et al., "Inhibitor mediated protein degradation." Chem. Biol., 2012, 19 (5), 629-637). The plasmid was amplified in *E. coli*, and then purified with Miniprep Kit (Code No. 27106, QIAGEN).

ScreenFectA™ (Code No. 297-73201, Wako Pure Chemical Industries, Ltd.) as a transfection reagent was used to introduce the plasmid into HeLa cells. A dilution buffer of ScreenFect™ A was added to two 1.5 mL tubes at 250 UL per tube. Then, 12 μL of a transfection reagent of Screen-Fect™ A was added to one tube (a solution A), and 6 μg of the plasmid was added to the other tube (a solution B), and each tube was lightly pipetted, and then allowed to stand at room temperature for 2 minutes. The solution A was lightly mixed with the solution B, and allowed to stand at room temperature for 30 minutes (a solution C). The solution C was mixed in a cell solution of 6×10$^5$ cells/12 mL collected by trypsin treatment, and seeded on a 24-well plate (Code No. TR5002, TrueLine, and Nippon Genetics Co., Ltd.) at a cell density of 4×10$^4$ cells/800 μL/well, and then cultured under conditions of 37° C. and 5 vol % CO$_2$ for 40 hours.

(Addition of Protein-Degradation Inducing Molecule (TMP-CiKD_DMT) to HeLa Cells)

Culture was performed for 40 hours after introduction of the plasmid, and then TMP-CiKD_DMT was added to HeLa cells as follows. As a medium, used was a serum free medium (37° C.) in which 1 mass % L-glutamine solution (Code No. G7513, Sigma-Aldrich) was added to D-MEM (high D-glucose, phenol red, sodium pyruvate (Code No. 045-32245, Wako Pure Chemical Industries, Ltd.). It is noted that the L-glutamine solution was added immediately before use. A DMSO solution containing MTX-CiKD_DMT was mixed with the medium so that the concentration of DMSO was 1 vol %, and added to each well at 300 μL/well where the pre-culture medium had been removed, and cultured under conditions of 37° C. and 5 vol % CO$_2$. It is noted that a DMSO solution containing TMP or DMSO was used as a control in place of the DMSO solution containing TMP-CiKD_DMT.

(Evaluation of Affinity of TMP-CiKD_DMT with Target by Thermal Shift Assay)

The medium was removed 3 hours after addition of TMP-CiKD_DMT (28 μM) or TMP (40 μM), and then PBS (Wako Pure Chemical Industries, Ltd.) at 37° C. was added to each well at 1 mL/well to wash the cells. After removing PBS, trypsin (0.25 w/v % trypsin-1 mmol/L EDTA-4 Na solution with phenol red) (Wako Pure Chemical Industries, Ltd.) at 37° C. was added to each well at 300 μL/well, and cultured under conditions of 37° C. and 5 vol % CO$_2$ for 1 minutes. After culturing, a medium where 10 mass % FBS (Code No. SH30910.03, Lot. No. AYG161516, HyClone) and 1 mass % PenStrep (100 U/mL sodium penicillin G and 100 μg/mL streptomycin sulfate) (Code No. 168-23191, Wako Pure Chemical Industries, Ltd.) were added to D-MEM (low D-glucose, L-glutamine, phenol red (Code No. 041-29775, Wako Pure Chemical Industries, Ltd.) was added to each well at 1 mL/well, and suspended, and then a cell solution was collected in a 15 mL tube.

The cell solution collected was centrifuged (at 1000 rpm×5 minutes, 4° C.), and the supernatant was removed, and then suspended in 2 ml of PBS (37° C.). The cell solution after suspension was centrifuged (at 1000 rpm×5 minutes, 4° C.), and the supernatant was removed, and then 180 μL of a CETSA buffer (cOmplete™ Mini, EDTA-free (Roche) as a protease inhibitor was added to TBS immediately before use) was added and suspended. The cell solution after suspension was dispensed to nine 1.5 mL tubes at 20 μL per tube, and allowed to stand at room temperature for 30 minutes. After allowed to stand, the 9 tubes were heat-treated for 3 minutes, one each at 38° C., 42° C., 46° C., 50° C., 54° C., 58° C., 62° C., 66° C., or 70° C., and allowed to stand at room temperature for 3 minutes. After allowed to stand, the cell solution was flash frozen in liquid nitrogen, and thawed on ice. After repeating this freeze-thaw cycle for 3 times, the solution was centrifuged (at 13500 rpm×20 minutes, 4° C.), and the supernatant (cell extract) was collected.

The cell extract collected was subjected to Western blot analysis. An SDS-PAGE gel (14 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. The electrophoresis samples prepared were applied to each well at 17 μL/well. Precision Plus Protein™ Dual Color Standards (Bio-Rad) were used as electrophoresis markers. Electrophoresis was performed at 150 V for 40 minutes (electrophoresis buffer; 195 mM glycine, 25 mM Tris).

After electrophoresis, proteins were transferred to a PVDF membrane (Immobion™-P, Millipore) under conditions of 100 V and 40 minutes using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/high-salt TBS-T (100 mM Tris-HCl, 500 mM NaCl, 0.2% Tween-20, pH 7.6). After blocking, the membrane was rinsed with high-salt TBS-T, and an antibody reaction was performed in 1% skim milk/high-salt TBS-T. With regard to antibody, anti-HA-peroxidase, high-affinity (3F10) rat monoclonal antibody (25 U/mL) (Roche) diluted 1000 times was used. The membrane was shaken at room temperature for 90 minutes, and then washed with high-salt TBS-T for 5 minutes. It is noted that washing was performed for 3 times. Further, the membrane was washed with high-salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Figure 13:
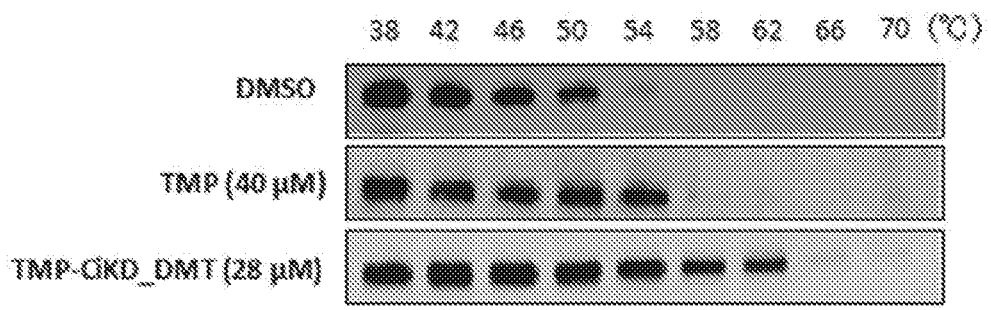
FIG. 13 shows results from the thermal shift assay of a forcedly expressed target protein (*E. coli* DHFR) in HeLa cells to which TMP-CiKD_DMT or TMP was added.

FIG. 13 shows results from the thermal shift assay of a forcedly expressed target protein (*E. coli* DHFR) in HeLa cells to which TMP-CiKD_DMT or TMP was added. *E. coli* DHFR was able to be detected only up to about 50° C. for the control (DMSO) while *E. coli* DHFR was able to be detected up to about 54° C. for TMP (40 µM) and up to about 62° C. for TMP-CiKD_DMT (28 µM). These results show that TMP-CiKD_DMT, in which TMP-NH$_2$ is linked to DMT, has a higher affinity with *E. coli* DHFR than TMP.

Example 21

Evaluation (FACS Analysis) of Degradation (Knockdown) of Forcedly Expressed Target Protein (*E. coli* DHFR) in HeLa Cells to which Protein-Degradation Inducing Molecule (TMP-CiKD_DMT) was Added In Example 21, degradation (knockdown) of a forcedly expressed target protein (*E. coli* DHFR) in HeLa cells to which TMP-CiKD_DMT was added was evaluated by FACS analysis.
(Preparation of Cultured Cells)
HeLa cells were prepared as in Example 2.
(Introduction of Plasmid into HeLa Cells and Cell Seeding)
A plasmid was introduced into HeLa cells to transiently overexpress *E. coli* DHFR as a target protein (specifically, a fusion protein of *E. coli* DHFR and GFP through a HA tag) or DsRed for comparison in the cells, and the effects of TMP-CiKD_DMT on the target protein were evaluated.

The plasmid (pMIR DsRed-IRES-ecDHFR-HA-GFP) was provided by Professor Lizbeth Hedstrom at Brandeis University (the United States) (Long, M. J. et al., "Inhibitor mediated protein degradation." Chem. Biol., 2012, 19 (5), 629-637). The plasmid was amplified in *E. coli*, and purified with Miniprep Kit (Code No. 27106, QIAGEN).

ScreenFect™ A (Code No. 297-73201, Wako Pure Chemical Industries, Ltd.) as a transfection reagent was used to introduce the plasmid into HeLa cells. A dilution buffer of ScreenFect™ A was added to two 1.5 mL tubes at 960 µL per tube. Then, 40 µL of a transfection reagent of ScreenFect™ A was added to one tube (a solution A), and 16 µg of the plasmid was added to the other tube (a solution B), and each tube was lightly pipetted, and then allowed to stand at room temperature for 2 minutes. The solution A was lightly mixed with the solution B, and allowed to stand at room temperature for 30 minutes (a solution C). The solution C was mixed with a cell solution of 2.7×10$^5$ cells/18 mL collected from trypsin treatment, and seeded on a 24-well plate (Code No. TR5002, TrueLine, Nippon Genetics Co., Ltd.) at a cell density of 6×10$^4$ cells/400 µL/well, and then cultured under conditions of 37° C. and 5 vol % CO$_2$ for 40 hours.
(Addition of Protein-Degradation Inducing Molecule (TMP-CiKD_DMT) to HeLa Cells)
TMP-CiKD_DMT was added to HeLa cells as follows. Culture was performed for 40 hours after introduction of the plasmid, and then the preculture medium was removed. Then, a serum-free medium (37° C.) in which 1 mass % L-glutamine solution (Code No. G7513, Sigma-Aldrich) was added to D-MEM (high D-glucose, phenol red, and sodium pyruvate (Code No. 045-32245, Wako Pure Chemical Industries, Ltd.) was added to each well at 297 µL/well. It is noted that the L-glutamine solution was added immediately before use. A DMSO solution containing a predetermined concentration of TMP-CiKD_DMT was added to each well at 3 µL/well, and cultured under conditions of 37° C. and 5 vol % CO$_2$. It is noted that a DMSO solution containing TMP or DMSO was used as a control in place of the DMSO solution containing TMP-CiKD_DMT.

The medium was removed 24 hours after addition of TMP-CiKD_DMT (56 µM or 112 µM) or TMP (80 µM), PBS (Wako Pure Chemical Industries, Ltd.) at 37° C. was added to each well at 1 mL/well to wash the cells. After removing PBS, trypsin (0.25 w/v % trypsin-1 mmol/L EDTA·4 Na solution with phenol red) (Wako Pure Chemical Industries, Ltd.) at 37° C. was added to each well at 300 µL/well, and cultured under conditions of 37° C. and 5 vol % CO$_2$ for 1 minute. After culturing, a medium where 10 mass % FBS (Code No. SH30910.03, Lot. No. AYG161516, HyClone) and 1 mass % PenStrep (100 U/mL sodium penicillin G and 100 µg/mL streptomycin sulfate) (Code No. 168-23191, Wako Pure Chemical Industries, Ltd.) were added to D-MEM (low D-glucose, L-glutamine, phenol red (Code No. 041-29775, Wako Pure Chemical Industries, Ltd.)) was added to each well at 500 µL/well, and suspended, and then a cell solution was collected in a 15 mL tube.

The cell solution collected was centrifuged (at 1000 rpm×5 minutes, 4° C.), and the supernatant was removed, and then suspended in 2 ml of PBS (37° C.). The cell solution after suspension was centrifuged (at 1000 rpm×5 minutes, 4° C.), and the supernatant was removed, and then 500 µL of an FACS buffer (1 mass % FBS/PBS) at 4° C. was added, and allowed to stand on ice.

A BD FACSCanto™ II (BD Biosciences) was used for flow cytometry, and the expression levels of GFR and DsRed in the cells were quantified. The cell solution was passed through a mesh with a pore size of β2 µm, and transferred to an FACS tube immediately before FACS analysis. The GFR/DsRed ratio per cell was computed using an analysis software FLOWJO™ (TOMY Digital Biology Co., Ltd.), and the efficiency of target degradation (knockdown) by TMP-CiKD_DMT was determined from a shift in a graph of target degradation.

Figure 14A:
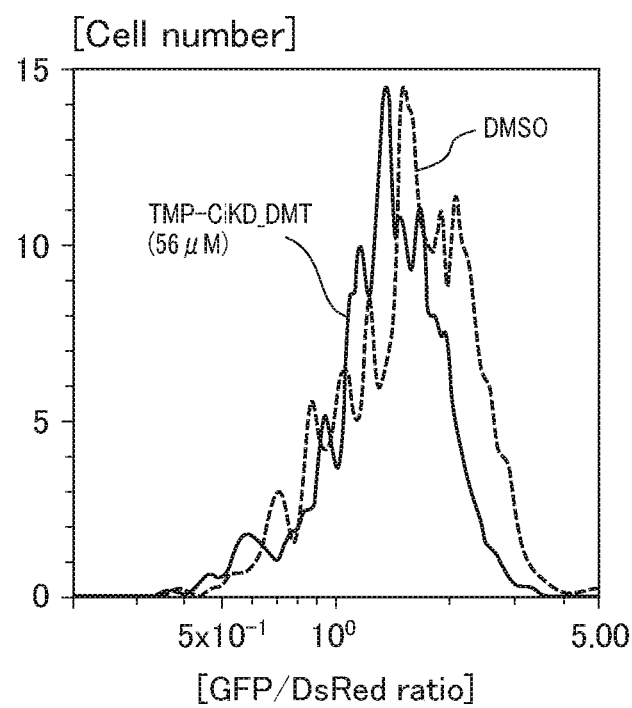
FIG. 14A shows results from the FACS analysis of a forcedly expressed target protein (*E. coli* DHFR) in HeLa cells to which TMP-CiKD_DMT was added.
Figure 14B:
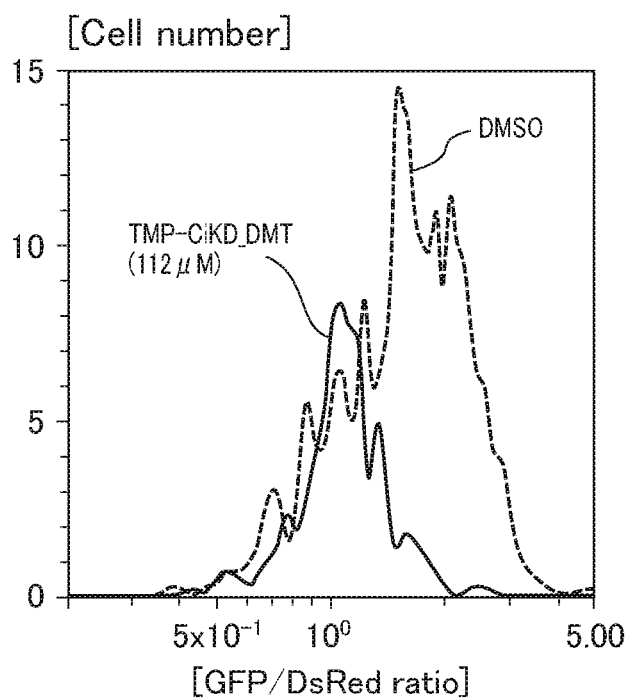
FIG. 14B shows results from the FACS analysis of a forcedly expressed target protein (*E. coli* DHFR) in HeLa cells to which TMP-CiKD_DMT was added.
Figure 14C:
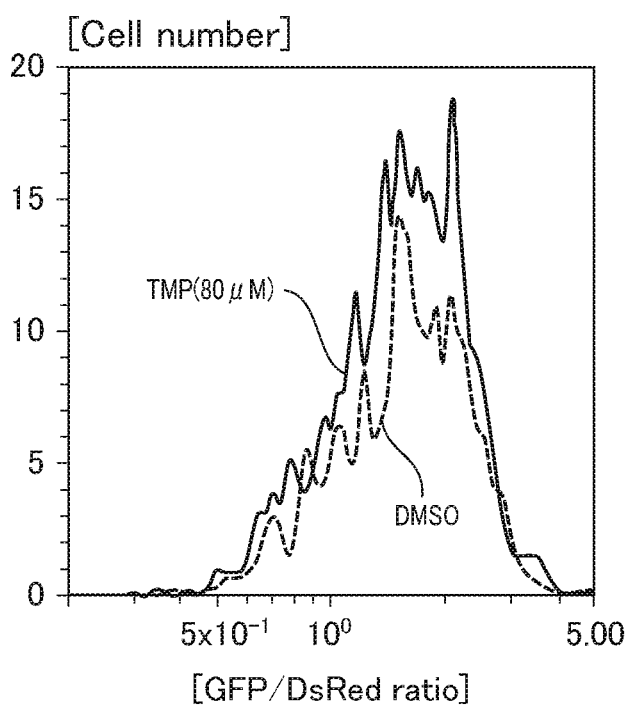
FIG. 14C shows results from the FACS analysis of a forcedly expressed target protein (*E. coli* DHFR) in HeLa cells to which TMP was added.

FIG. 14A shows results from the FACS analysis of a forcedly expressed target protein (*E. coli* DHFR) in HeLa cells to which TMP-CiKD_DMT (56 µM) was added. FIG. 14B shows results from the FACS analysis of a forcedly expressed target protein (*E. coli* DHFR) in HeLa cells to which TMP-CiKD_DMT (112 µM) was added. Further, FIG. 14C shows results from the FACS analysis of a forcedly expressed target protein (*E. coli* DHFR) in HeLa cells to which TMP was added. As can be seen from FIGS. 14A and 14B, when TMP-CiKD_DMT was added, the amounts of a shift to the left in the graphs were found to be increased as compared with the control (DMSO) in a concentration dependent manner, indicating that the target protein (*E. coli* DHFR) was degraded. The degradation efficiency estimated from the amount of a shift was about 60% to 70%. In contrast, as can be seen in FIG. 14C, the graph was found to be overlapped with that of the control (DMSO) when TMP was added, indicating that the target protein was not degraded.

Example 22

Evaluation (Western Blot Analysis) of Degradation (Knockdown) of Forcedly Expressed Target Protein (*E. coli* DHFR) in HeLa Cells to which Protein-Degradation Inducing Molecule (TMP-CiKD_DMT) was Added In Example 22, degradation (knockdown) of a forcedly expressed target protein (*E. coli* DHFR) in HeLa cells to which TMP-CiKD_DMT was added was evaluated by Western blot analysis.

(Preparation of Cultured Cells)

HeLa cells were prepared as in Example 2.

(Introduction of Plasmid into HeLa Cells and Cell Seeding)

A plasmid was introduced into HeLa cells to transiently overexpress *E. coli* DHFR as a target protein (specifically, a fusion protein of *E. coli* DHFR and GFP through a HA tag) or DsRed for comparison in the cells, and the effects of TMP-CiKD_DMT on the target protein were evaluated.

The plasmid (pMIR DsRed-IRES-ecDHFR-HA-GFP) was provided by Professor Lizbeth Hedstrom at Brandeis University (the United States) (Long, M. J. et al., "Inhibitor mediated protein degradation." Chem. Biol., 2012, 19 (5), 629-637). The plasmid was amplified in *E. coli*, and purified with Miniprep Kit (Code No. 27106, QIAGEN).

ScreenFect™ A (Code No. 297-73201, Wako Pure Chemical Industries, Ltd.) as a transfection reagent was used to introduce the plasmid into HeLa cells. A dilution buffer of ScreenFect™ A was added to two 1.5 mL tubes at 250 µL per tube. Then, 12 µL of a transfection reagent of ScreenFect™ A was added to one tube (a solution A), and 4.8 µg of the plasmid was added to the other tube (a solution B), and each tube was lightly pipetted, and then allowed to stand at room temperature for 2 minutes. The solution A was lightly mixed with the solution B, and allowed to stand at room temperature for 30 minutes (a solution C). The solution C was mixed with a cell solution of $7.7 \times 10^4$ cells/7.7 mL collected from trypsin treatment, and seeded on a 24-well plate (Code No. TR5002, TrueLine, Nippon Genetics Co., Ltd.) at a cell density of $4 \times 10^4$ cells/400 µL/well, and then cultured under conditions of 37° C. and 5 vol % $CO_2$ for 40 hours.

(Addition of Protein-Degradation Inducing Molecule (TMP-CiKD_DMT) to HeLa Cells)

Culture was performed for 40 hours after introduction of the plasmid, and then TMP-CiKD_DMT was added to HeLa cells as follows. As a medium, used was a serum free medium (37° C.) in which 1 mass % L-glutamine solution (Code No. G7513, Sigma-Aldrich) was added to D-MEM (high D-glucose, phenol red, sodium pyruvate (Code No. 045-32245, Wako Pure Chemical Industries, Ltd.)). It is noted that the L-glutamine solution was added immediately before use. A DMSO solution containing TMP-CiKD_DMT was mixed with the medium so that the concentration of DMSO was 1 vol %, and added to each well at 300 µL/well where the pre-culture medium had been removed, and cultured under conditions of 37° C. and 5 vol % $CO_2$. Further, an experiment group where a DMSO solution containing TMP-CiKD_DMT and bortezomib was added was also prepared in addition to an experiment group where a DMSO solution containing TMP-CiKD_DMT was added. Cycloheximide as a protein synthesis inhibitor was added to the medium so as to give a concentration of 50 µg/mL 12 hours after addition of TMP-CiKD_DMT or TMP-CiKD_DMT and bortezomib. It is noted that a DMSO solution containing TMP or DMSO was used as a control in place of the DMSO solution containing TMP-CiKD_DMT.

(Evaluation of Target Degradation (Knockdown) Due to TMP-CiKD_DMT by Western Blot Analysis)

The medium was removed 24 hours after addition of TMP-CiKD_DMT or TMP-CiKD_DMT and bortezomib, and 1 mL of PBS (Wako Pure Chemical Industries, Ltd.) at 4° C. was added to each well to wash the cells. After removing PBS, a mixed solution of a cell lysis buffer (CelLytic™ M, Sigma) and a protease inhibitor (cOmplete™ Mini, EDTA-free (REF 11 836 170 001), Roche) was added to each well at 55 µL/well. After allowed to stand at 4° C. for 15 minutes, cells were detached with a pipette tip (P1000) on ice. A cell solution was collected in a 1.5 mL tube, and flash frozen in liquid nitrogen, and then thawed on ice. After repeating this freeze-thaw cycle for 3 times, the solution was centrifuged (at 13000 rpm×20 minutes, 4° C.), and the supernatant (cell extract) was collected.

The cell extract collected was subjected to Western blot analysis. An SDS-PAGE gel (8 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. The electrophoresis samples prepared were applied to each well at 40 µL/well. Precision Plus Protein™ Dual Color Standards (Bio-Rad) were used as electrophoresis markers. Electrophoresis was performed at 150 V for 50 minutes (electrophoresis buffer; 195 mM glycine, 25 mM Tris).

After electrophoresis, proteins were transferred to a PVDF membrane (Immobion™-P, Millipore) under conditions of 100 V and 40 minutes using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/high-salt TBS-T (100 mM Tris-HCl, 500 mM NaCl, 0.2% Tween-20, pH 7.6). After blocking, the membrane was rinsed with high-salt TBS-T, and an antibody reaction was performed in 1% skim milk/high-salt TBS-T. With regard to antibody, anti-HA-peroxidase, high-affinity (3F10) rat monoclonal antibody (25 U/mL) (Roche) diluted 1000 times was used. The membrane was shaken at room temperature for 1 hour, and then washed with high-salt TBS-T for 5 minutes. It is noted that washing was performed for 3 times. Further, the membrane was washed with high-salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Next, a reaction for detecting GAPDH as a control was performed using the same membrane. The membrane was washed with TBS-T (100 mM Tris-HCl, 150 mM NaCl, 0.1% Tween-20, pH 7.6), and blocked by shaking at room temperature for 30 minutes in 5% skim milk/TBS-T. After blocking, a primary antibody reaction was performed in 5% skim milk/TBS-T. As a primary antibody, anti-GAPDH antibody (sc-32233, SantaCruz, diluted 20000 times) was used. The membrane was shaken at room temperature for 60 minutes, and then washed with TBS-T for 5 minutes. It is noted that washing was performed for 3 times. After the primary antibody reaction, a secondary antibody reaction was performed in 2% skim milk/TBS-T. As a secondary antibody, anti-mouse IgG (H+L) antibody (A90-116P-33, BETHYL) diluted 20000 times was used. The membrane was shaken at room temperature for 30 minutes, and then washed with TBS-T for 5 minutes. It is noted that washing was performed for 3 times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 15A:
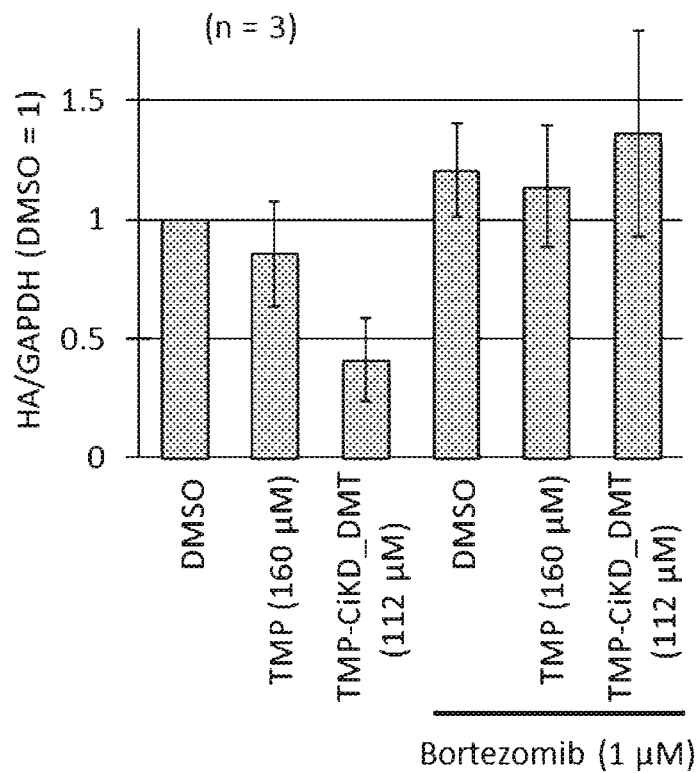
FIG. 15A shows results from quantification of bands detected in the Western blot analysis of a forcedly expressed target protein (*E. coli* DHFR) in HeLa cells to which TMP-CiKD_DMT, TMP, or TMP-CiKD_DMT and bortezomib were added.
Figure 15B:
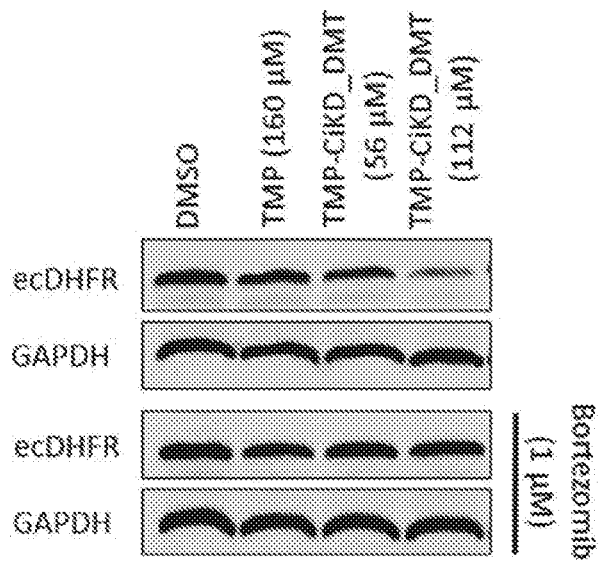
FIG. 15B shows bands detected in the Western blot analysis of a forcedly expressed target protein (*E. coli* DHFR) in HeLa cells to which TMP-CiKD_DMT, TMP, or TMP-CiKD_DMT and bortezomib were added.

FIG. 15A shows results from quantification of bands detected in the Western blot analysis of a forcedly expressed target protein (*E. coli* DHFR) in HeLa cells to which TMP-CiKD_DMT or TMP-CiKD_DMT and bortezomib were added. FIG. 10B shows the detected bands. As can be seen in FIGS. 15A and 15B, the degradation efficiency was about 60% relative to the control (DMSO) when TMP-CiKD_DMT (112 μM) was added. In contrast, degradation of the target protein was inhibited when TMP-CiKD_DMT (112 μM) and bortezomib (1 μM) were added. These results suggest that TMP-CiKD_DMT enabled the target protein to be led to degradation by a proteasome.

Example 23

Evaluation (Western Blot Analysis) of Degradation (Knockdown) of Forcedly Expressed Target Protein (*E. coli* DHFR) in HeLa Cells to which Protein-Degradation Inducing Molecule (TMP-CiKD_DMT, TMP-CiKD_MLN, TMP-CiKD_ALLN, or TMP-CiKD_Bortezomib) was Added In Example 23, degradation (knockdown) of a forcedly expressed target protein (*E. coli* DHFR) in HeLa cells to which TMP-CiKD_DMT, TMP-CiKD_MLN, TMP-CiKD_ALLN, or TMP-CiKD_Bortezomib were added was evaluated by Western blot analysis.

(Preparation of Cultured Cells)

HeLa cells were prepared as in Example 2.

(Introduction of Plasmid into HeLa Cells and Cell Seeding)

A plasmid was introduced into HeLa cells to transiently overexpress *E. coli* DHFR as a target protein (specifically, a fusion protein of *E. coli* DHFR and GFP through a HA tag) or DsRed for comparison in the cells, and the effects of TMP-CiKD_DMT on the target protein were evaluated.

The plasmid (pMIR DsRed-IRES-ecDHFR-HA-GFP) was provided by Professor Lizbeth Hedstrom at Brandeis University (the United States) (Long, M. J. et al., "Inhibitor mediated protein degradation." Chem. Biol., 2012, 19 (5), 629-637). The plasmid was amplified in *E. coli*, and purified with Miniprep Kit (Code No. 27106, QIAGEN).

ScreenFect™ A (Code No. 297-73201, Wako Pure Chemical Industries, Ltd.) as a transfection reagent was used to introduce the plasmid into HeLa cells. A dilution buffer of ScreenFect™ A was added to two 1.5 mL tubes at 400 μL per tube. Then, 20 μL of a transfection reagent of ScreenFect™ A was added to one tube (a solution A), and 10.3 μg of the plasmid was added to the other tube (a solution B), and each tube was lightly pipetted, and then allowed to stand at room temperature for 2 minutes. The solution A was lightly mixed with the solution B, and allowed to stand at room temperature for 30 minutes (a solution C). The solution C was mixed in a cell solution of $8\times10^5$ cells/16 mL collected by trypsin treatment, and seeded on a 24-well plate (Code No. TR5002, TrueLine, Nippon Genetics Co., Ltd.) at a cell density of $4\times10^4$ cells/800 μL/well, and then cultured under conditions of 37° C. and 5 volt $CO_2$ for 40 hours.

(Addition of Protein-Degradation Inducing Molecule (TMP-CiKD_DMT, TMP-CiKD_MLN, TMP-CiKD_ALLN, or TMP-CiKD_Bortezomib) to HeLa Cells)

Culture was performed for 40 hours after introduction of the plasmid, and then TMP-CiKD_DMT, TMP-CiKD_MLN, TMP-CiKD_ALLN, or TMP-CiKD_Bortezomib was added to HeLa cells as follows. As a medium, used was a serum free medium (37° C.) in which a 1 mass % L-glutamine solution (Code No. G7513, Sigma-Aldrich) was added to D-MEM (high D-glucose, phenol red, sodium pyruvate (Code No. 045-32245, Wako Pure Chemical Industries, Ltd.)). It is noted that the L-glutamine solution was added immediately before use. A DMSO solution containing TMP-CiKD_DMT, TMP-CiKD_MLN, TMP-CiKD_ALLN, or TMP-CiKD_Bortezomib was mixed with the medium so that the concentration of DMSO was 1 vol %, and added to each well at 300 μL/well where the pre-culture medium had been removed, and cultured under conditions of 37° C. and 5 vol % $CO_2$. It is noted that a DMSO solution containing TMP or DMSO was used as a control.

(Evaluation of Target Degradation (Knockdown) by Western Blot Analysis)

The medium was removed 24 hours after addition of TMP-CiKD_DMT, TMP-CiKD_MLN, TMP-CiKD_ALLN, or TMP-CiKD_Bortezomib, and PBS (Wako Pure Chemical Industries, Ltd.) at 4° C. was added to each well at 1 mL/well to wash the cells. After removing PBS, a mixed solution of a cell lysis buffer (CelLytic™ M, Sigma) and a protease inhibitor (cOmplete™ Mini, EDTA-free (REF 11 836 170 001), Roche) was added to each well at 30 μL/well. After allowed to stand at 4° C. for 10 minutes, cells were detached with a pipette tip (P1000) on ice. A cell solution was collected in a 1.5 mL tube, and flash frozen in liquid nitrogen, and then thawed on ice. After repeating this freeze-thaw cycle for 3 times, the solution was centrifuged (at 13500 rpm×20 minutes, 4° C.), and the supernatant (cell extract) was collected.

The cell extract collected was subjected to Western blot analysis. An SDS-PAGE gel (12 wells) was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. The electrophoresis samples prepared were applied to each well at 20 μL/well. Precision Plus Protein™ Dual Color Standards (Bio-Rad) were used as electrophoresis markers. Electrophoresis was performed at 160 V for 45 minutes (electrophoresis buffer; 195 mM glycine, 25 mM Tris).

After electrophoresis, proteins were transferred to a PVDF membrane (Immobion™-P, Millipore) under conditions of 100 V and 35 minutes using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/high-salt TBS-T (100 mM Tris-HCl, 500 mM NaCl, 0.2% Tween-20, pH 7.6). After blocking, the membrane was rinsed with high-salt TBS-T, and an antibody reaction was performed in 1% skim milk/high-salt TBS-T. With regard to antibody, anti-HA-peroxidase, high-affinity (3F10) rat monoclonal antibody (25 U/mL) (Roche) diluted 500 times was used. The membrane was shaken at room temperature for 2 hours, and then washed with high-salt TBS-T for 5 minutes. It is noted that washing was performed for 3 times. Further, the membrane was washed with high-salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Next, a reaction for detecting GAPDH as a control was performed using the same membrane. The membrane was washed with TBS-T (100 mM Tris-HCl, 150 mM NaCl, 0.1% Tween-20, pH 7.6), and blocked by shaking in 5% skim milk/TBS-T at room temperature for 30 minutes. After blocking, a primary antibody reaction was performed in 5% skim milk/TBS-T. As a primary antibody, anti-GAPDH antibody (sc-32233, SantaCruz, diluted 10000 times) was used. The membrane was shaken at room temperature for 60 minutes, and then washed with TBS-T for 5 minutes. It is noted that washing was performed for 3 times. After the primary antibody reaction, a secondary antibody reaction was performed in 2% skim milk/TBS-T. As a secondary antibody, anti-mouse IgG (H+L) antibody (A90-116P-33, BETHYL) diluted 20000 times was used. The membrane was shaken at room temperature for 30 minutes, and then washed with TBS-T for 5 minutes. It is noted that washing was performed for 3 times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 16:
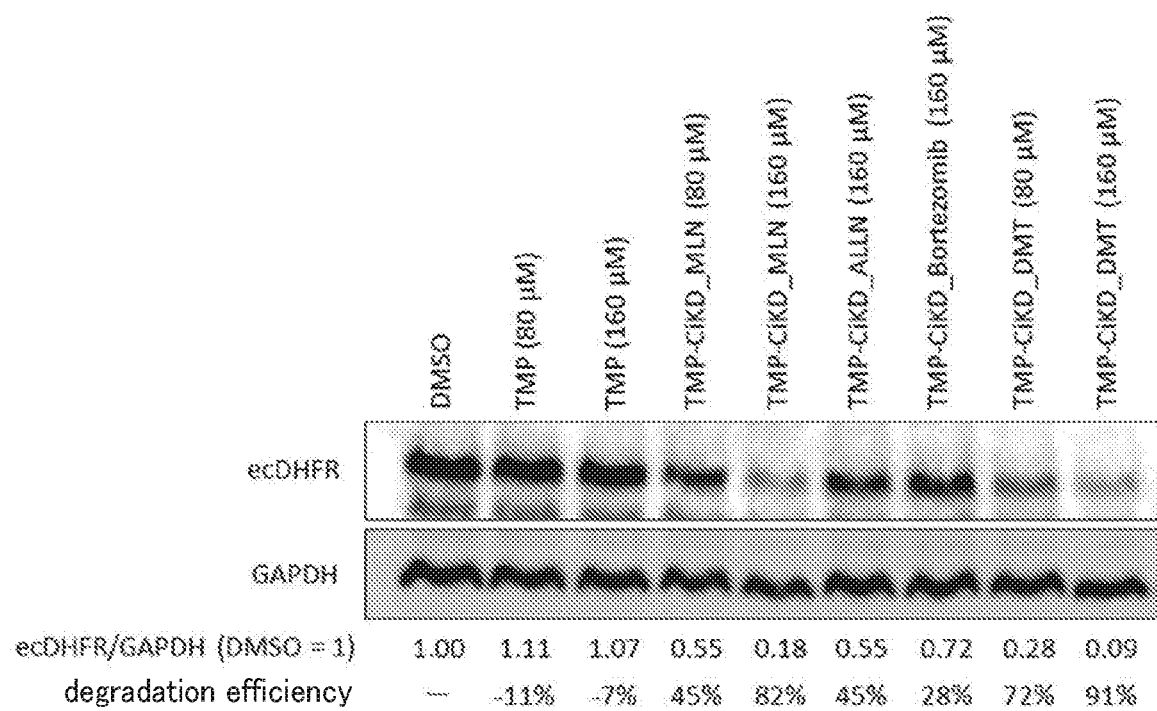
FIG. 16 shows results from the Western blot analysis of a forcedly expressed target protein (*E. coli* DHFR) in HeLa cells to which TMP-CiKD_DMT, TMP-CiKD_MLN, TMP-CiKD_ALLN, TMP-CiKD_Bortezomib, or TMP was added.

FIG. 16 shows results from the Western blot analysis of a forcedly expressed target protein (*E. coli* DHFR) in HeLa cells to which TMP-CiKD_DMT, TMP-CiKD_MLN, TMP-CiKD_ALLN, or TMP-CiKD_Bortezomib was added. As can be seen in FIG. 16, when TMP-CiKD_DMT was added in an amount of 80 μM or 160 μM, the degradation efficiency relative to the control (DMSO) was 72% or 91%, respectively. Moreover, the degradation efficiencies of TMP-CiKD_MLN, TMP-CiKD_ALLN, and TMP-CiKD_Bortezomib at 160 μM was 82%, 45%, and 28%, respectively.

The disclosures of Japanese Patent Application No. 2015-123740 filed on Jun. 19, 2015, and Japanese Patent Application No. 2016-078324 filed on Apr. 8, 2016 are entirely incorporated herein by reference. All documents, patent applications, and technical standards cited herein are incorporated herein by reference to the same extent as if each of the documents, patent applications, and technical standards was specifically and individually indicated to be incorporated by reference.

The invention claimed is:

1. A protein-degradation inducing molecule, which is a conjugate of at least one protein-degradation inducing tag and at least one protein binding molecule capable of binding to a target protein, the at least one protein-degradation inducing tag being a molecule having a molecular weight of 5000 or less and having an affinity with a 26S proteasome without inhibiting degradation of the target protein by the 26S proteasome,
the protein-degradation inducing molecule leading the target protein bound to the protein binding molecule to degradation by the 26S proteasome.

2. A library of protein-degradation inducing molecules, comprising two or more protein-degradation inducing molecules according to claim 1.

3. A pharmaceutical composition, comprising a protein-degradation inducing molecule according to claim 1 and a pharmaceutically acceptable carrier.

4. A method of degrading a target protein, the method comprising a step of contacting the target protein with a protein-degradation inducing molecule according to claim 1 to result in degradation of the target protein.

5. A protein-degradation inducing molecule, which is a conjugate of at least one protein-degradation inducing tag and at least one protein binding molecule capable of binding to a target protein, the at least one protein-degradation inducing tag being a molecule having an affinity with a 26S proteasome without inhibiting degradation of the target protein by the 26S proteasome,
the protein-degradation inducing molecule leading the target protein bound to the protein binding molecule to degradation by the 26S proteasome.

6. A culture medium for culturing cells, a tissue, or an organ comprising the protein-degradation inducing molecule according to claim 5.

7. A method for inducing protein degradation of a eukaryote or prokaryote having a protease in a living body, comprising orally or parenterally administering the protein-degradation inducing molecule according to claim 5 to said living body.

8. A protein-degradation inducing molecule, which is a conjugate of at least one protein-degradation inducing tag and at least one protein binding molecule capable of binding to a target protein, the at least one protein-degradation inducing tag being a molecule having an affinity with a 26S proteasome without inhibiting degradation of the target protein by the 26S proteasome,
the protein-degradation inducing molecule leading the target protein bound to the protein binding molecule to degradation by the 26S proteasome,
wherein the protein-degradation inducing tag has a structure represented by the formula (I), or a structure where a proteasome inhibitory activity of a proteasome inhibitor is inactivated, or a structure of a proteasome activating agent:

(I)

wherein $R^1$ and $R^2$ each independently represent a hydrocarbon group having 1 to 20 carbon atoms, an alkoxy group having 1 to 20 carbon atoms, an aryloxy group having 6 to 20 carbon atoms, a hydroxy group, a carboxy group, an amino group, or a halogeno group.

9. A library of protein-degradation inducing molecules, comprising two or more protein-degradation inducing molecules, each of the two or more protein-degradation inducing molecules being the protein-degradation inducing molecule according to claim 8.

10. A pharmaceutical composition, comprising the protein-degradation inducing molecule according to claim 8 and a pharmaceutically acceptable carrier.

11. A method of degrading a target protein, comprising contacting the target protein with the protein-degradation inducing molecule according to claim 8 to result in degradation of the target protein.

* * * * *